(12) United States Patent
Loomis et al.

(10) Patent No.: US 7,297,503 B2
(45) Date of Patent: Nov. 20, 2007

(54) METHODS OF IDENTIFYING REDUCED INTERNALIZATION TRANSMEMBRANE RECEPTOR AGONISTS

(75) Inventors: Carson R Loomis, Durham, NC (US); Robert H. Oakley, Durham, NC (US); Shuntai Wang, Chapel Hill, NC (US); Allen E. Eckhardt, Durham, NC (US)

(73) Assignee: Molecular Devices Corporation, Sunnyvale, CA (US)

( * ) Notice: Subject to any disclaimer, the term of this patent is extended or adjusted under 35 U.S.C. 154(b) by 171 days.

(21) Appl. No.: 10/693,164

(22) Filed: Oct. 24, 2003

(65) Prior Publication Data

US 2005/0009111 A1    Jan. 13, 2005

Related U.S. Application Data

(60) Provisional application No. 60/421,538, filed on Oct. 25, 2002.

(51) Int. Cl.
  *G01N 33/53*   (2006.01)
  *G01N 33/567*  (2006.01)
  *G01N 33/542*  (2006.01)
  *C12Q 1/66*    (2006.01)

(52) U.S. Cl. .................... 435/7.2; 435/7.9; 435/8; 530/350

(58) Field of Classification Search ................ None
See application file for complete search history.

(56) References Cited

U.S. PATENT DOCUMENTS

| | | | |
|---|---|---|---|
| 5,891,646 | A | 4/1999 | Barak et al. |
| 6,110,693 | A | 8/2000 | Barak et al. |
| 6,528,271 | B1 | 3/2003 | Bohn et al. |
| 6,716,588 | B2 * | 4/2004 | Sammak et al. ............. 435/7.2 |
| 6,770,449 | B2 | 8/2004 | Barak et al. |
| 6,800,445 | B2 | 10/2004 | Palmer et al. |
| 2003/0013137 | A1 | 1/2003 | Barak et al. |
| 2003/0049643 | A1 | 3/2003 | Barak et al. |
| 2005/0032125 | A1 | 2/2005 | Oakley et al. |

FOREIGN PATENT DOCUMENTS

| | | |
|---|---|---|
| WO | WO98/00715 | 1/1998 |
| WO | WO99/66324 | 12/1999 |
| WO | WO 01/46691 | 6/2001 |
| WO | WO 01/46694 | 6/2001 |
| WO | WO 02/46763 | 6/2002 |
| WO | WO 03/097795 | 11/2003 |
| WO | WO 2004/004451 | 1/2004 |

OTHER PUBLICATIONS

Ghosh, et al. J. Biomol. Screening 10(5): 476-484, 2005 'Quantitative Cell-Based High-Content Screening for Vasopressin Receptor Agonists Using Transfluor Technology'.*
Vassilatis, et al. PNAS 100 (8): 4903-4908 'The G protein-coupled receptor repertoires of human and mouse', 2003.*
Barak, Larry S., "Internal Trafficking and Surface Mobility of a Functionally Intact B2-Adrenergic Receptor-Green Fluorescent Protein Conjugate",*Molecular Pharmacology*, vol. 51, No. 2, pp. 177-184 (Feb. 1997), 177-184.
Bisello, Alessandro ,et al.,"Selective Ligand-induced Stabilization of Active and Desensitized Parathyroid Hormone Type 1 Receptor Conformations",*The Journal of Biological Chemistry*, vol. 277, No. 41, pp. 38524-38530 (Oct. 11, 2002).
Chen, Chongguang ,et al.,"Inverse Agonist Up-Regulates the Constitutively Active D3.49(164)Q Mutant of the Rat m-Opioid Receptor by Stabilizing the Structure and Blocking Constitutive Internalization and Down-Regulation",*Molecular Pharmacology*, vol. 60, No. 5, pp. 1064-1065 (Nov. 2001), 1064-1065.
Hanley, Nicole R.,et al.,"Mechanisms of Ligand-Induced Desensitization of the 5-Hydroxytryptamine2A Receptor",*The Journal of Pharmacology and Experimental Therapeutics*, vol. 300, No. 2, pp. 468-477 (Feb. 2002),467-477.
Emorine, L., et al., "Molecular characterization of the human β3-adrenergic receptor," *Science* 245:1118-1121 (Sep. 1989).

* cited by examiner

*Primary Examiner*—Robert S. Landsman
(74) *Attorney, Agent, or Firm*—Morgan, Lewis & Bockius LLP; David J. Brezner; Edward J. Baba

(57) ABSTRACT

Described herein are methods of identifying a transmembrane receptor (TMR) agonist and compounds identified by this method. The TMR agonist (TMRA) is capable of activating TMR signaling while exhibiting reduced TMR internalization over a control compound.

46 Claims, 60 Drawing Sheets

FIGURE 1

Human G Protein Coupled Receptor Family
(Receptors known as of January, 1999)

| CLASS | LIGAND | NUMBER | TISSUE | PHYSIOLOGY | THERAPEUTICS |
|---|---|---|---|---|---|
| Class I Rhodopsin like | | | | | |
| | • Amine | | | | |
| | • Acetylcholine (muscarinic & nicotinic) | 5 | Brain, Nerves, Heart | Neurotransmitter | Acuity, Alzheimer's |
| | • Adrenoceptors | | | | |
| | • Alpha Adrenoceptors | 6 | Brain, Kidney, Lung | Gluconeogenesis | Diabetes, Cardiovascular |
| | • Beta Adrenoceptors | 3 | Kidney, Heart | Muscle Contraction | Cardiovascular, Respiratory |
| | • Dopamine | 5 | Brain, Kidney, GI | Neurotransmitter | Cardiovascular, Parkinson's |
| | • Histamine | 2 | Vascular, Heart, Brain | Vascular Permeability | Anti-inflammatory, Ulcers |
| | • Serotonin (5-HT) | 16 | Most Tissues | Neurotransmitter | Depression, Insomnia, Analgesic |
| | • Peptide | | | | |
| | • Angiotensin | 2 | Vascular, Liver, Kidney | Vasoconstriction | Cardiovascular, Endocrine |
| | • Bradykinin | 1 | Liver, Blood | Vasodilation, | Anti-inflammatory, Asthma |
| | • C5a anaphylatoxin | 1 | Blood | Immune System | Anti-inflammatory |
| | • Fmet-leu-phe | 3 | Blood | Chemoattractant | Anti-inflammatory |
| | • Interleukin-8 | 1 | Blood | Chemoattractant | Anti-inflammatory |
| | • Chemokine | 6 | Blood | Chemoattractant | Anti-inflammatory |
| | • Orexin | 2 | Brain | Fat Metabolism | Obesity |
| | • Nociceptin | 1 | Brain | Bronchodilator, Pain | Airway Diseases, Anesthetic |
| | • CCK (Gastrin) | 2 | Gastrointestinal | Motility, Fat Absorption | Gastrointestinal, Obesity, Parkinson's |
| | • Endothelin | 2 | Heart, Bronchus, Brain | Muscle Contraction | Cardiovascular, Respiratory |
| | • Melanocortin | 5 | Kidney, Brain | Metabolic Regulation | Anti-inflammatory, Analgesics |
| | • Neuropeptide Y | 5 | Nerves, Intestine, Blood | Neurotransmitter | Behavior, Memory, Cardiovascular |
| | • Neurotensin | 1 | Brain, | CNS | Cardiovascular, Analgesic |
| | • Opioid | 3 | Brain, | CNS | Depression, Analgesic |
| | • Somatostatin | 5 | Brain, Gastrointestinal | Neurotransmitter | Oncology, Alzheimer's |

Figure 1, pg. 1 of 3

| | | | |
|---|---|---|---|
| ·Tachykinin | | | |
| (Substance P, NKA₁) | 3 | Brain Nerves | Neurohormone | Depression, Analgesic |
| ·Thrombin | 3 | Platelets, Blood Vessels | Coagulation | Anti-coagulant, Anti-inflammatory |
| ·Vasopressin-like | 4 | Arteries, Heart, Bladder | Water Balance | Anti-diuretic, Diabetic Complications |
| ·Galanin | 1 | Brain, Pancreas | Neurotransmitter | Analgesics, Alzheimer's |
| ·Hormone protein | | | | |
| ·Follicle stimulating hormone | 1 | Ovary, Testis | Endocrine | Infertility |
| ·Lutropin-choriogonadotropic | 1 | Ovary, Testis | Endocrine | Infertility |
| ·Thyrotropin | 1 | Thyroid | Endocrine | Thyroidism, Metabolism |
| ·(Rhod)opsin | | | | |
| ·Opsin | 5 | Eye | Photoreception | Ophthalmic Diseases |
| ·Olfactory | 4(~1000) | Nose | Smell | Olfactory Diseases |
| ·Prostanoid | | | | |
| ·Prostaglandin | 5 | Arterial, Gastrointestinal | Vasodilation, Pain | Cardiovascular, Analgesic |
| ·Lysophosphatidic Acid | 2 | Vessels, Heart, Lung | Inflammation | Cancer, Anti-Inflammatory |
| ·Sphingosine-1-phosphate | 2 | Most Cells | Cell proliferation | Cancer |
| ·Leukotriene | 1 | White Blood Cells, Bronchus | Inflammation | Asthma, Rheumatoid Arthritis |
| ·Prostacyclin | 1 | Arterial, Gastrointestinal | Platelet Regulation | Cardiovascular |
| ·Thromboxane | 1 | Arterial, Bronchus | Vasoconstriction | Cardiovascular, Respiratory |
| ·Nucleotide-like | | | | |
| ·Adenosine | 4 | Vascular, Bronchus | Multiple Effects | Cardiovascular, Respiratory |
| ·Purinoceptors | 4 | Vascular, Platelets | Relaxes Muscle | Cardiovascular, Respiratory |
| ·Cannabis | 2 | Brain | Sensory Perception | Analgesics, Memory |
| ·Platelet activating factor | 1 | Most Peripheral Tissues | Inflammation | Anti-inflammatory, Anti-asthmatic |
| ·Gonadotropin-releasing hormone like | | | | |
| ·Gonadotropin-releasing hormone | 1 | Reproductive Organs, Pituitary | Reproduction | Prostate Cancer, Endometriosis |
| ·Thyrotropin-releasing hormone | 1 | Pituitary, Brain | Thyroid Regulation | Metabolic Regulation |
| ·Growth hormone- inhibiting factor | 1 | Gastrointestinal | Neuroendocrine | Oncology, Alzheimer's |
| ·Melatonin | 1 | Brain, Eye, Pituitary | Neuroendocrine | Regulation of Circadian Cycle |

| | | | | |
|---|---|---|---|---|
| Class II Secretin like | | | | |
| | ·Secretin | 1 | Gastrointestinal, Heart | Digestion | Obesity, Gastrointestinal |
| | ·Calcitonin | 1 | Bone, Brain | Calcium Resorption | Osteoporosis |
| | ·Corticotropin releasing factor/urocortin | 1 | Adrenal, Vascular, Brain | Neuroendocrine | Stress, Mood, Obesity |
| | ·Gastric inhibitory peptide (GIP) | 1 | Adrenals, Fat Cells | Sugar/Fat Metabolism | Diabetes, Obesity |
| | ·Glucagon | 1 | Liver, Fat Cells, Heart | Gluconeogenesis | Cardiovascular |
| | ·Glucagon-like Peptide 1 (GLP-1) | 1 | Pancreas, Stomach, Lung | Gluconeogenesis | Cardiovascular, Diabetes, Obesity |
| | ·Growth hormone-releasing hormone | 1 | 1 | Brain | Neuroendocrine Growth Regulation |
| | ·Parathyroid hormone | 1 | Bone, Kidney | Calcium Regulation | Osteoporosis |
| | ·PACAP | 1 | Brain, Pancreas, Adrenals | Metabolism | Metabolic Regulation |
| | ·Vasoactive intestinal polypeptide (VIP) | 1 | Gastrointestinal | Motility | Gastrointestinal |
| ·Class III | | | | | |
| | ·Metabotropic Glutamate | 7 | Brain | Sensory Perception | Hearing, Vision |
| | ·GABA$_B$ | 1 | Brain | Neurotransmitter | Mood Disorders |
| | ·Extracellular Calcium Sensing | 1 | Parathyroid, Kidney, GI Tract | Calcium Regulation | Cataracts, GI Tumors |

Figure 2

G protein-coupled receptors:
(Division into Class A
Or Class B)

1. A1 adenosine receptor [Homo sapiens]. ACCESSION AAB25533
   npivyaf riqkfrvtfl kiwndhfrcq pappidedlp eerpdd
   Class A

2. adrenergic, alpha -1B-, receptor [Homo sapiens]. ACCESSION NP_000670
   npiiypcsskefkrafvrilgcqcrgrgrrrrrrrrrlggcaytyrpwtrggslersqsrkdslddsgsclsgsqrtlpsaspspgylgrgap
   ppvelcafpewkapgallslpapeppgrrgrhdsgplftfklltepespgtdggasnggceaaadvangqpgfksnmplapgqf
   Class A

3. adrenergic receptor alpha-2A [Homo sapiens]. ACCESSION AAG00447
   npviytifnhdfrrafkkilcrgdrkriv
   Class A

4. alpha-2B-adrenergic receptor - human. ACCESSION A37223
   npviytifnqdfrrafrrilcrpwtqtaw
   Class A

5. alpha-2C-adrenergic receptor - human. ACCESSION A31237
   npviytvfnqdfrpsfkhilfrrrrrgfrq
   Class A

6. beta-1-adrenergic receptor [Homo sapiens]. ACCESSION NP_000675
   npiiycrspdfrkafqgllccarraarrrhathgdrprasgclarpgpppspgaasdddddddvvgatpparllepwagcnggaaads
   d ssldepcrpgfaseskv
   Class A

7. beta-2 adrenergic receptor. ACCESSION P07550
   npliycrspdfriafqellclrrsslkaygngyssngntgeqsgyhveqekenkllcedlpgtedfvghqgtvpsdnidsqgrncstnd
   sll
   Class A

8. dopamine receptor D1 [Homo sapiens]. ACCESSION NP_000785
   npiiyafnadfrkafstllgcyrlcpatnnaietvsinnngaamfsshheprgsiskecnlvyliphavgssedlkkeeaagiarplekls
   palsvildydtdvslekiqpitqngqhpt
   Class A

9. D(2) dopamine receptor. ACCESSION P14416
   npiiyttfniefrkaflkilhc
   Class A

10. d3 dopamine receptor - human. ACCESSION G01977
   npviyttfniefrkaflkilsc
   Class A Figure 2
page 2

11. dopamine receptor D4 - human. ACCESSION DYHUD4
   npviytvfnaefmvfrkalracc
   Class A 12. dopamine receptor D5 - human. ACCESSION DYHUD5
   npviyafnadfqkvfaqllgcshfcsrtpvetvnisnelisynqdivfhkeiaaayihmmpnavtpgnrevdndeeegpfdrmfqi
   yqtspdgdpvaesvweldcegeisldkitpftpngfh
   Class A 13. muscarinic acetylcholine receptor M1 [Homo sapiens]. ACCESSION NP_000729
   npmcyalcnkafrdtfrllllcrwdkrrwrkipkrpgsvhrtpsrqc
   Class A 14. muscarinic acetylcholine receptor M2 [Homo sapiens]. ACCESSION NP_000730
   npacyalcnatfkktfkhllmchyknigatr
   Class A 15. muscarinic acetylcholine receptor M3 [Homo sapiens].
   npvcyalcnktfrttfkmlllcqcdkkkrrkqqyqqrqsvifhkrapeqal
   Class A 16. muscarinic acetylcholine receptor M4 [Homo sapiens]. ACCESSION NP_000732
   npacyalcnatfkktfrhlllcqymigtar
   Class A 17. m5 muscarinic receptor. locus HUMACHRM ACCESSION AAA51569
   npicyalcnrtfrktfkmlllcrwkkkkveeklywqgnsklp
   Class A 18. 5-hydroxytryptamine (serotonin) receptor 1A [Homo sapiens]. ACCESSION BAA90449
   npviyayfnkdfqnafkkiikckf
   Class A 19. 5-hydroxytryptamine (serotonin) receptor 1B [Homo sapiens]. ACCESSION BAA94455
   npiiytmsnedfkqafhklirfkcts
   Class A 20. 5-hydroxytryptamine (serotonin) receptor 1E [Homo sapiens]. ACCESSION BAA94458
   npllytsfnedfklafkklircre
   Class A

21. OLFACTORY RECEPTOR 6A1. ACCESSION O95222

Figure 2
page 3 npiiyclmqevkralccilhlyqhqdpdpkkgsrnv
    Class A

22. OLFACTORY RECEPTOR 2C1. ACCESSION O95371
npliytlmmevkgalrrllgkgrevg
    Class A 23. angiotensin receptor 1 [Homo sapiens]. ACCESSION NP_033611
nplfygflgkkfkryflqllkyippkakshsnlsfkmsflsyrpsdnvssstkkpapcfeve
    Class B 24. angiotensin receptor 2 [Homo sapiens]. ACCESSION NP_000677
npflycfvgnrfqqklrsvfrvpitwlqgkresmscrkssslremetfvs
    Class B 25. interleukin 8 receptor beta (CXCR2) [Homo sapiens]. ACCESSION NM_001557
NPLIYAFIGQKFRHGLLKILAIHGLISKDSLPKDSRPSFVGSSSGHTSTTL
    Class B 26. cx3c chemokine receptor 1 (cx3cr1) (fractalkine receptor)
ACCESSION P49238
npliyafagekfrrylyhlygkclavlcgrsvhvdfsssesqrsrhgsvlssnftyhtsdgdallll
    Class B 27. neurotensin receptor - human. ACCESSION S29506
n pilynlvsanfrhiflatlaclcpvwrrrrkrpafsrkadsvssnhflssnatretly
    Class B 28. SUBSTANCE-P RECEPTOR (SPR) (NK-1 RECEPTOR) (NK-1R). ACCESSION P25103
npiiycclndrfrlgfkhafrccpfisagdyeglemkstrylqtqgsvykvsrlettistvvgaheeepedgpkatpssldltsncssrsd
sktmtesfsfssnvls
    Class B 29. vasopressin receptor type 2 [Homo sapiens]. ACCESSION AAD16444
npwiyasfsssvsselrsllccargrtppslgpqdescttassslakdtss
    Class B 30. thyrotropin-releasing hormone receptor - human. ACCESSION JN0708
npviynlmsqkfraafrklcnckqkptekpanysvalnysvikesdhfstelddifvtdtylsafkvsfddtclasevsfsqs
    Class B 31. oxytocin receptor - human. ACCESSION A55493
npwiymlftghlfhelvqrflccsasylkgrrlgetsaskksnsssfvlshrsssqrscsqpsta
    Class B Figure 2
page 4

32. neuromedin U receptor 1 [Homo sapiens]. ACCESSION AAG24793
npvlyslmssrfretfqealclgacchrlrprhsshslsrmttgstlcdvgslgswvhplagndgpeaqqetdps
Class B 33. gastrin receptor. ACCESSION AAC37528
nplvycfmhrrfrqacletcarccprpprarpralpdedpptpsiaslsrlsyttistlgpg
Class B 34. galanin receptor 3 [Homo sapiens]. ACCESSION 10879541
nplvyalasrhfrarfrrlwpcgrrrrhrarralrrvrpassgppgcpgdarpsgrllagggqgpepregpvhggeaargpe
Class A 35. edg-1 - human. ACCESSION A35300
npiiytltnkemrrafirimscckcpsgdsagkfkrpiiagmefsrsksdnsshpqkdegdnpetimssgnvnsss
Class A 36. central cannabinoid receptor [Homo sapiens]. ACCESSION NP_057167
npiiyalrskdlrhafrsmfpscegtaqpldnsmgdsdclhkhannaasvhraaescikstvkiakvtmsvstdtsaeal
Class A 37. delta opioid receptor - human. ACCESSION I38532
npvlyafldenfkrcfrqlcrkpcgrpdpssfsrpreatarervtactpsdgpgggraa
Class A 38. proteinase activated receptor 2 (PAR-2) human. ACCESSION P55085
dpfvyyfvshdfrdhaknallcrsvrtvkqmqvsltskkhsrksssyssssttvktsy
Class B 39. vasopressive intestinal peptide receptor (VIPR) rat. ACCESSION NM_012685
NGEVQAELRRKWRRWHLQGVLGWSSKSQHPWGGSNGATCSTQVSMLTRVSPSARR
SSSFQAEVSLV
Class B

|    | A | B | C |
|----|---|---|---|
| 1  | GPCR Agonist | Generic Name | Brand Name |
| 2  | 5-HT | | |
| 3  | 5-HT-1B/1D | Zolmitriptan | Zomig |
| 4  |  | Rizatriptan | Maxalt |
| 5  |  | Eletriptan | Relpax |
| 6  |  | Trazodone | Desyrel |
| 7  | 5-HT-1D | Sumatriptan | Imitrex (P) |
| 8  |  | Naratriptan | Amerge |
| 9  |  | Almotriptan | Axert |
| 10 | 5-HT-1B/1A | Frovatriptan | Frova |
| 11 |  |  |  |
| 12 | 5-HT-1A | Buspirone | BuSpar |
| 13 | 5-HT-1A | Buspirone | Generic |
| 14 | 5-HT-1A | Ziprasidone | Geodon |
| 15 |  |  |  |
| 16 | 5-HT-4 | Tegaserod | Zelnorm |
| 17 | 5-HT-4 | Mosapride | Gasmotin |
| 18 | 5-HT-4 | Cisapride | Propulsid |
| 19 |  |  |  |
| 20 | 5-HT-2A/2C | Clozapine | Clozaril |
| 21 |  |  |  |
| 22 | 5-HT-2 / Dopa D1 | Femoldopam | Corlopam |
| 23 |  |  |  |
| 24 | 5-HT/ Opioid u | Tramadol | Ultram |
| 25 | 5-HT/ Opioid u | Tramadol | Ultracet |
| 26 | 5-HT/ Opioid u | Tramadol | Generic |
| 27 |  |  |  |
| 28 | Opioid | | |
| 29 | Opioid | Codeine | Generic |
| 30 |  | Hydrocodone | Generic |
| 31 |  | Hydromorphone | Dilaudid |
| 32 |  | Levorphanol | Levo-Dromoran |
| 33 |  | Morphine | MS Contin |
| 34 |  | Morphine | Generic |
| 35 |  | Oxycodone | OxyContin |
| 36 |  | Oxycodone/APAP | Generic |
| 37 |  | Oxymorphone | Numorphan |
| 38 |  | Alfentanil | Alfenta |
| 39 |  | Fentanyl | Duragesic |
| 40 |  | Fentanyl | Sublimaze |
| 41 |  | Meperidine | Demerol |
| 42 |  | Sufentanil | Sufenta |
| 43 |  | Levomethadyl | Orlaam |
| 44 |  | Methadone | Dolophine |
| 45 |  | Propoxyphene | Darvon |
| 46 |  | Buprenorphine | Transtec |
| 47 |  | Remifentanil | Ultiva |
| 48 |  |  |  |
| 49 | 5-HT/ Opioid u | Tramadol | Ultram |
| 50 | 5-HT/ Opioid u | Tramadol | Ultracet |
| 51 | 5-HT/ Opioid u | Tramadol | Generic |
| 52 |  | Fig 3, page 1 of 3 | |

|   | A | B | C |
|---|---|---|---|
| 1 | GPCR Agonist | Generic Name | Brand Name |
| 53 | ADO | | |
| 54 | ADO (mixed) | Adenosine | Adenocard |
| 55 | | Adenosine | Adenoscan |
| 56 | | | |
| 57 | Adrenoceptor | | |
| 58 | Adrenoceptor | Methylphenidate | Generic |
| 59 | Beta (mixed) | Isoproterenol | Isuprel |
| 60 | | Ephedrine | Generic |
| 61 | | Mephentermine | Wyamine |
| 62 | Beta-1 | Norepinephrine | Levophed |
| 63 | | | |
| 64 | Beta-2 | Salmeterol | Serevent |
| 65 | | Salmeterol/ fluticasone | Advair |
| 66 | | Albuterol, Aerosol | Generic |
| 67 | | Albuterol, Sulfate | Generic |
| 68 | | Albuterol | Proventil |
| 69 | | Bitolterol | Tornalate |
| 70 | | Isoetharine | Isoetharine |
| 71 | | Metaproterenol | Alupent |
| 72 | | Pirbuterol | Maxair |
| 73 | | Formoterol | Foradil |
| 74 | | Formoterol, | Oxis |
| 75 | | Albuterol | Ventolin HFA |
| 76 | | Bambuterol | Bambec |
| 77 | | Salbutamol | Inspiryl Turbuhaler |
| 78 | | Terbutaline | Brethine |
| 79 | | Terbutaline | Terbutaline |
| 80 | H1 (-) / Beta-2 (+) | loratadine/ pseudoephedrine | Claritin-D |
| 81 | H1 (-) / Beta-2 (+) | Fexofenadine/ pseudoephedrine | Allegra-D |
| 82 | | Terbutaline | Brethine |
| 83 | Alpha-Beta (mixed) | Metaraminol | Aramine |
| 84 | | Epinephrine | Generic |
| 85 | Alpha (mixed) | Methoxamine | Vasoxyl |
| 86 | | Phenyephrine | Neo-Synephrine |
| 87 | Alpha-1 | Modafinil | Provigil |
| 88 | | Midodrine | ProAmatine |
| 89 | | | |
| 90 | Alpha-2 | Guanfacine | Tenex |
| 91 | | Tizanidine SR | Sirdalud CR |
| 92 | | Moxonidine | Physiotens |
| 93 | | Dexmedetomidine | Precedex |
| 94 | | Brimonidine | Alphagen |
| 95 | | Apraclonidine | Iopidine |
| 96 | | Fig 3, page 2 of 3 | |

|     | A | B | C |
|-----|---|---|---|
| 1   | GPCR Agonist | Generic Name | Brand Name |
| 97  | | | |
| 98  | Acetylcholine | Bethanechol | Generic |
| 99  | Muscarinic AC | Pilocarpine | Salagen |
| 100 | Muscarinic AC | Levetiracetam | Keppra |
| 101 | | | |
| 102 | Dopamine | | |
| 103 | Dopamine (mixed) | Dopamine | Intropin |
| 104 | D1 | Femoldopam | Corlopam |
| 105 | D2 | Apomorphine | Ixense |
| 106 | D2/D3 | Ropinirole | Requip |
| 107 | D2/D3 | Pramipexole | Mirapex |
| 108 | D2/D3 | Amisulpride | Solian |
| 109 | D2 Type | Bromocriptine | Parlodel |
| 110 | D1/D2 | Pergolide | Permax |
| 111 | | | |
| 112 | Prostaglandin F2a (PG F2a) | Latanoprost | Xalatan |
| 113 | Prostaglandin F2a (PG F2a) | Unknown | Travatan |
| 114 | Prostaglandin E1 (PGE1) | Alprostadil | Befar |
| 115 | | | |
| 116 | Gonadotropin-releasing hormone (GnRH) | LHRH agonist | TRELSTAR LA |
| 117 | GnRH | Leuprolide | Lupron Depot |
| 118 | | | |
| 119 | | | |
| 120 | Calcitonin | Calcitonin | |
| 121 | | Fig 3, page 3 of 3 | |

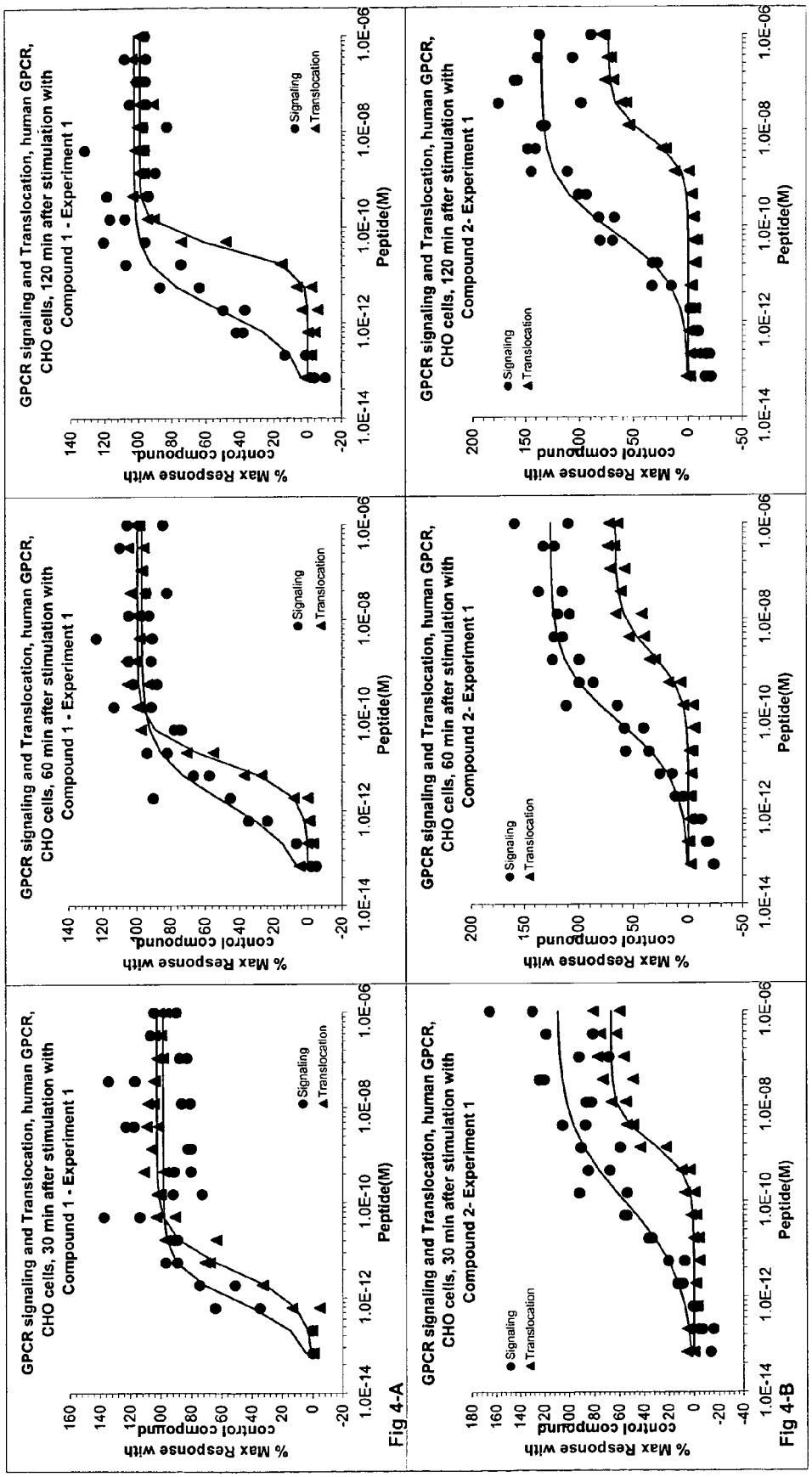
Fig 4-A
Fig 4-B

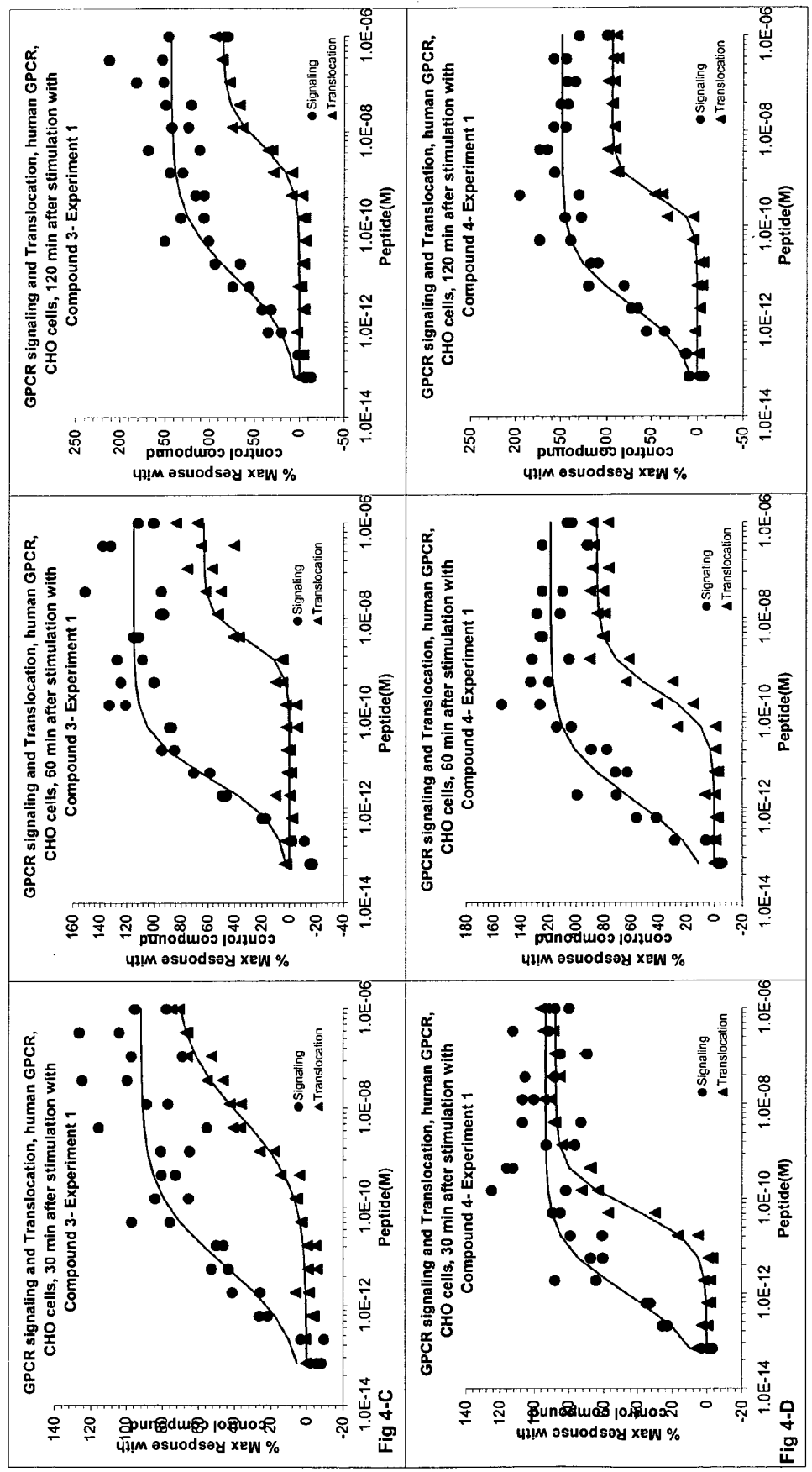

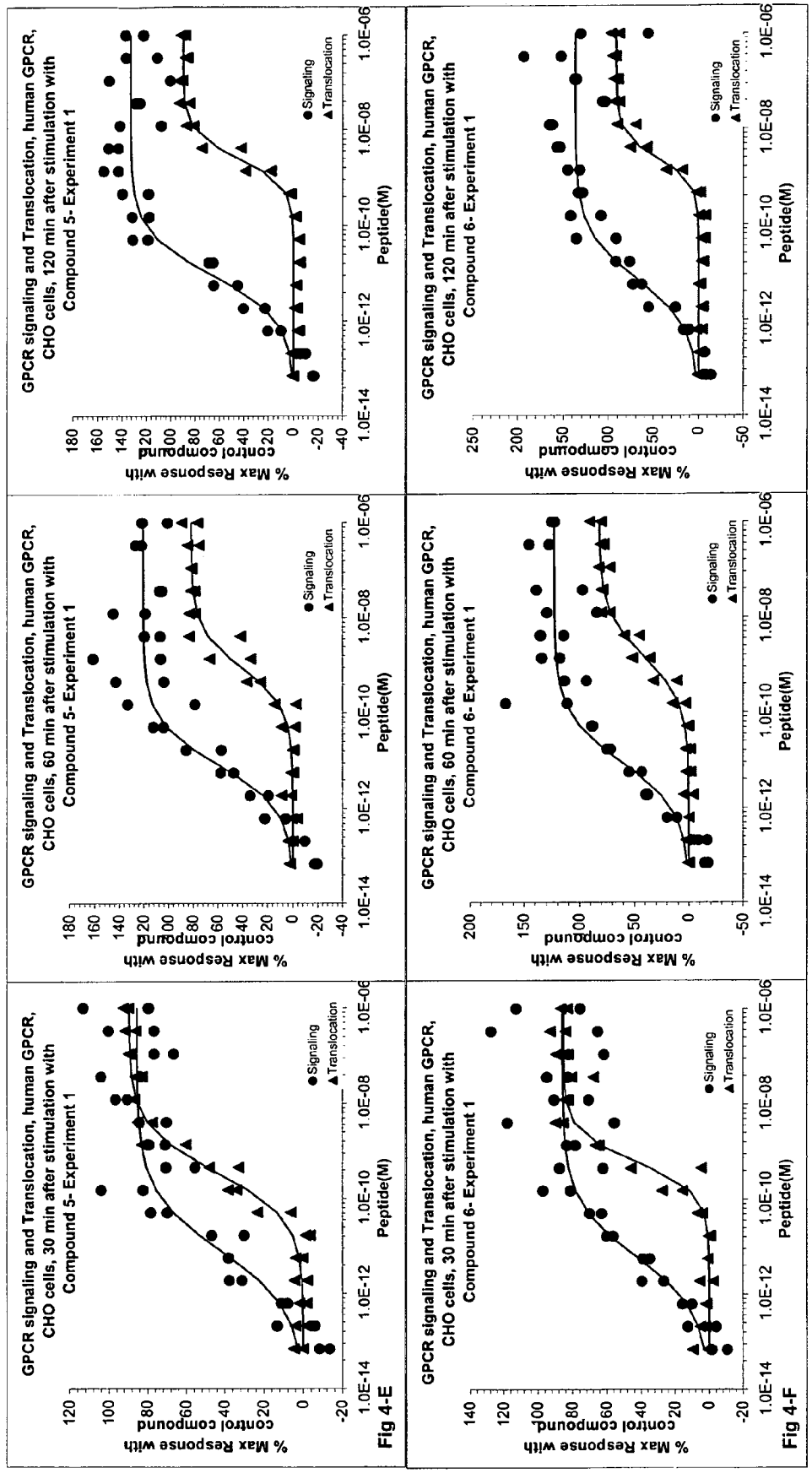
Fig 4-E
Fig 4-F

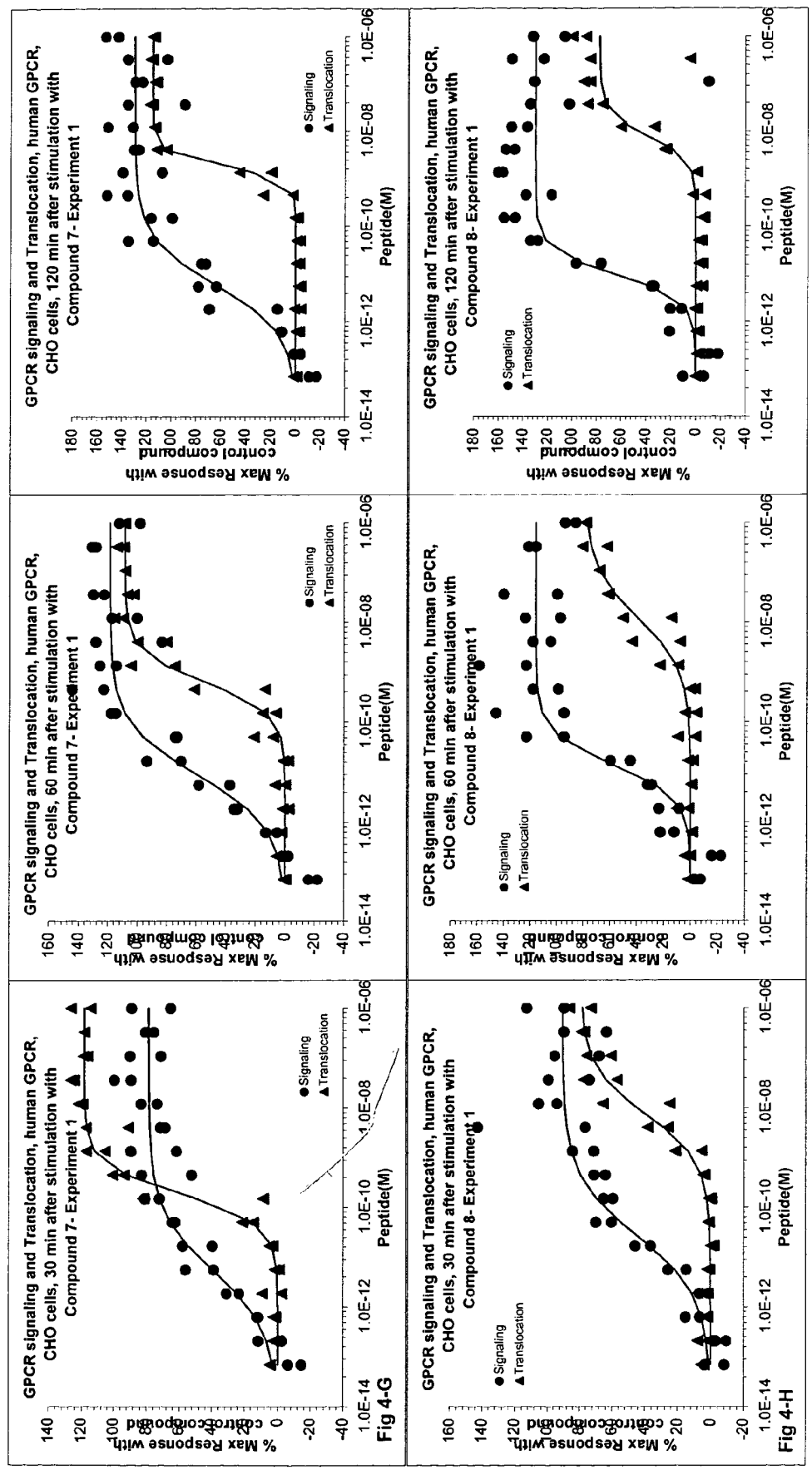
Fig 4-G
Fig 4-H

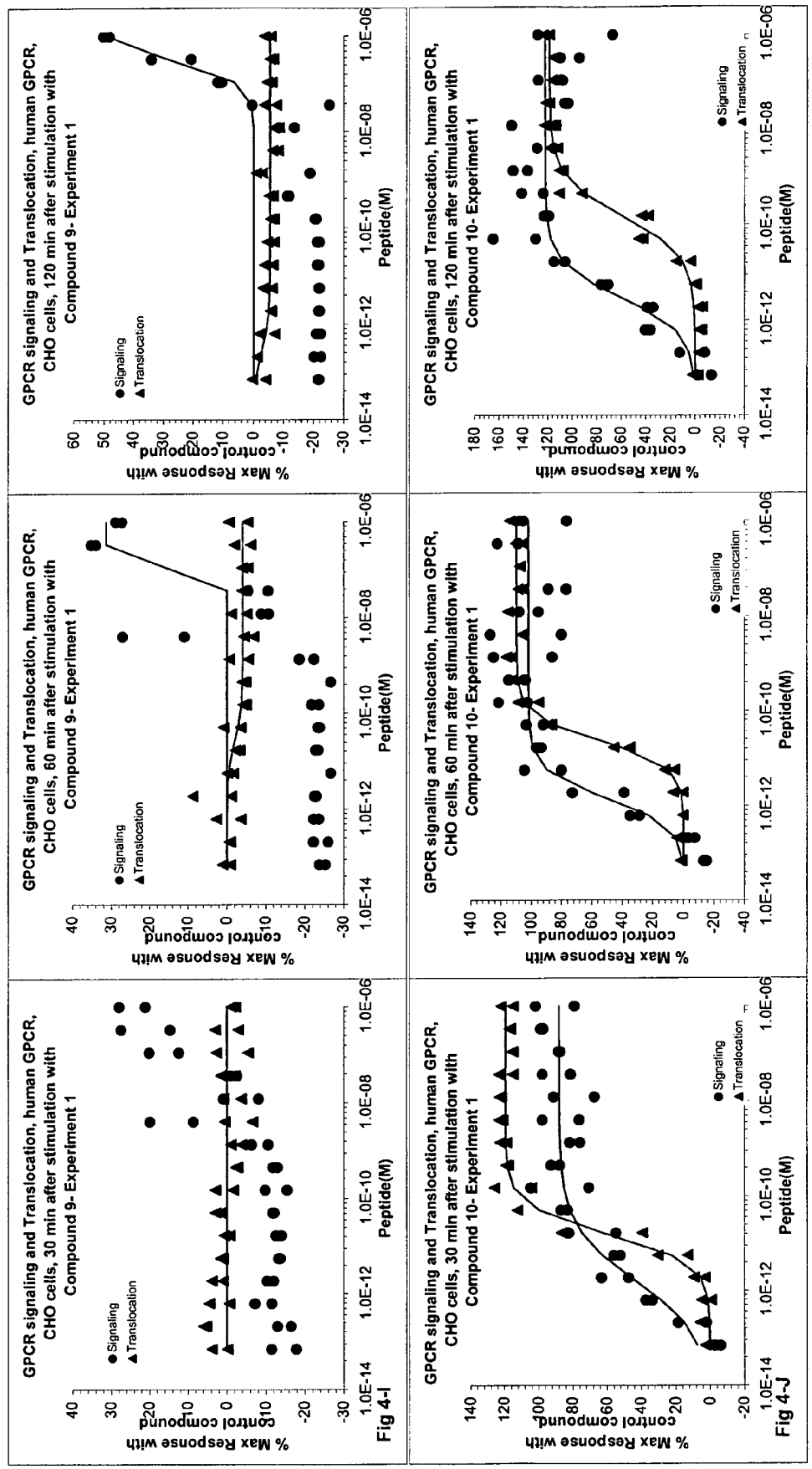
Fig 4-I
Fig 4-J

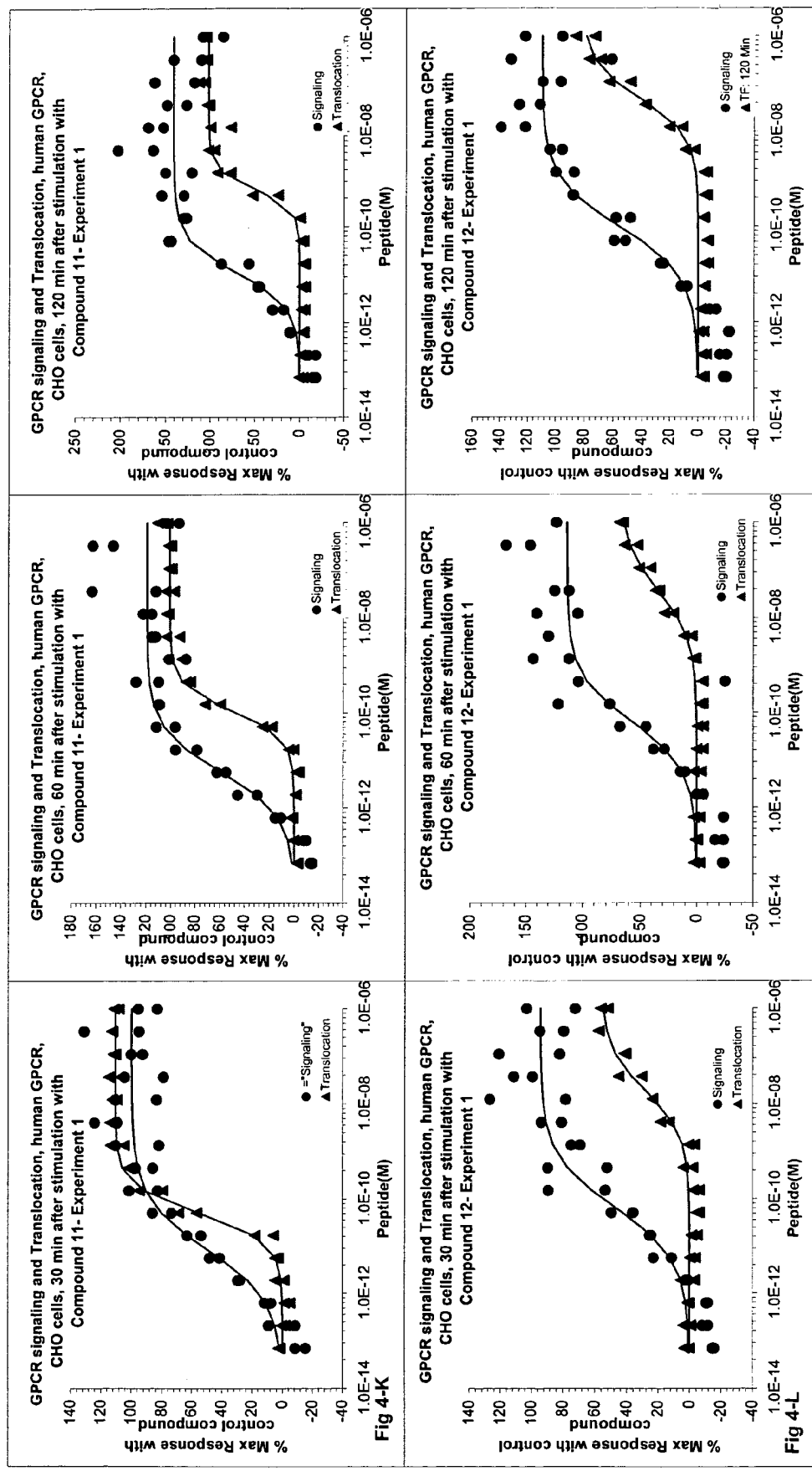

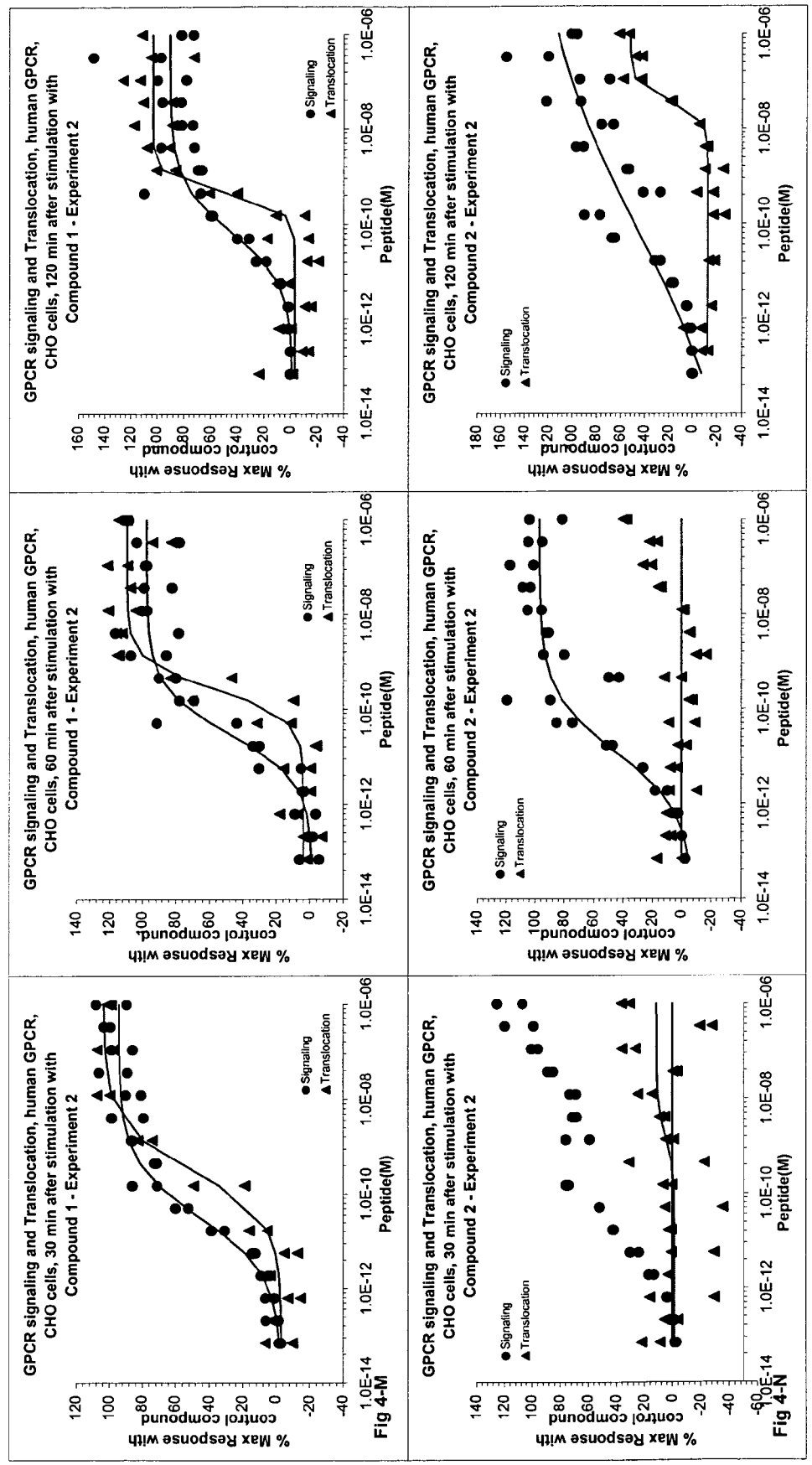

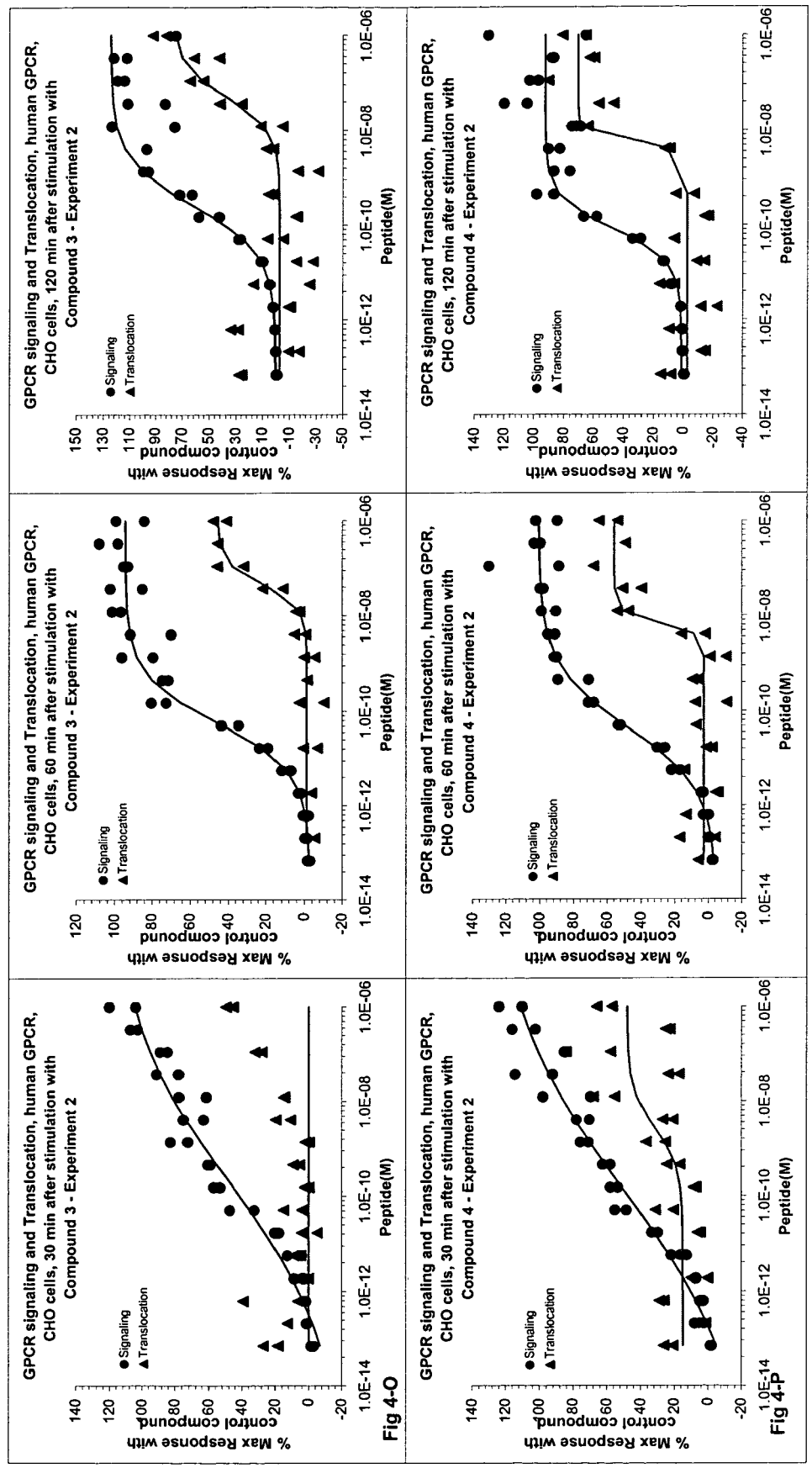
Fig 4-O
Fig 4-P

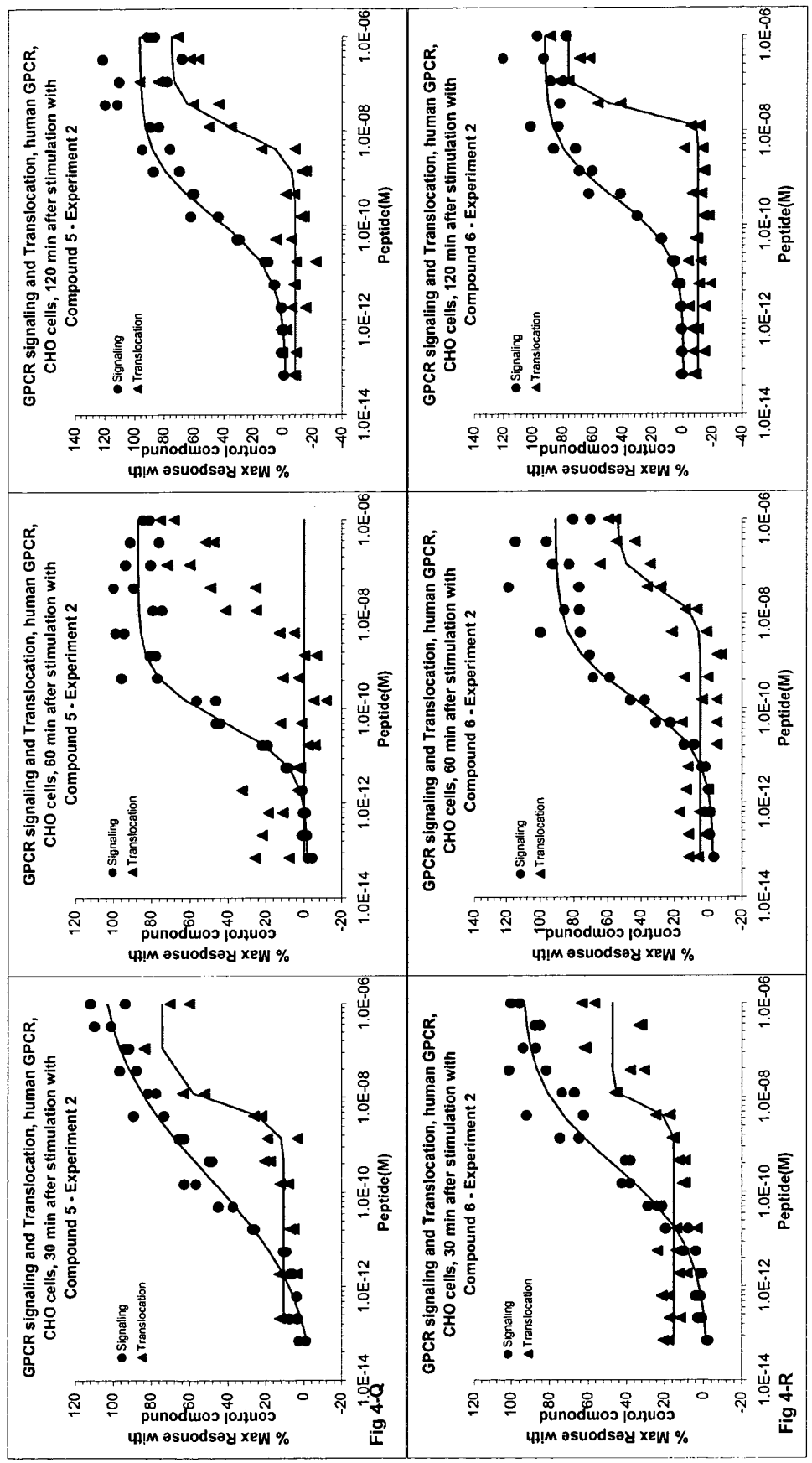

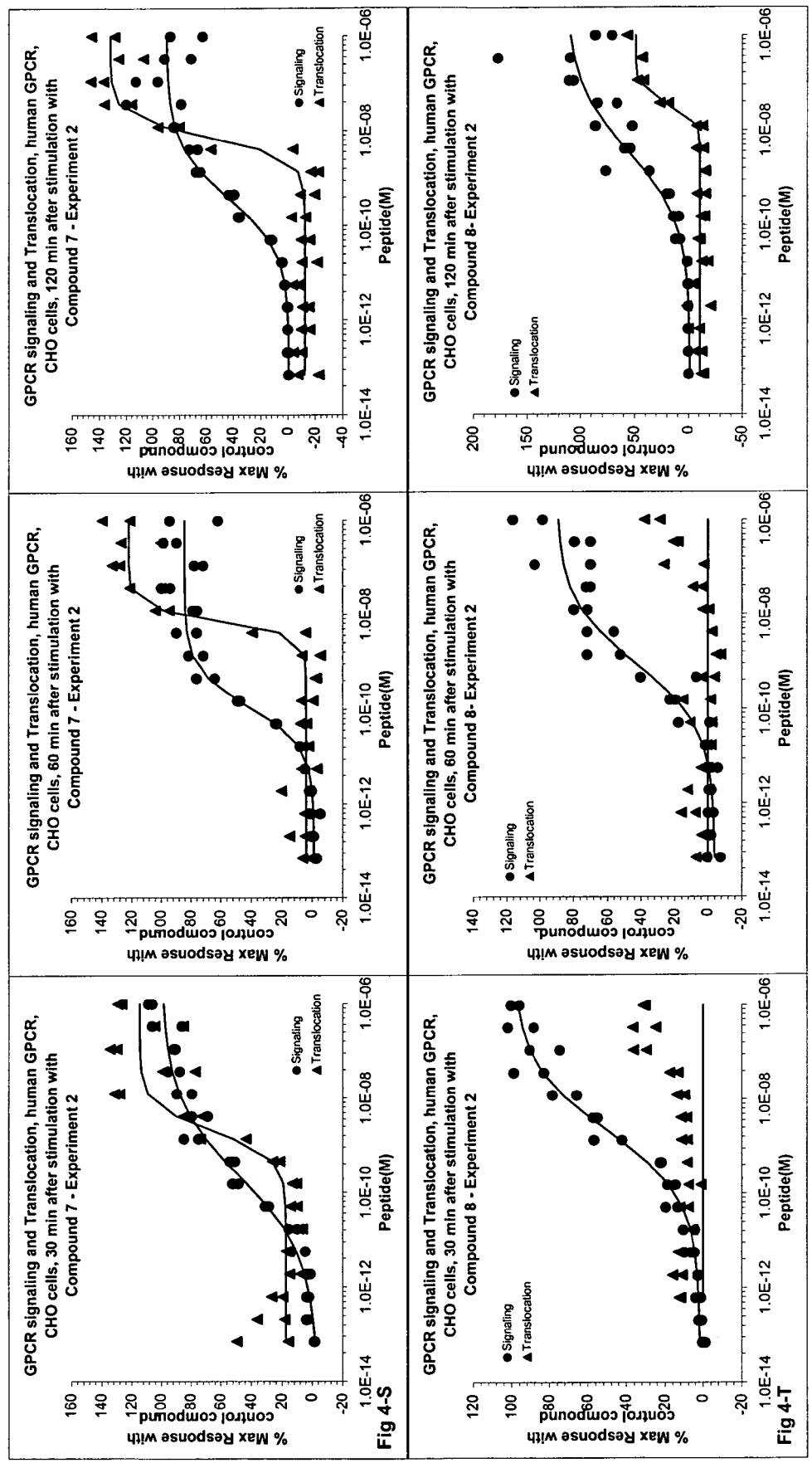

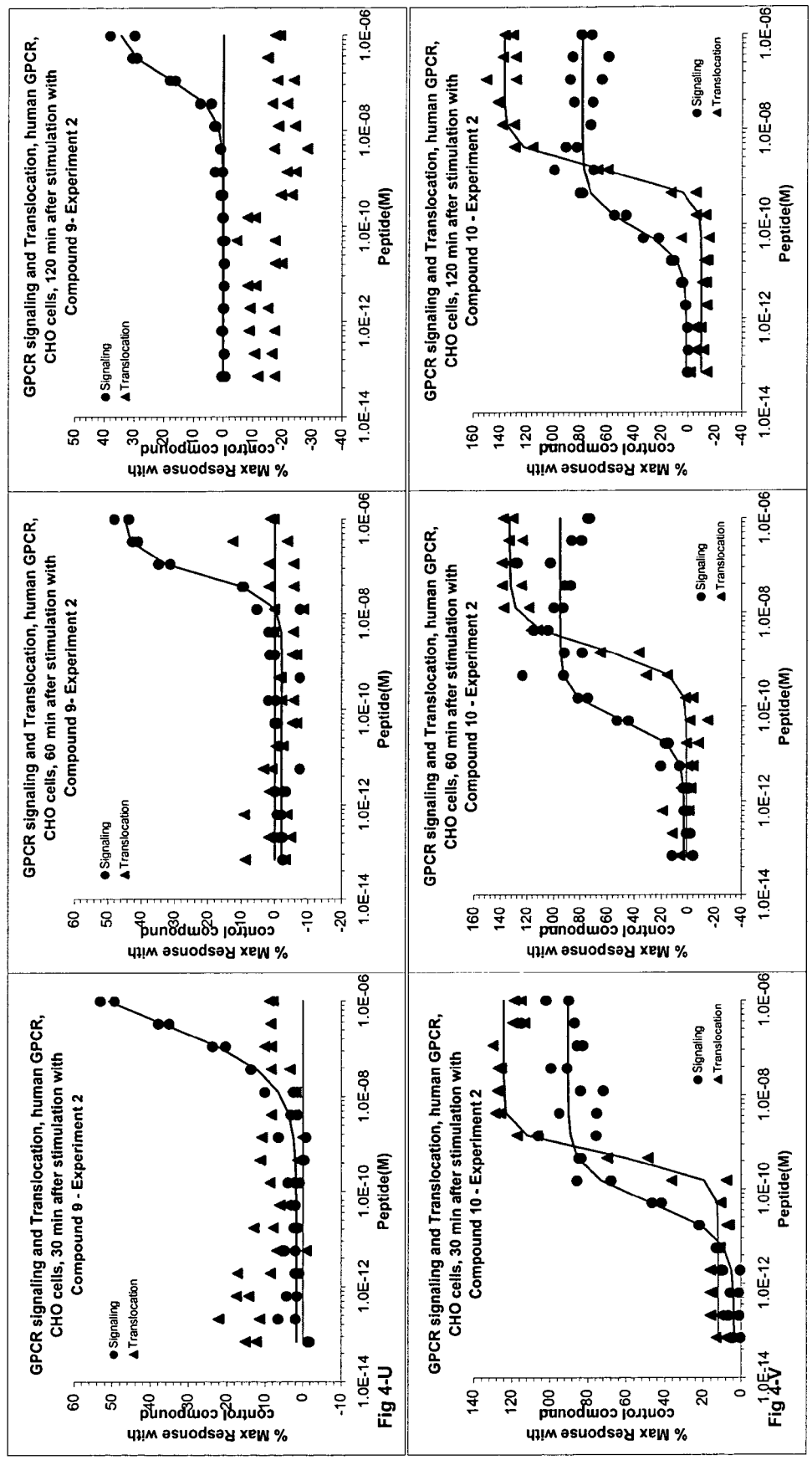

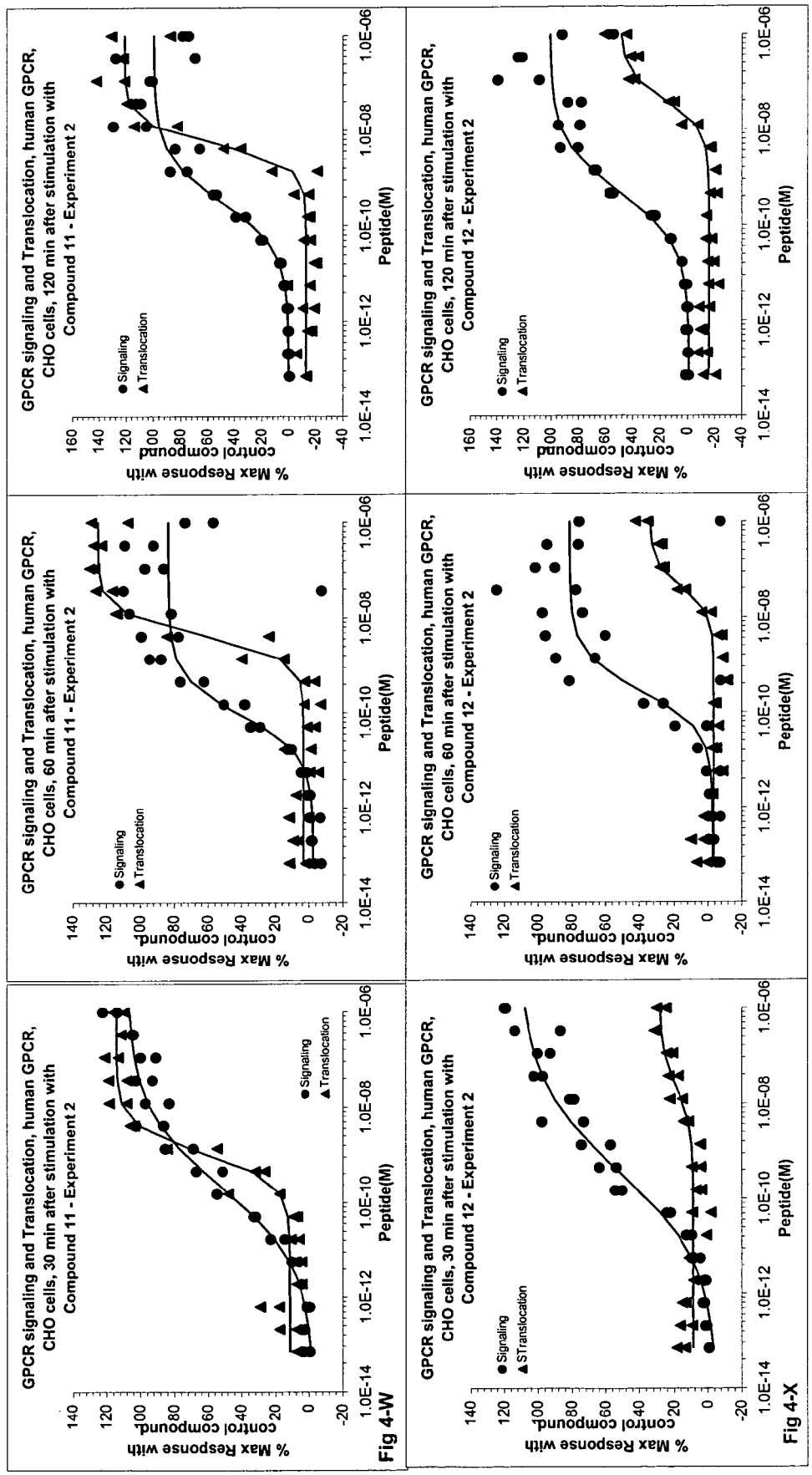
Fig 4-W
Fig 4-X

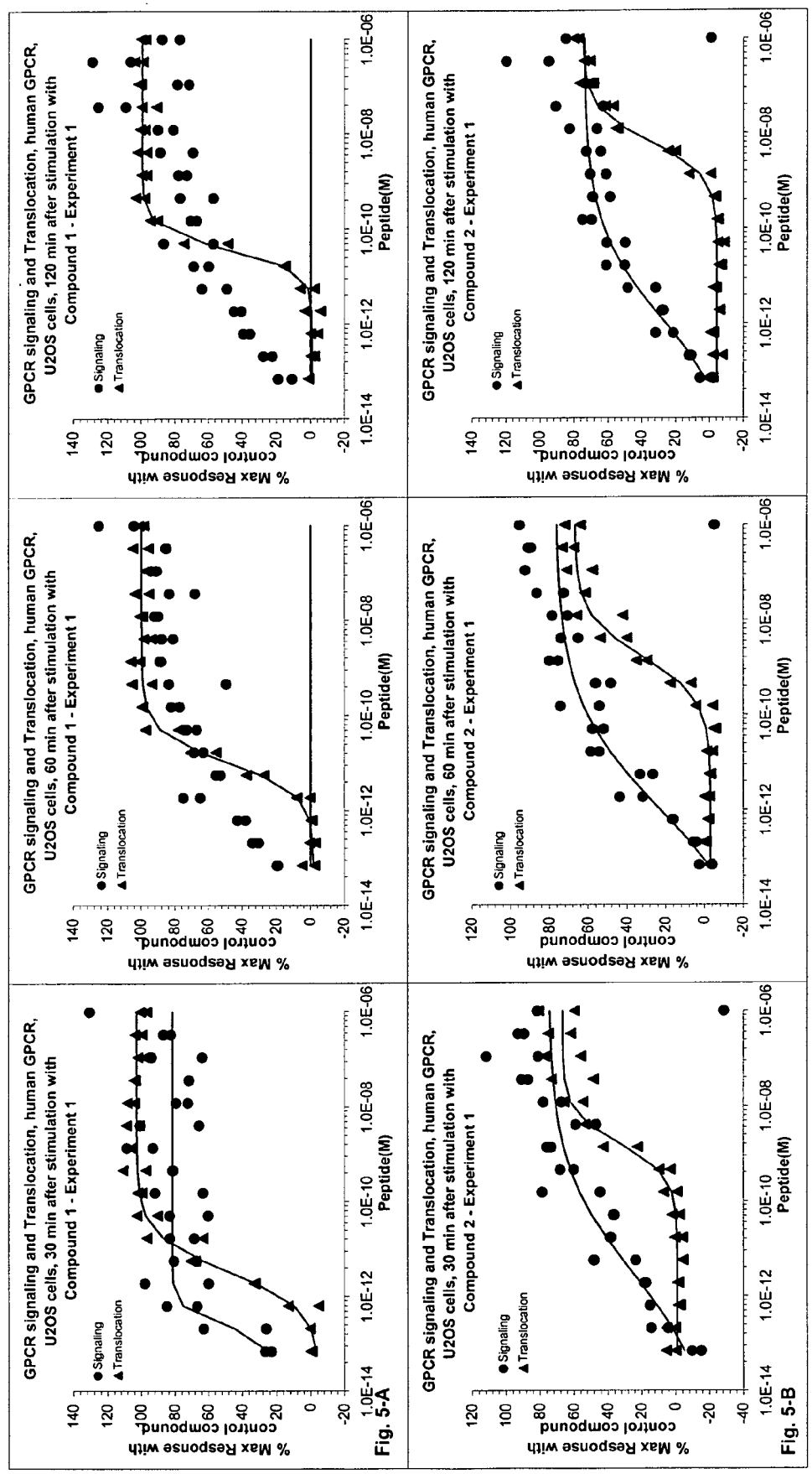
Fig. 5-A
Fig. 5-B

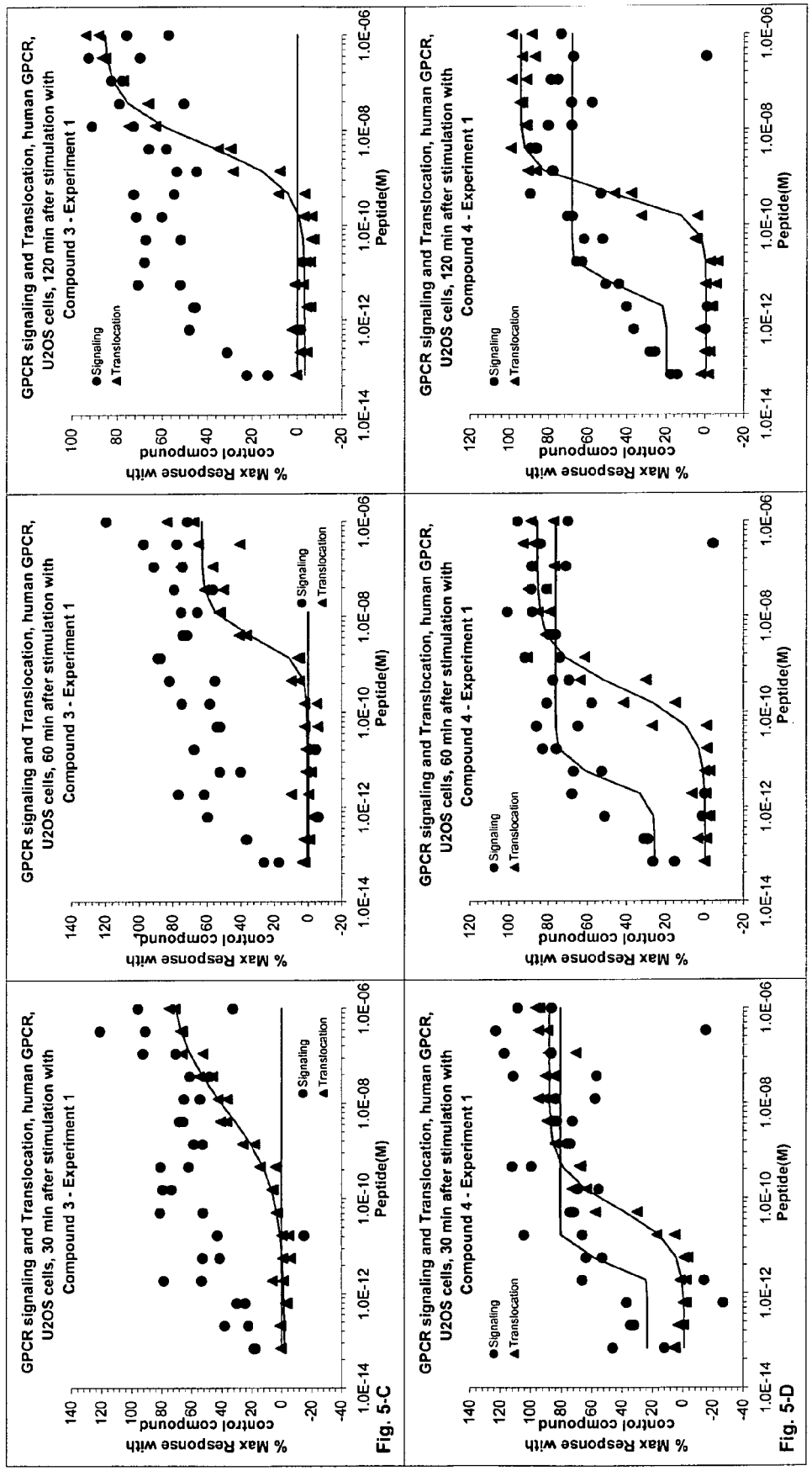
Fig. 5-C
Fig. 5-D

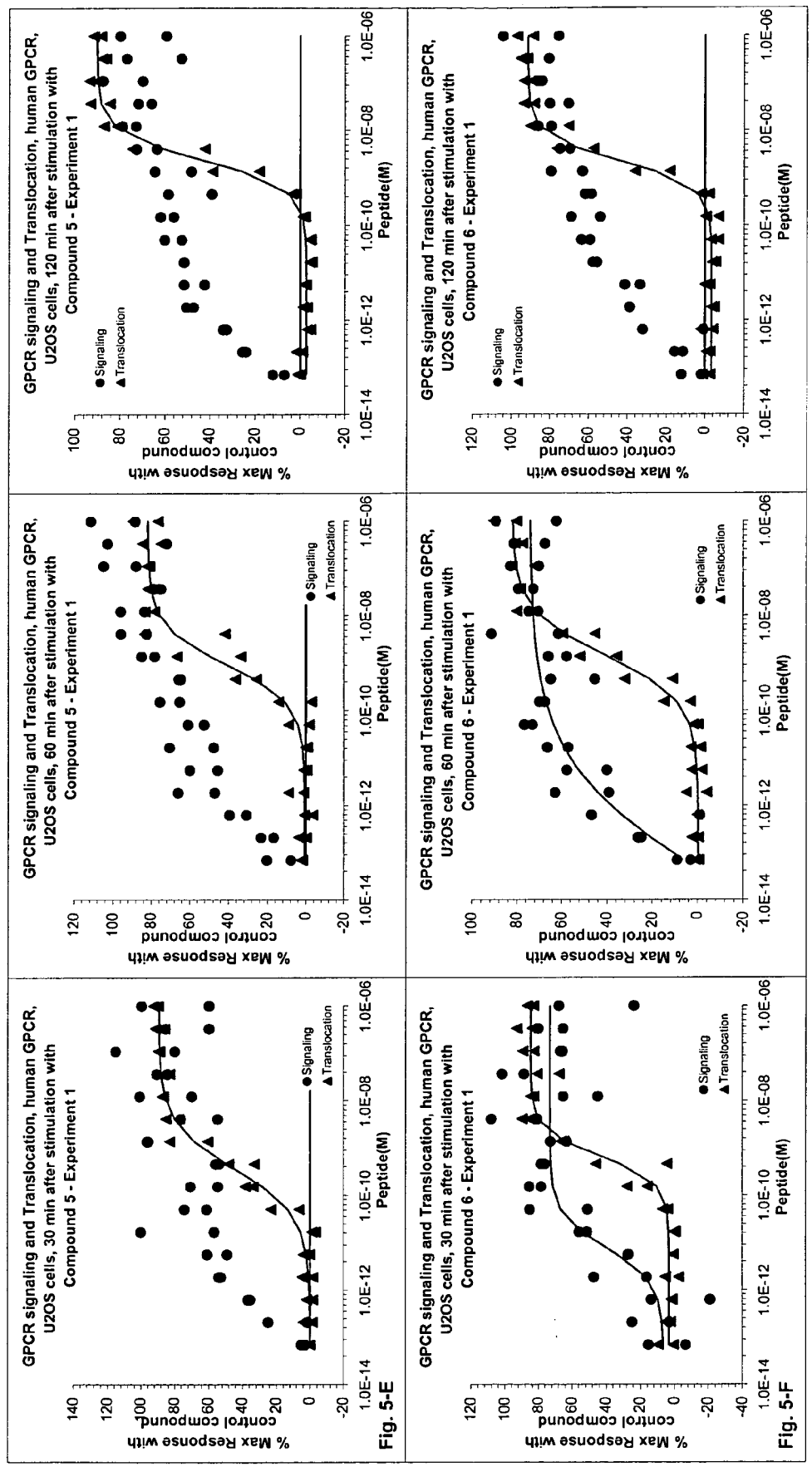
Fig. 5-E
Fig. 5-F

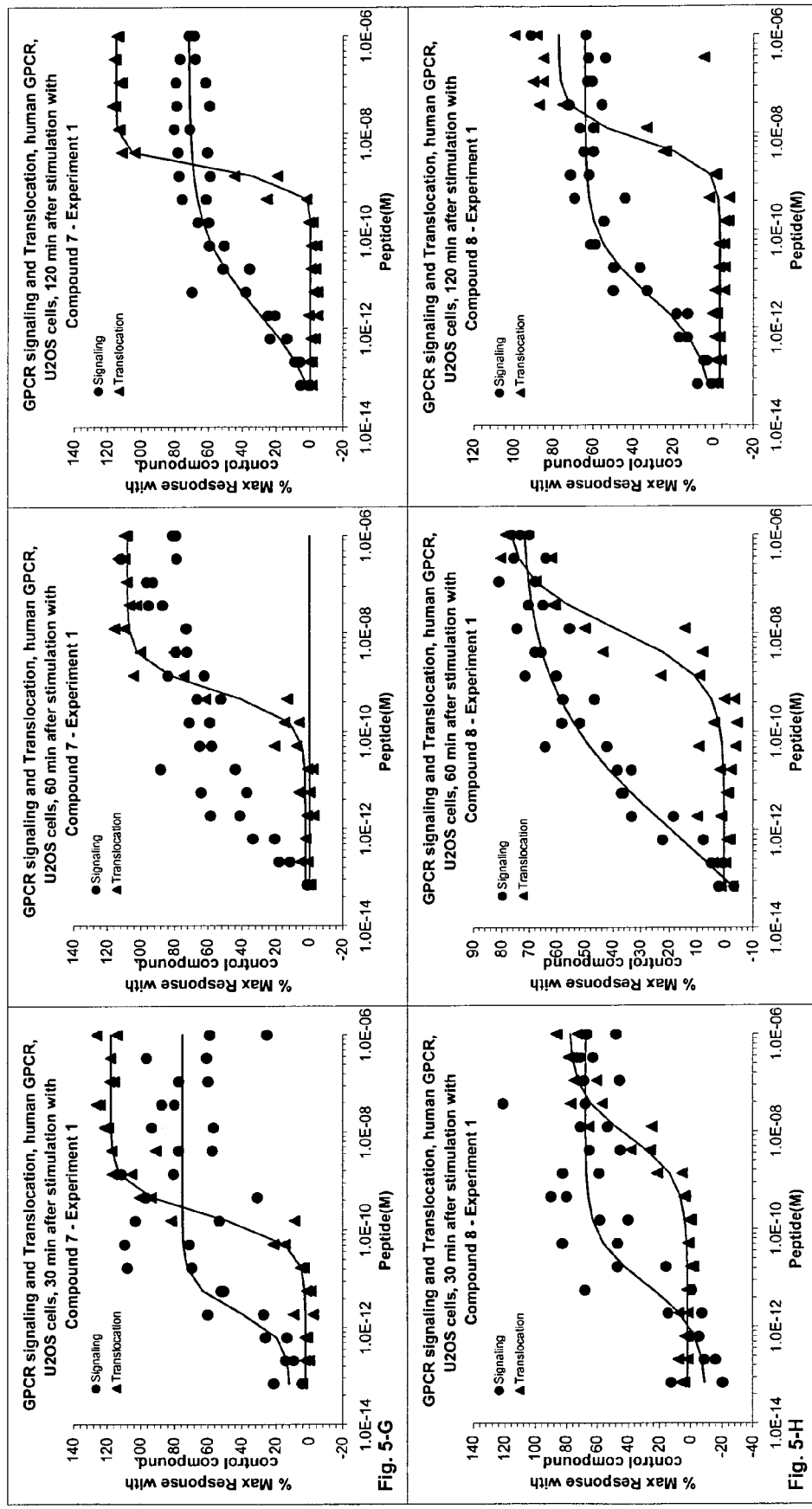

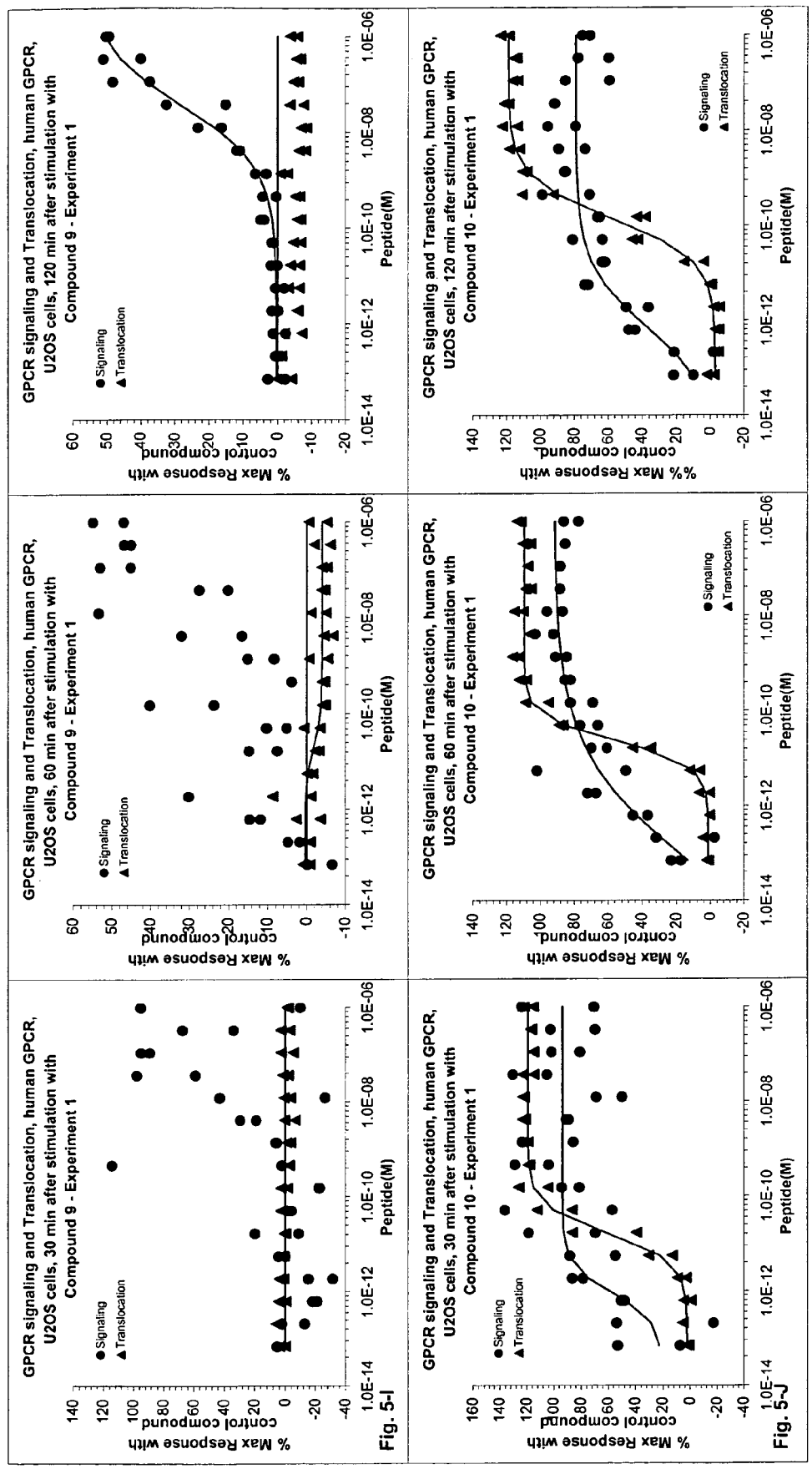
Fig. 5-I
Fig. 5-J

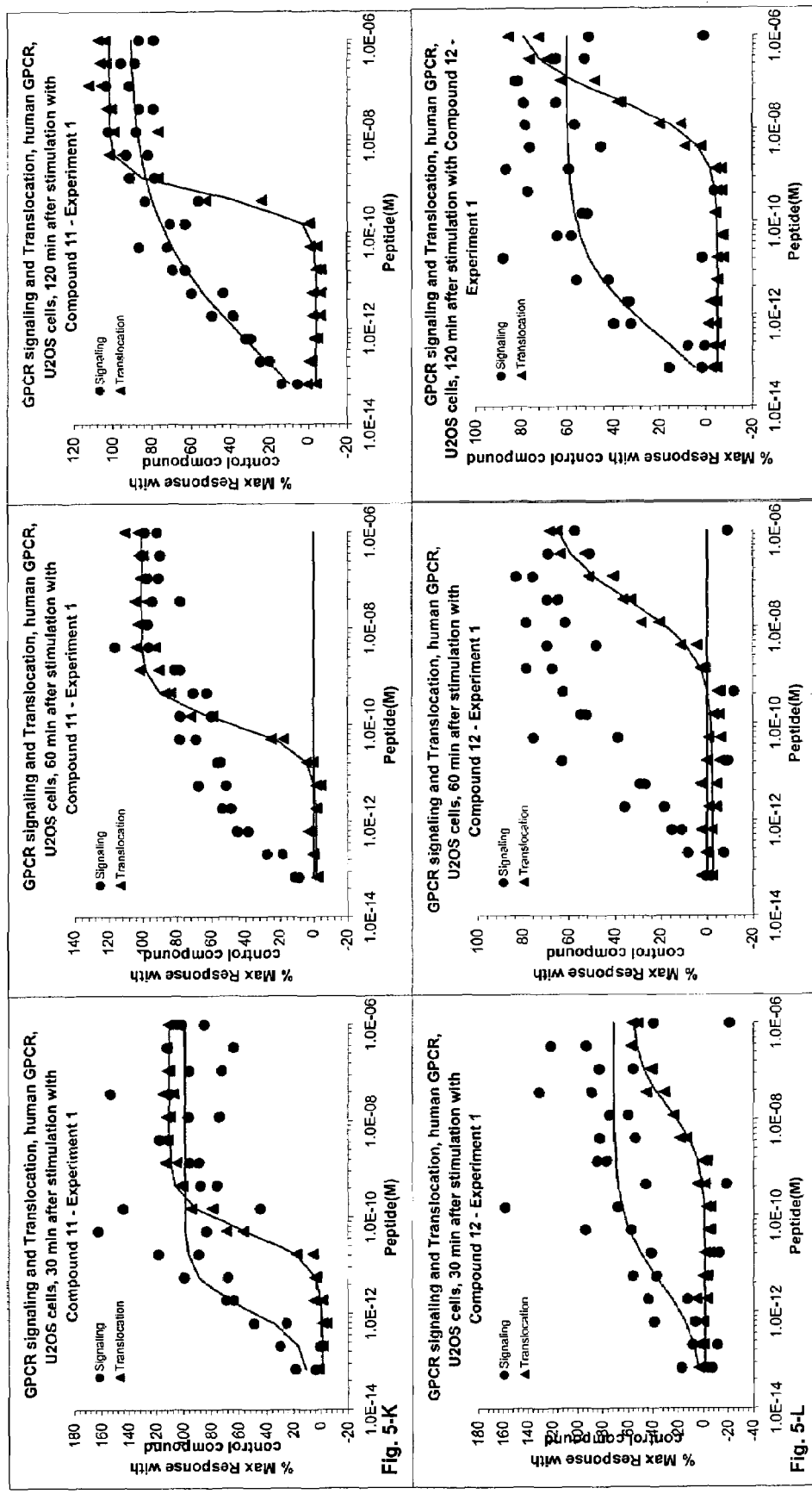
Fig. 5-K
Fig. 5-L

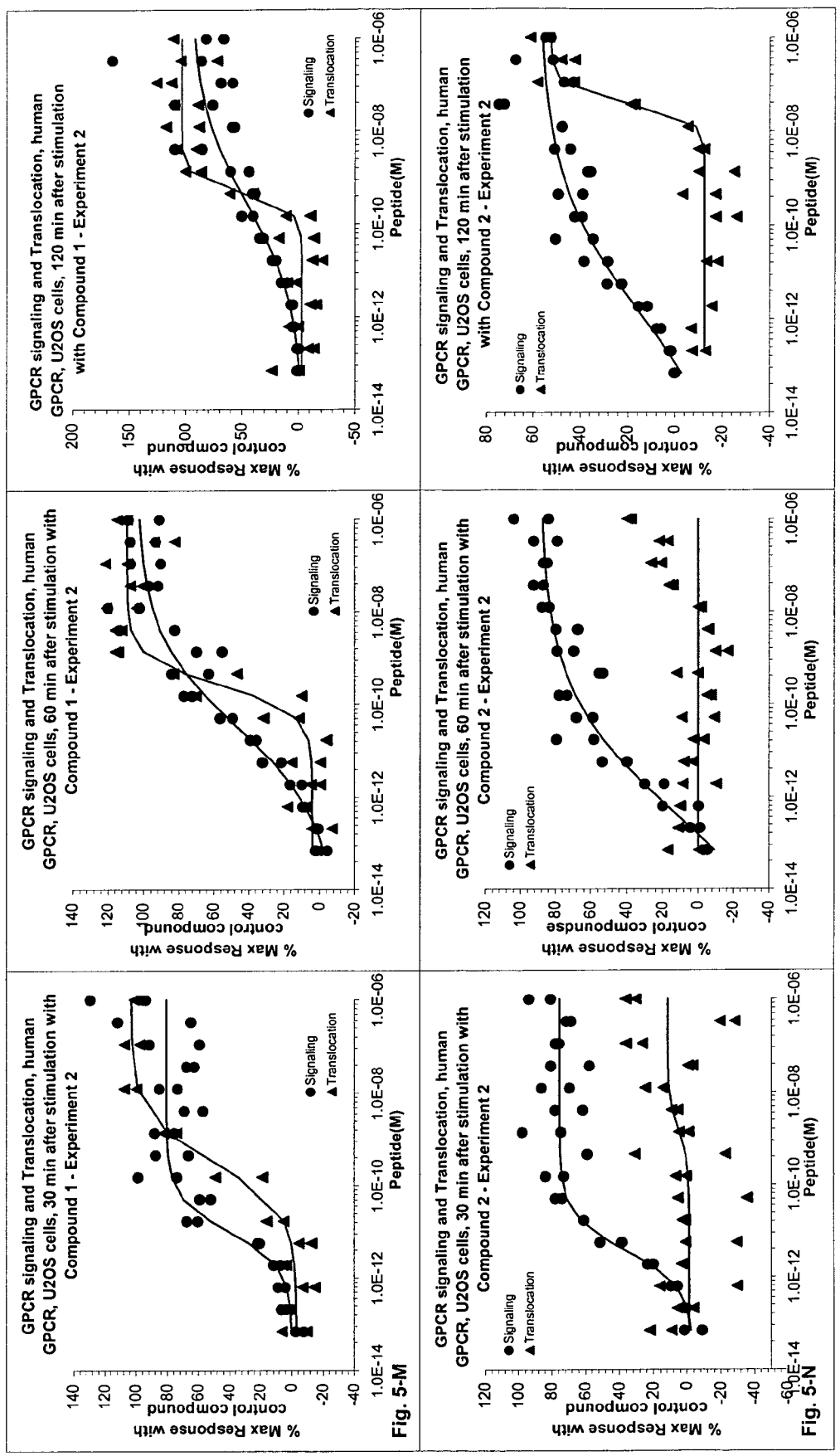

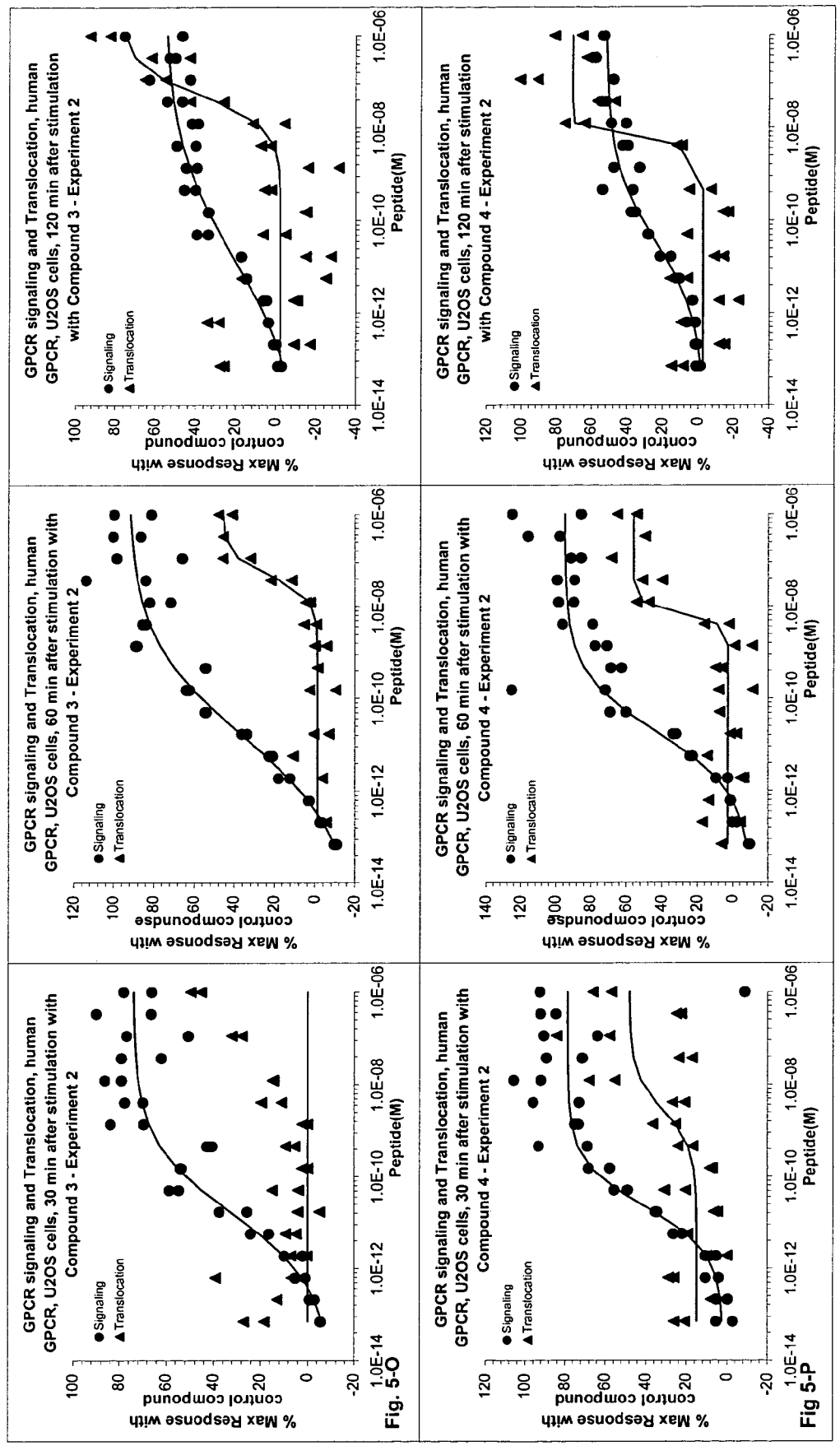

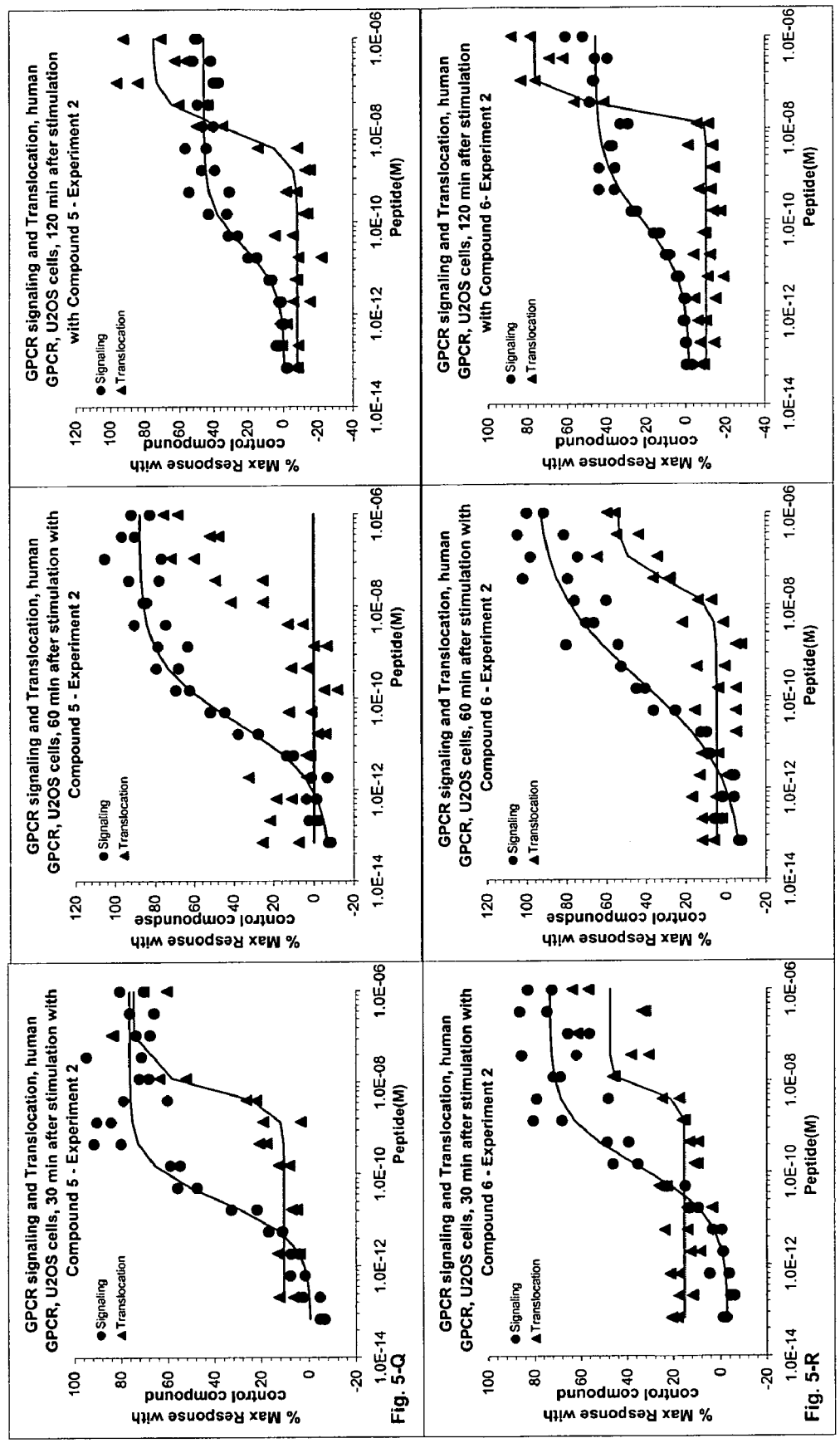

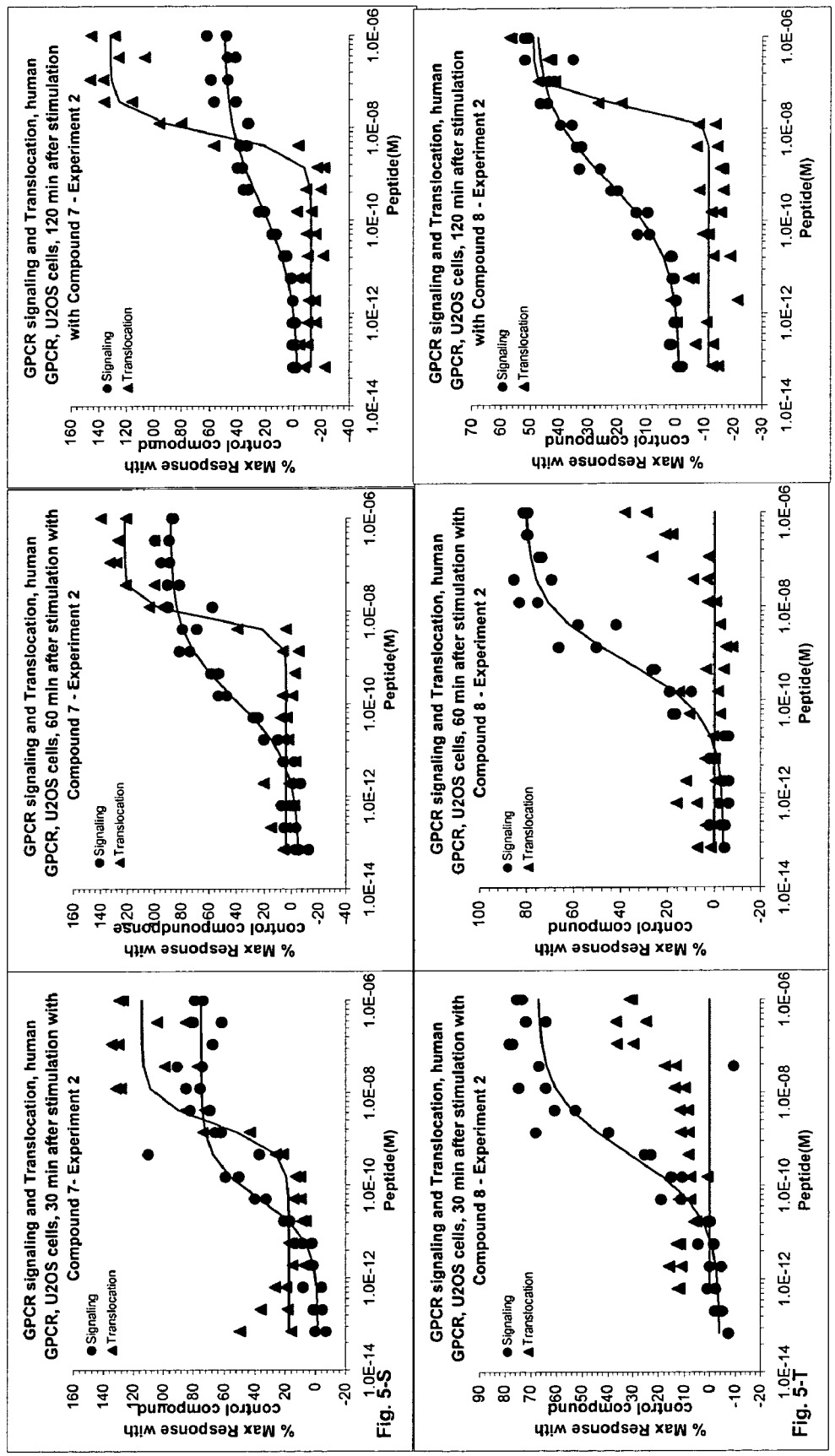
Fig. 5-S
Fig. 5-T

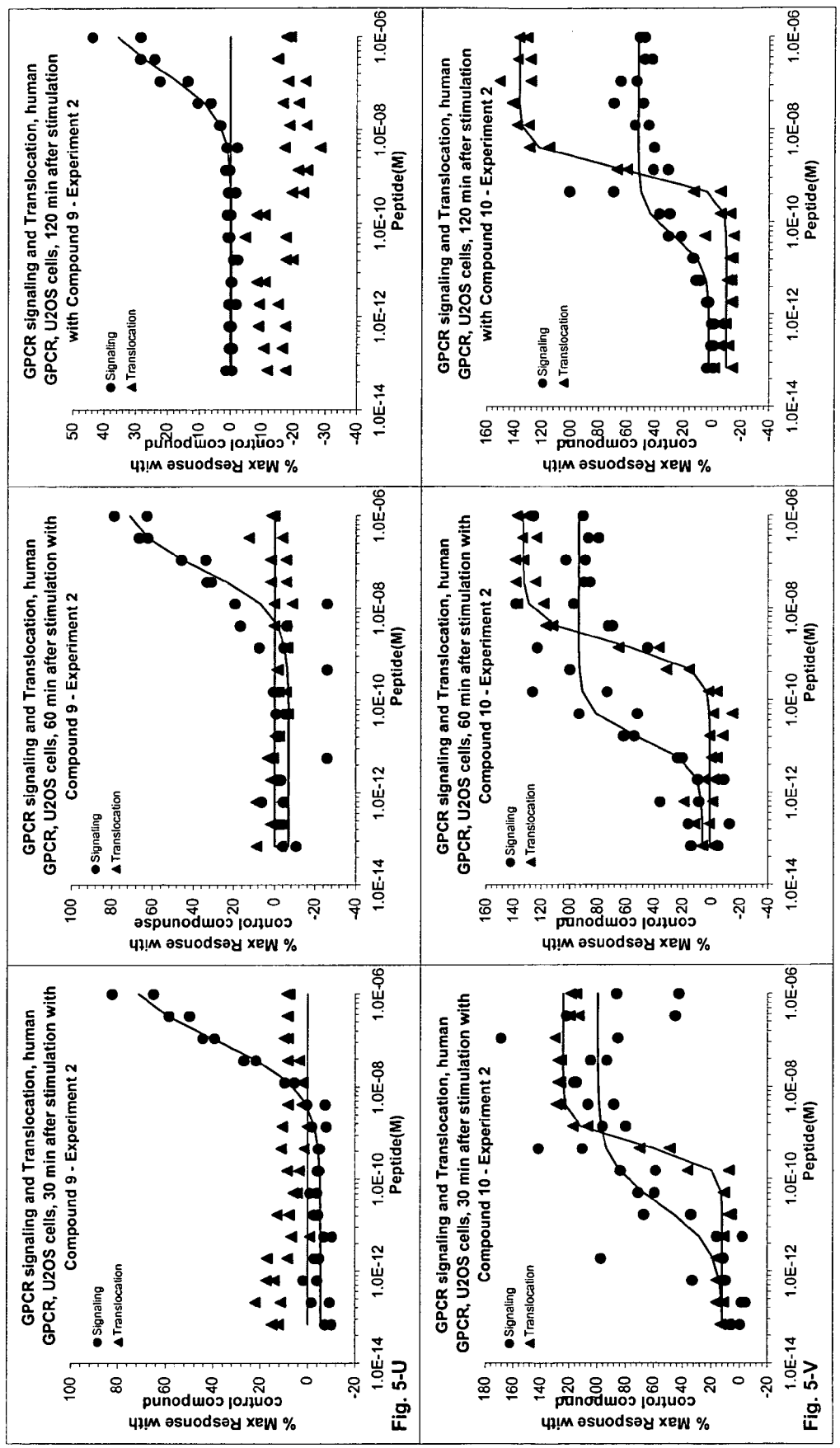
Fig. 5-U
Fig. 5-V

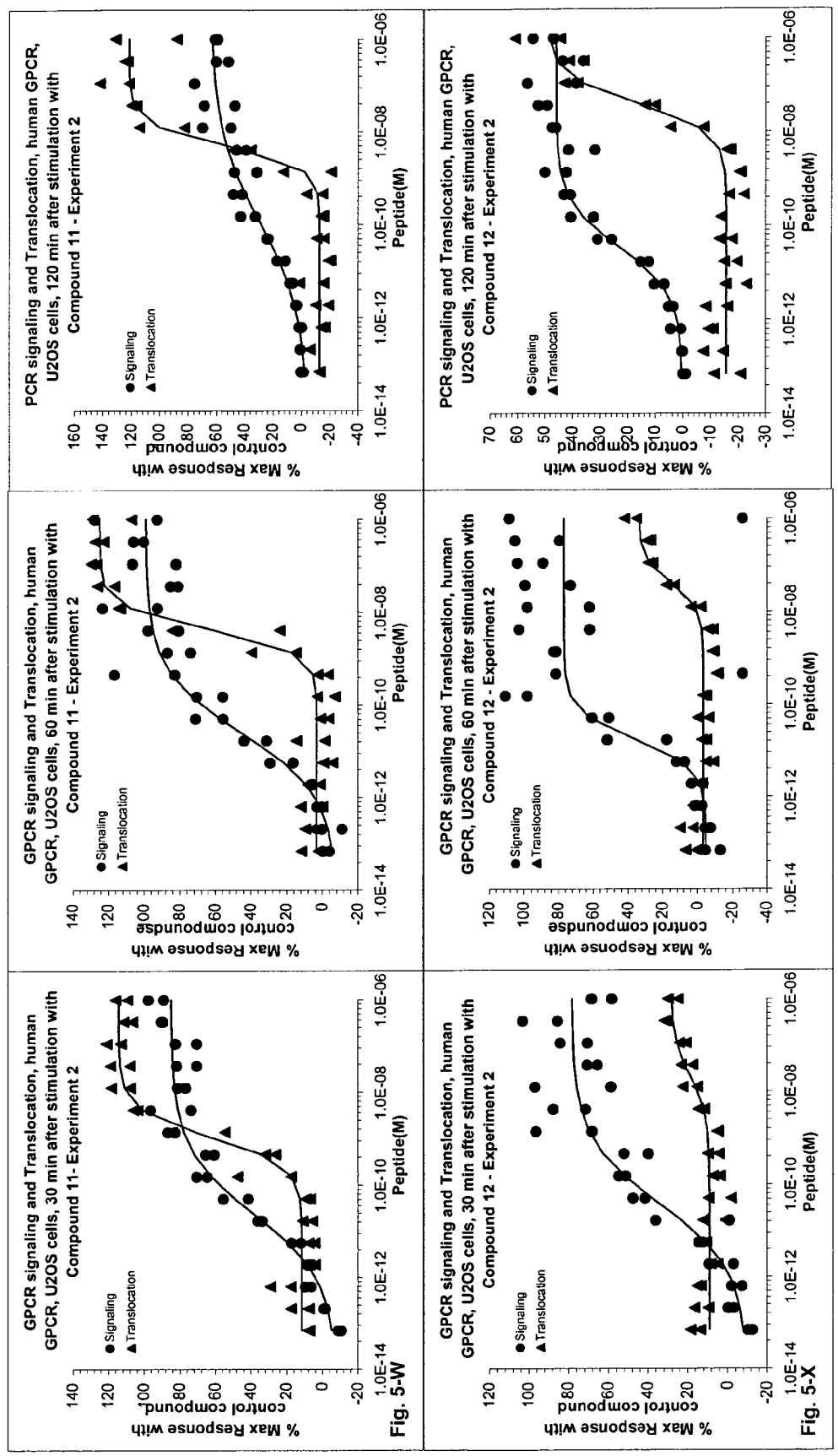
Fig. 5-W
Fig. 5-X

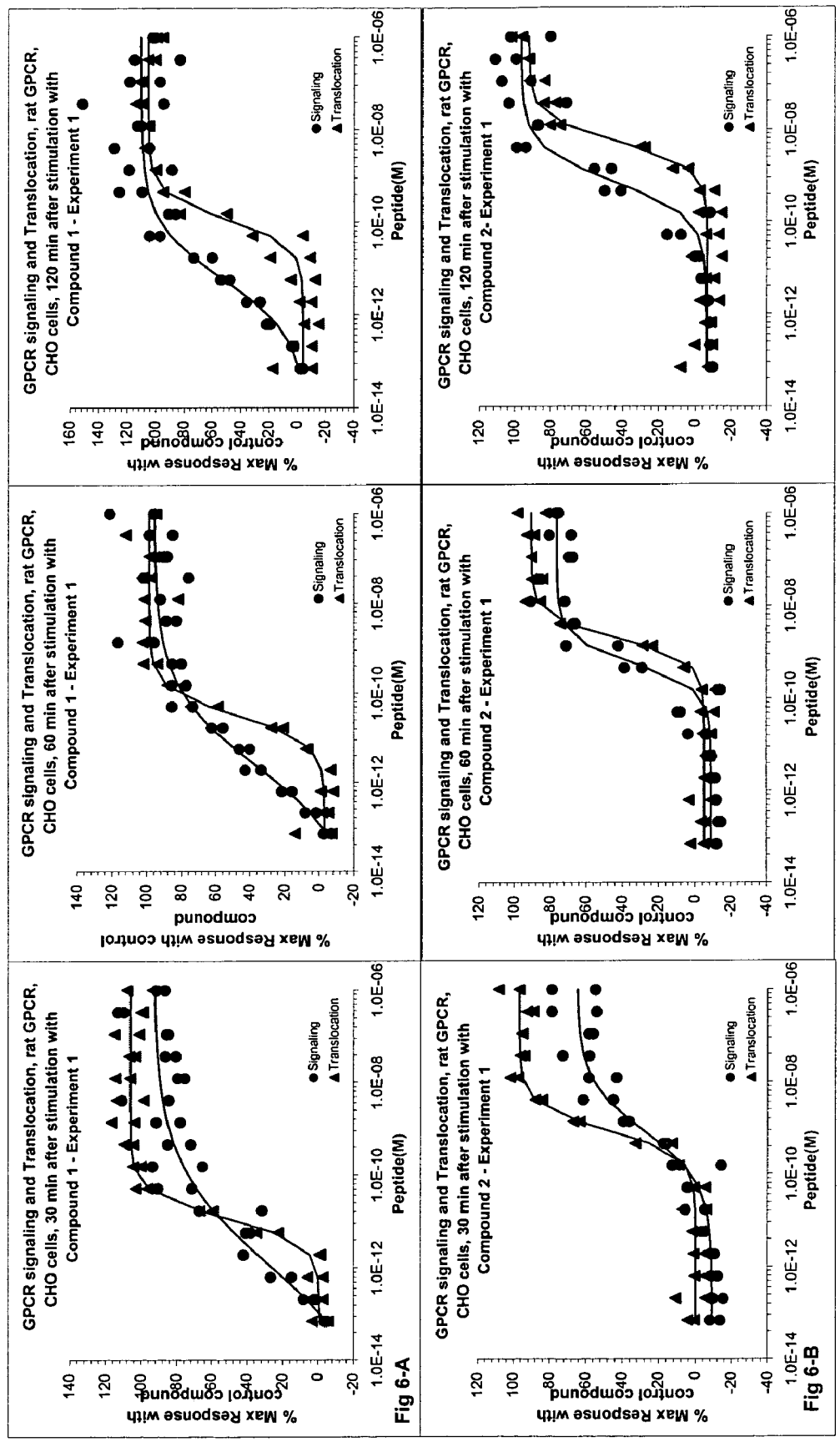
Fig 6-A
Fig 6-B

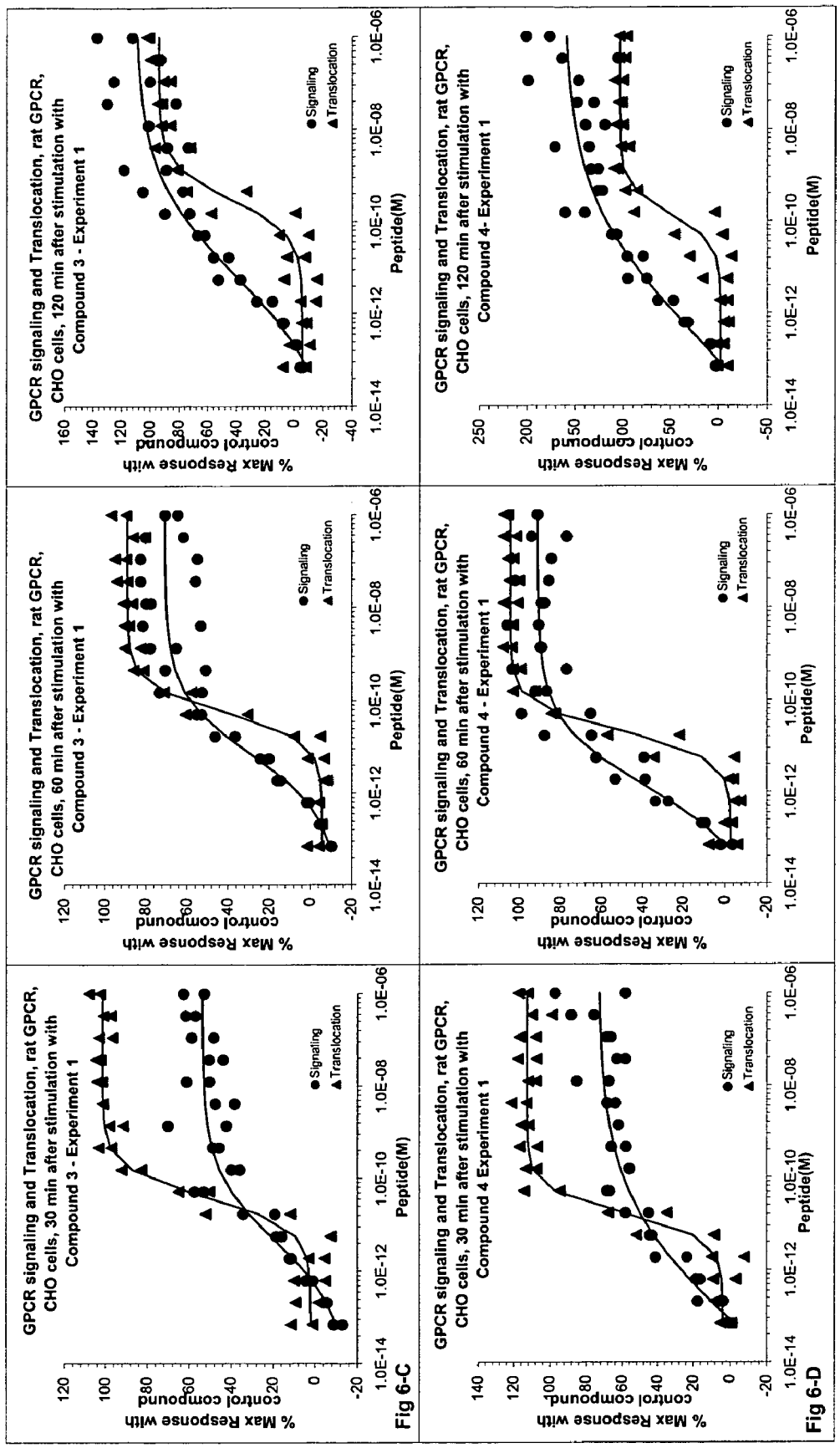

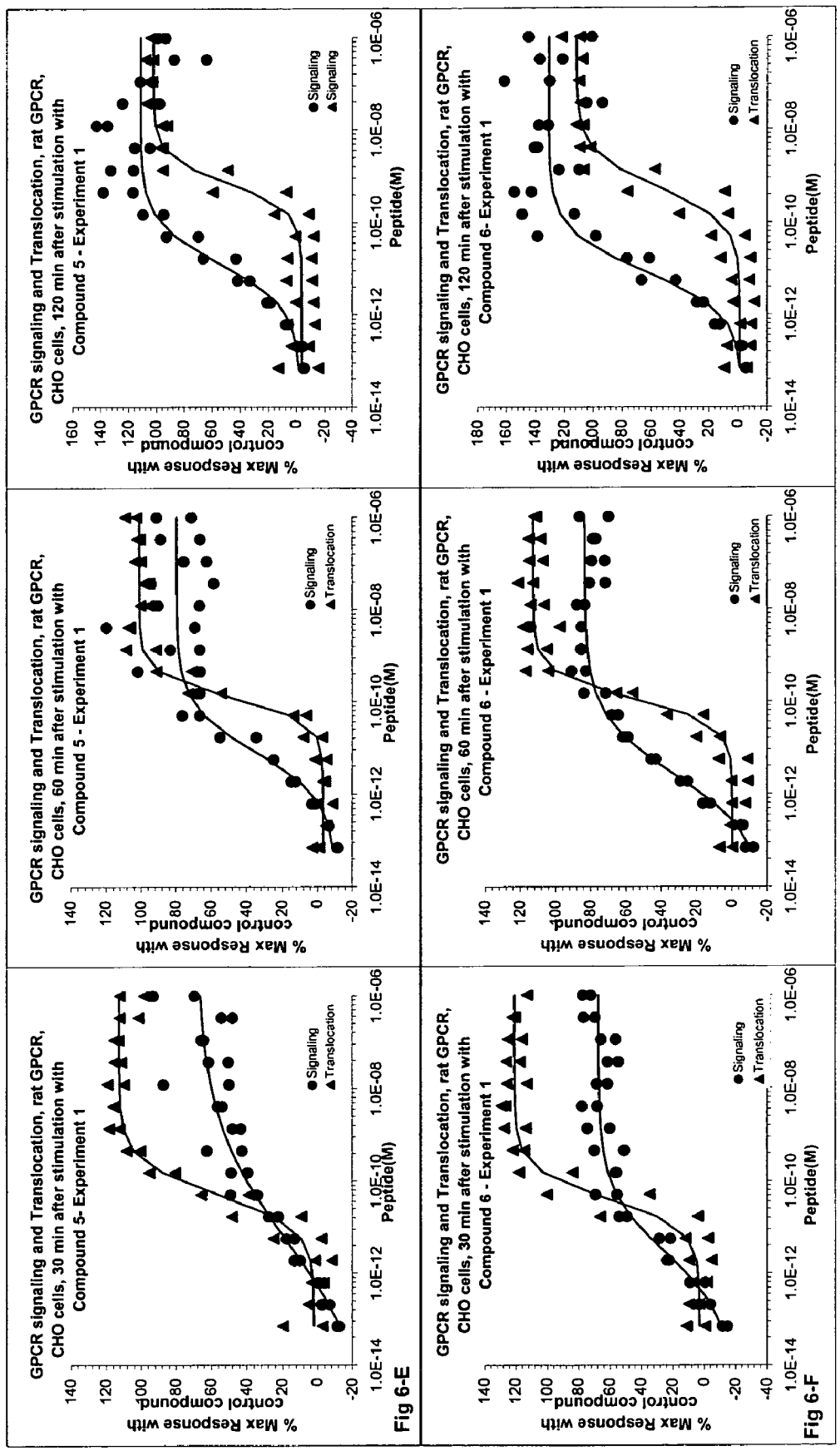
Fig 6-E
Fig 6-F

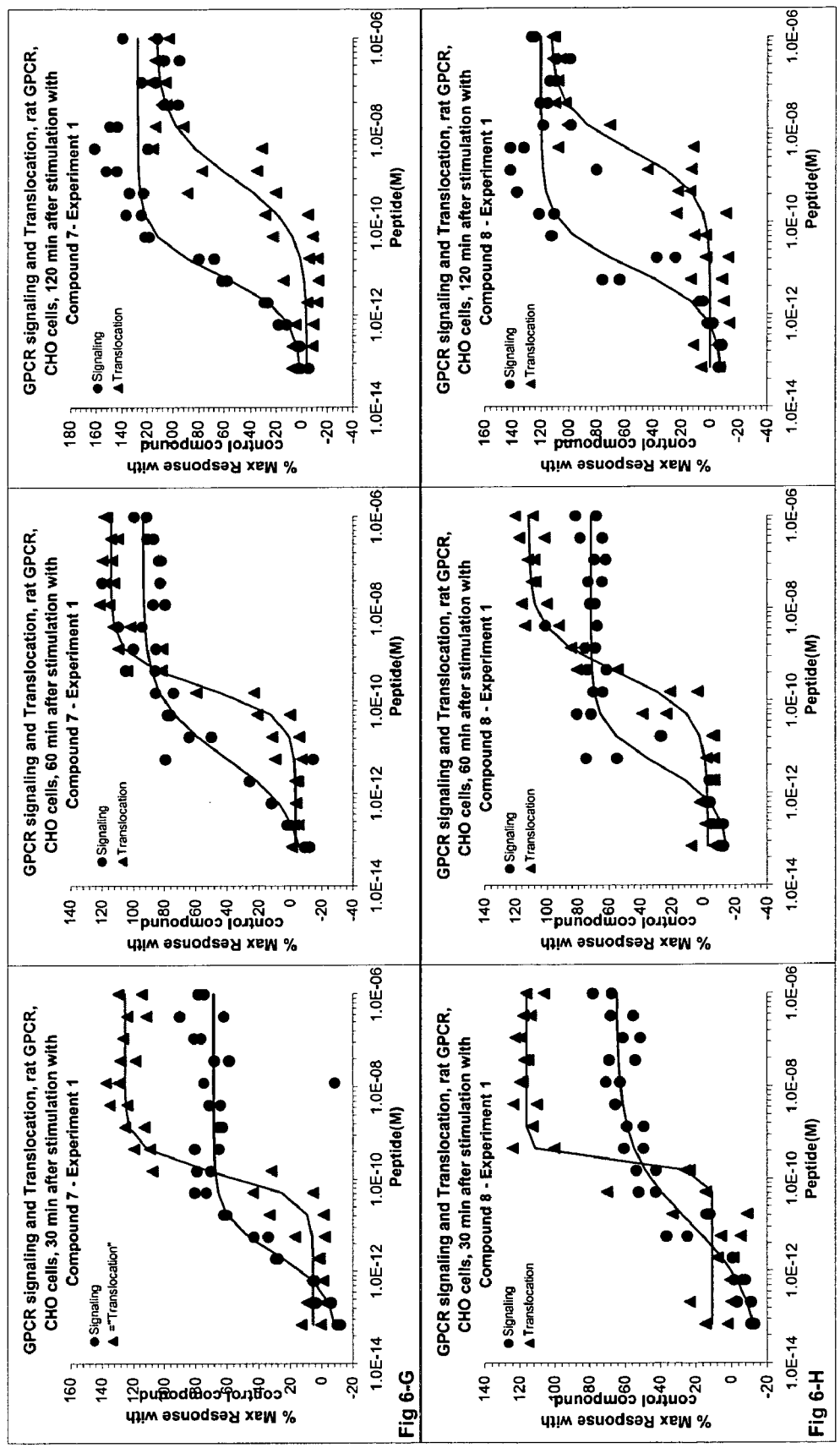
Fig 6-G
Fig 6-H

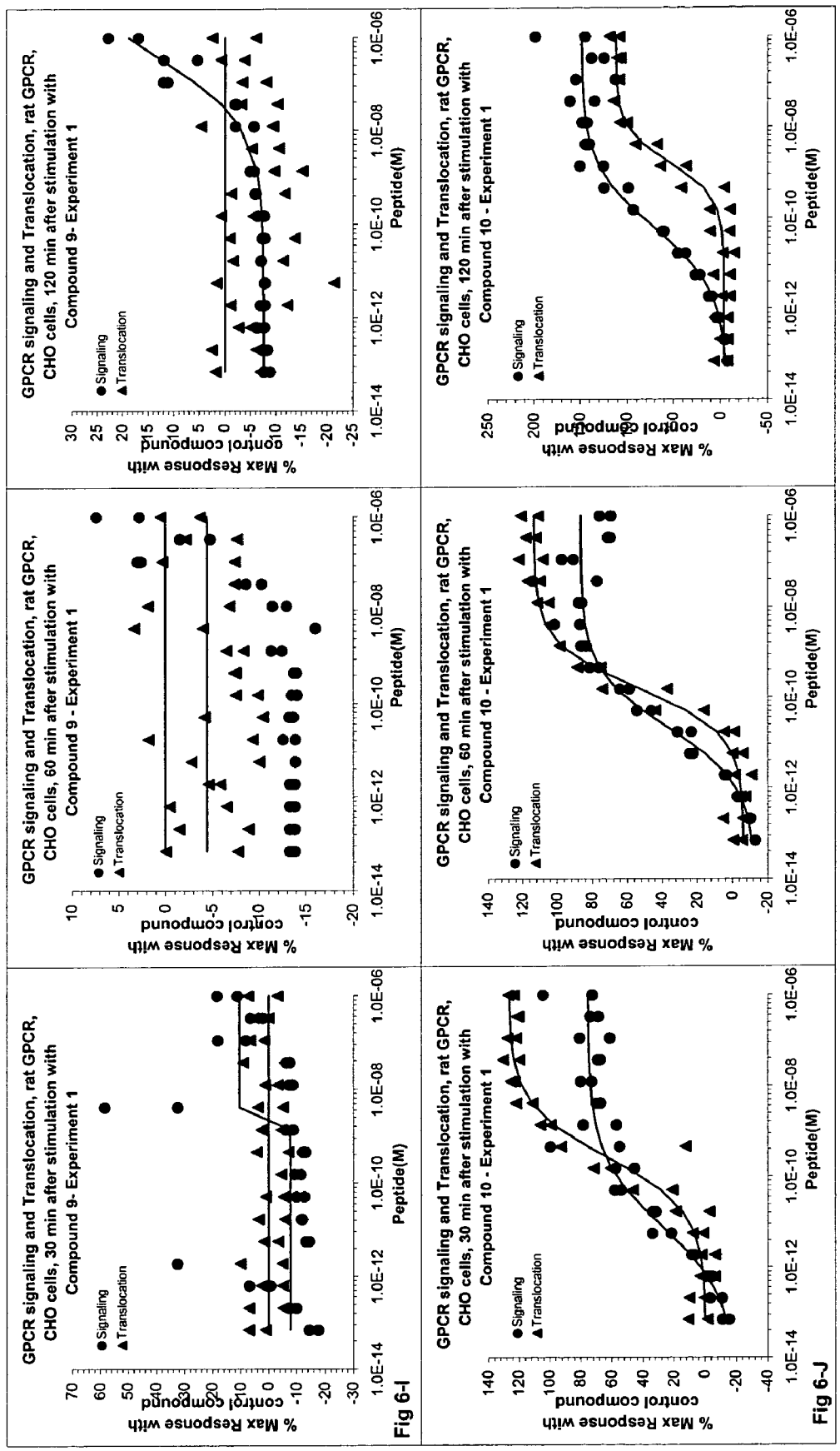
Fig 6-I
Fig 6-J

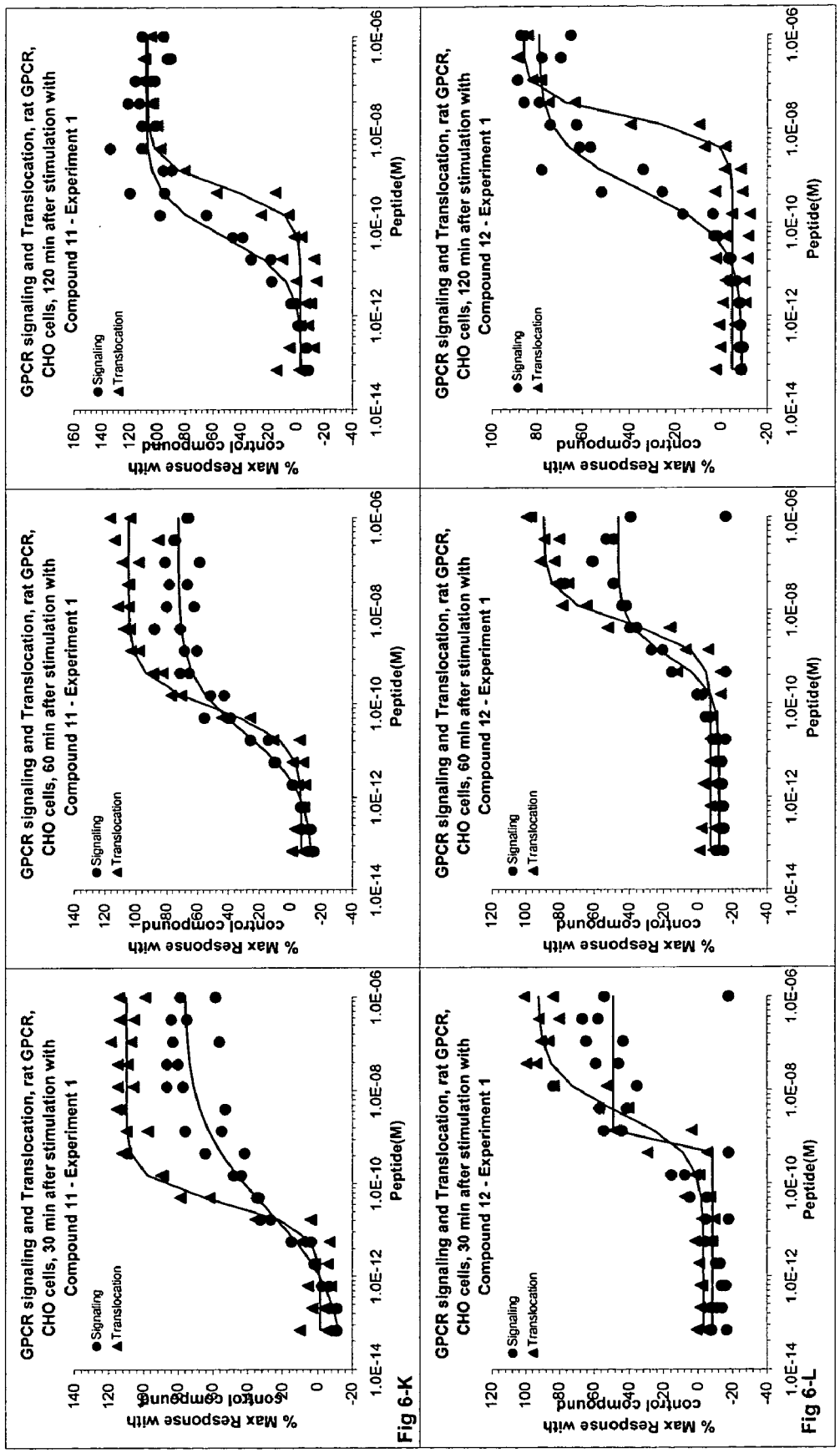
Fig 6-K
Fig 6-L

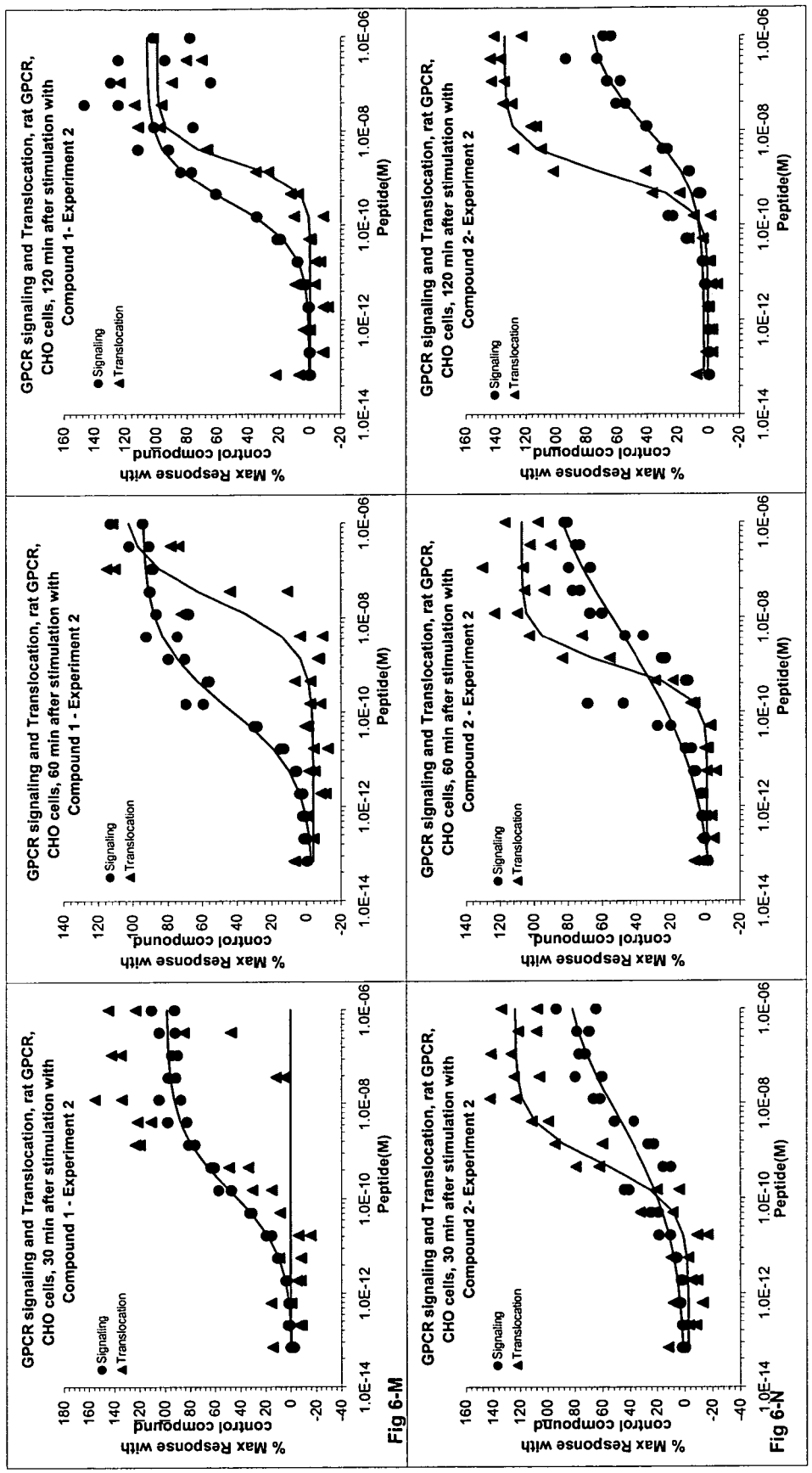
Fig 6-M
Fig 6-N

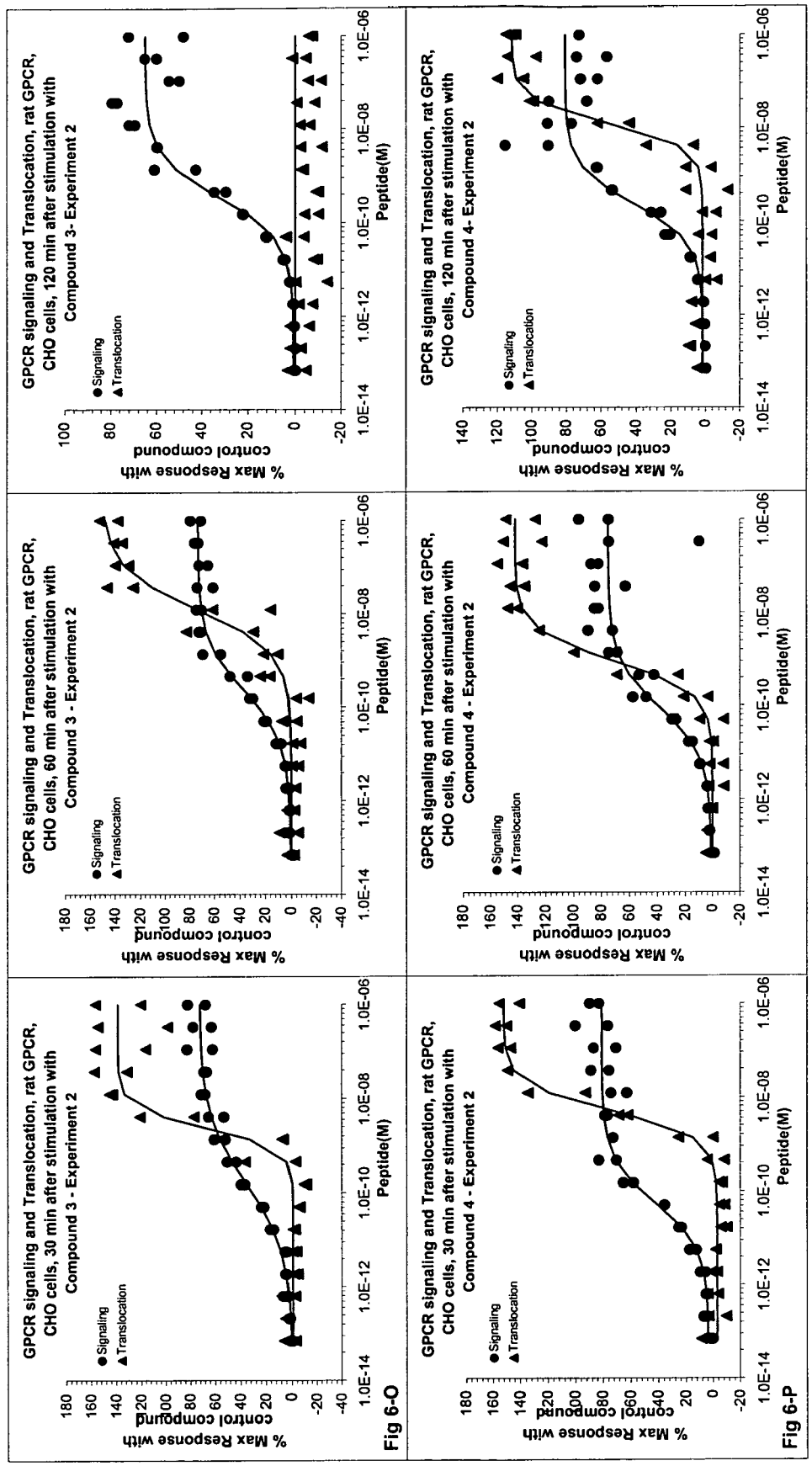

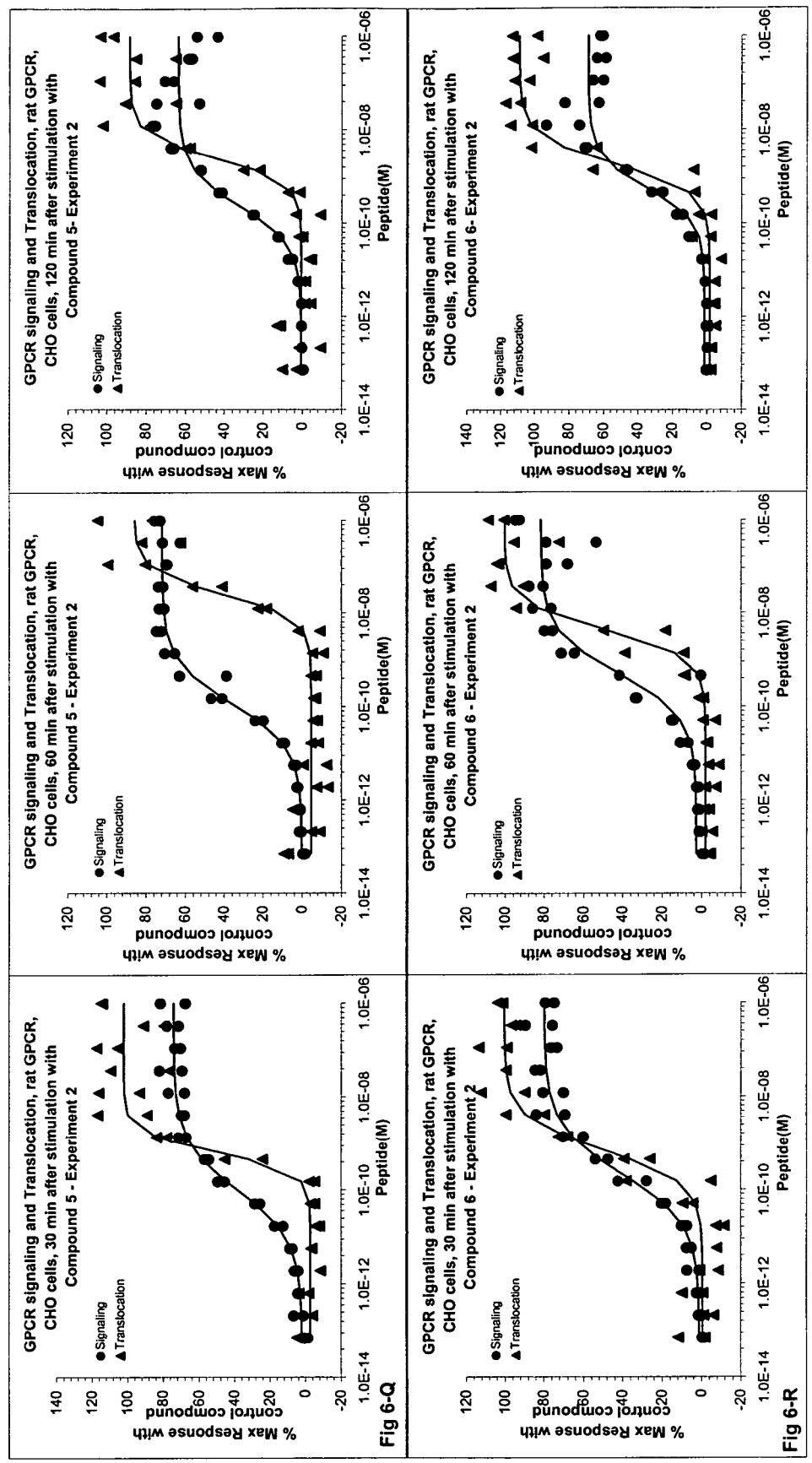
Fig 6-Q
Fig 6-R

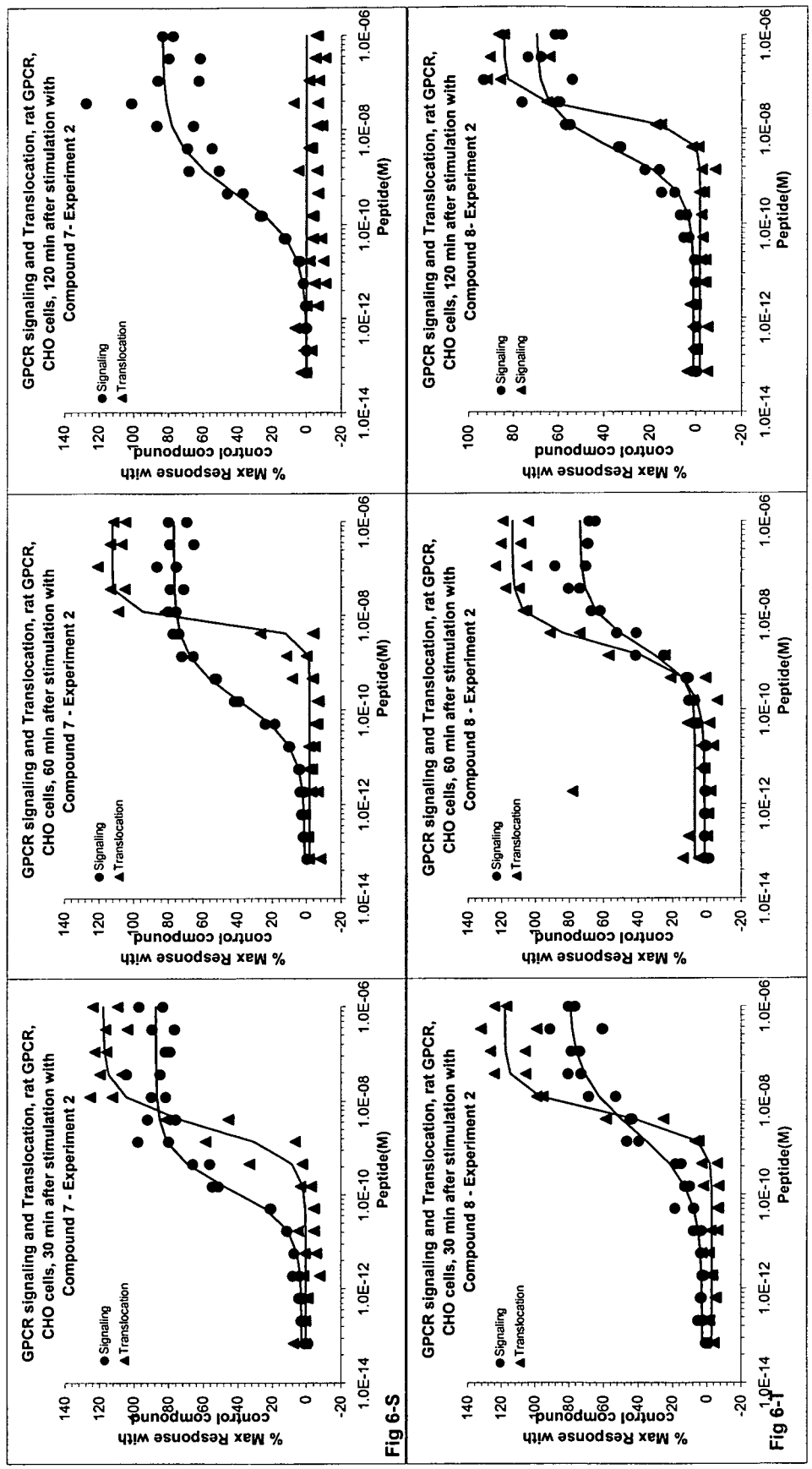
Fig 6-S
Fig 6-T

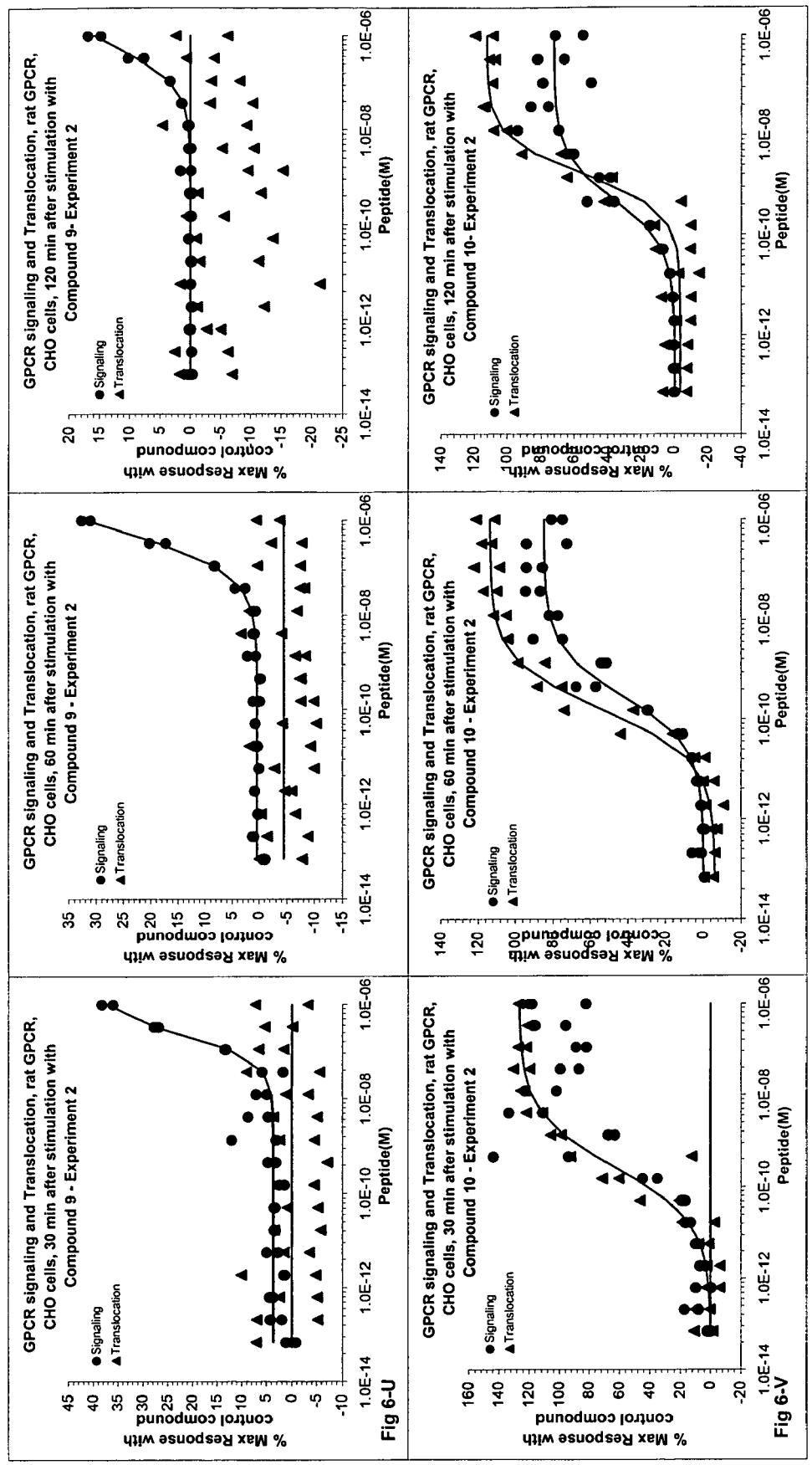
Fig 6-U
Fig 6-V

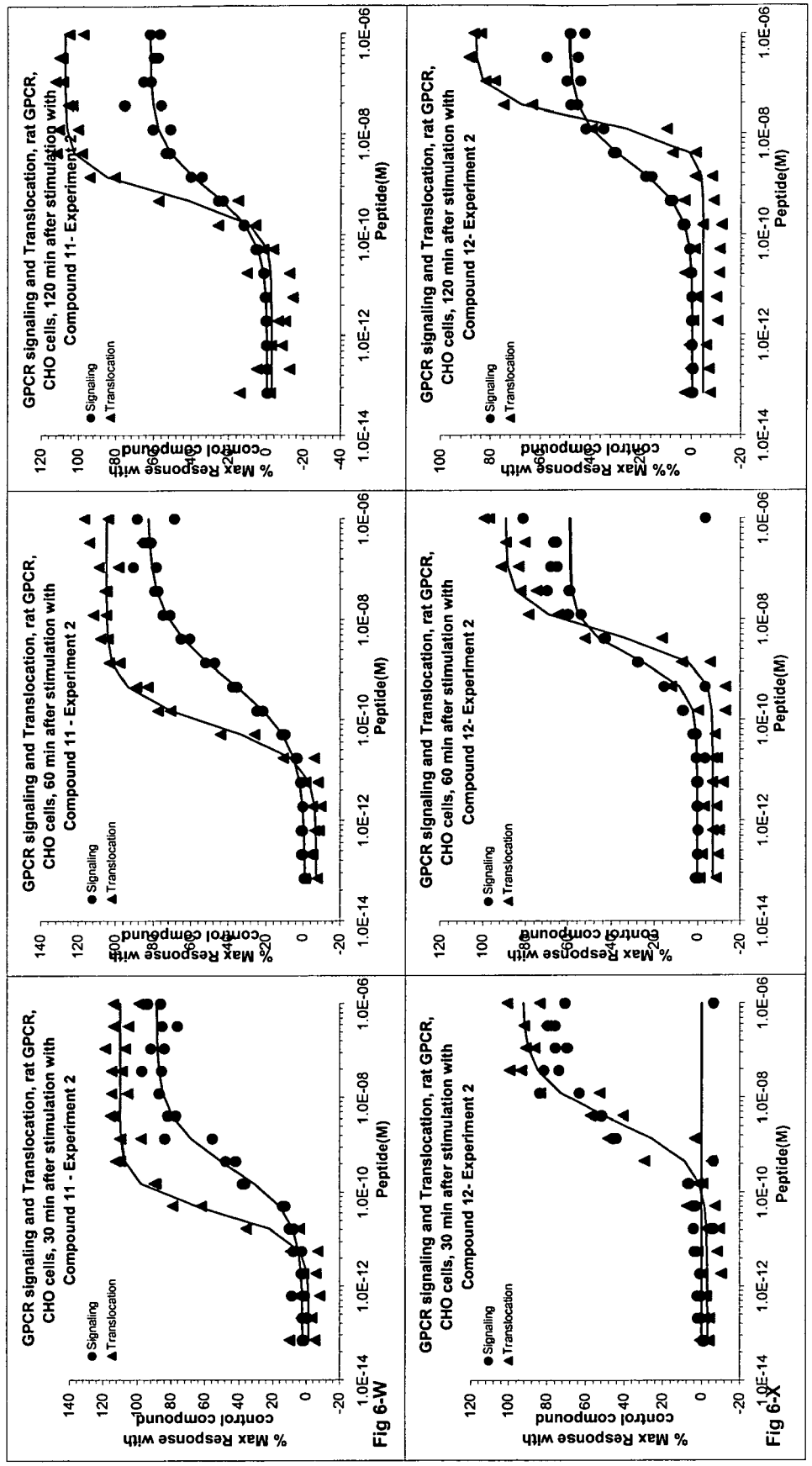

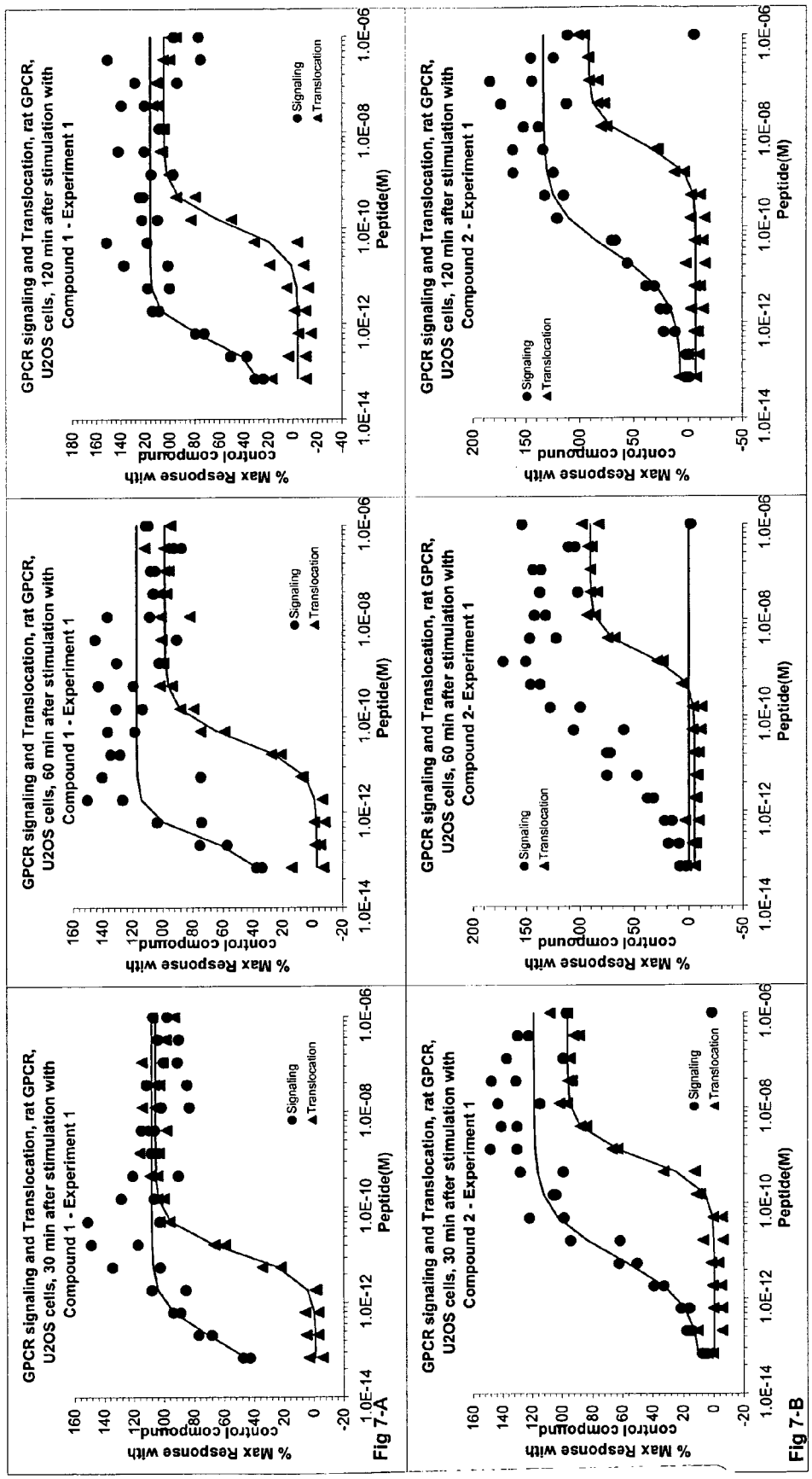
Fig 7-A
Fig 7-B

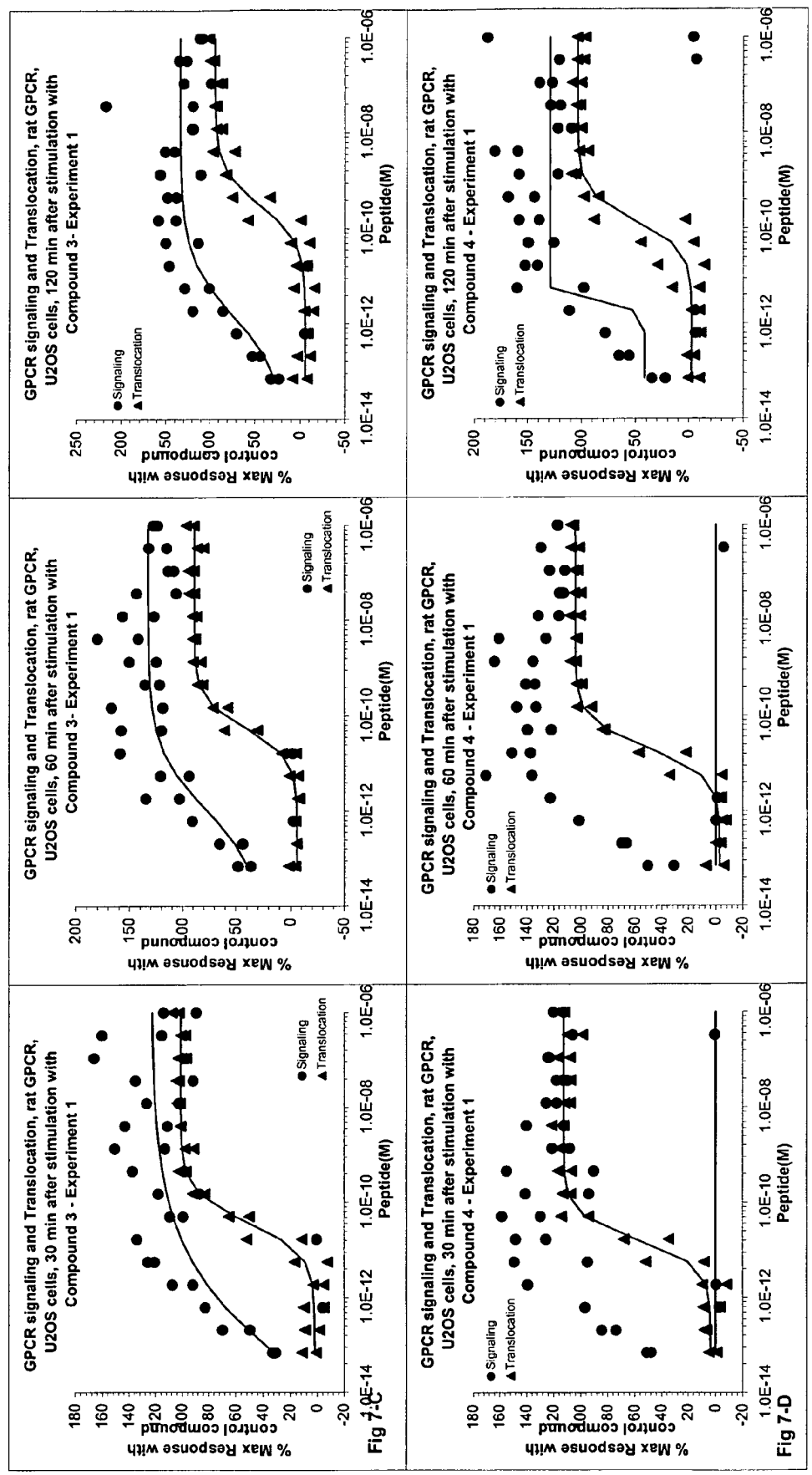

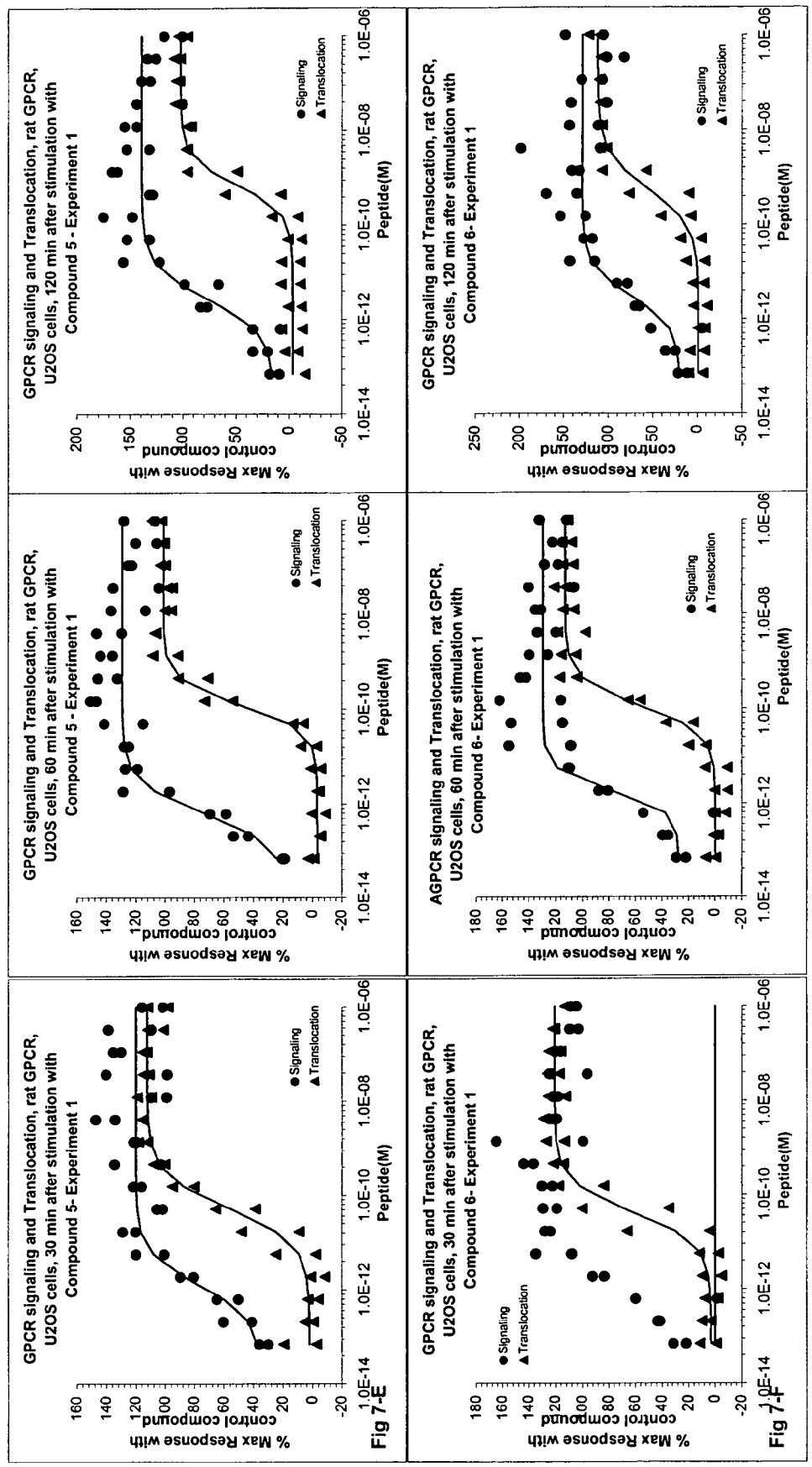

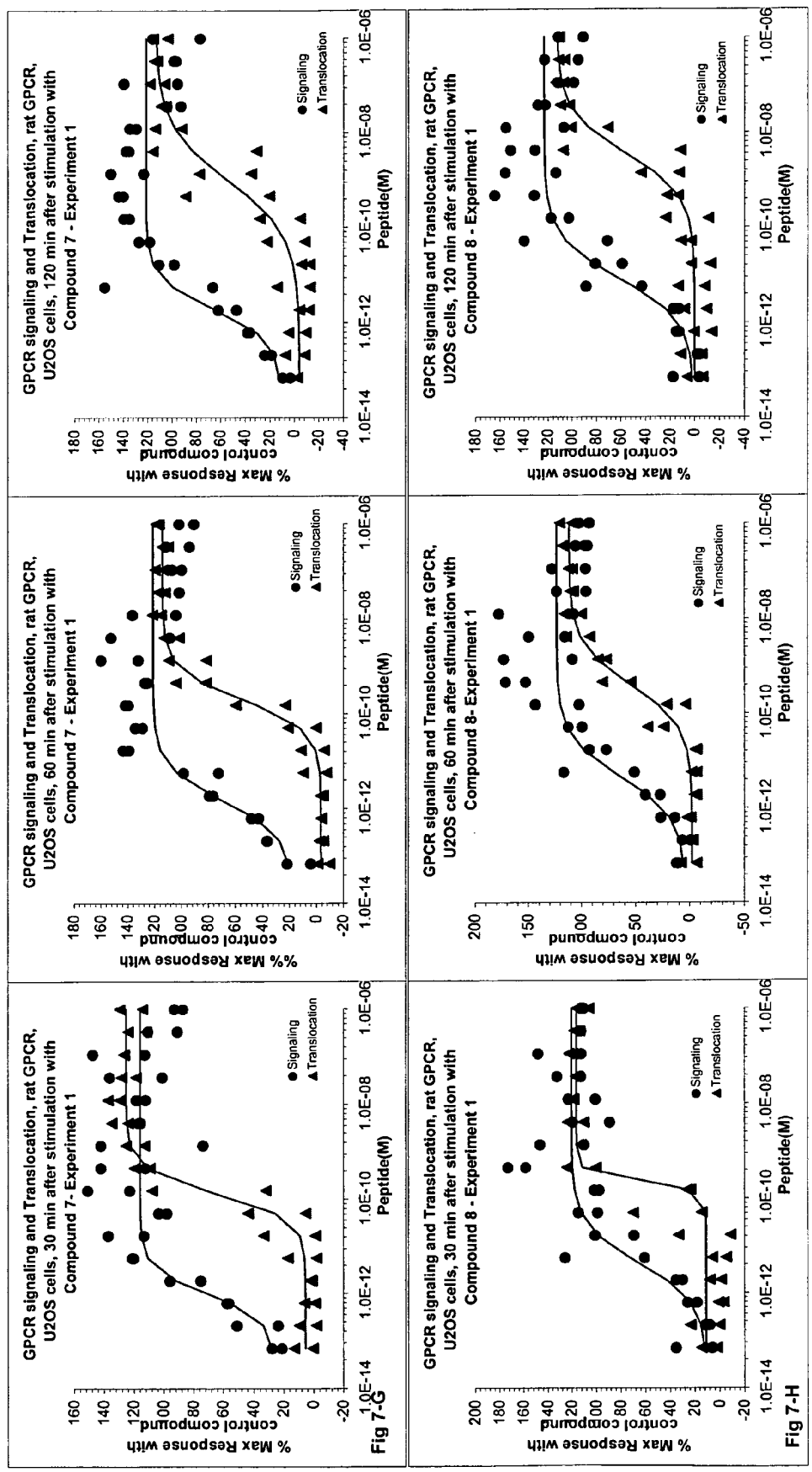

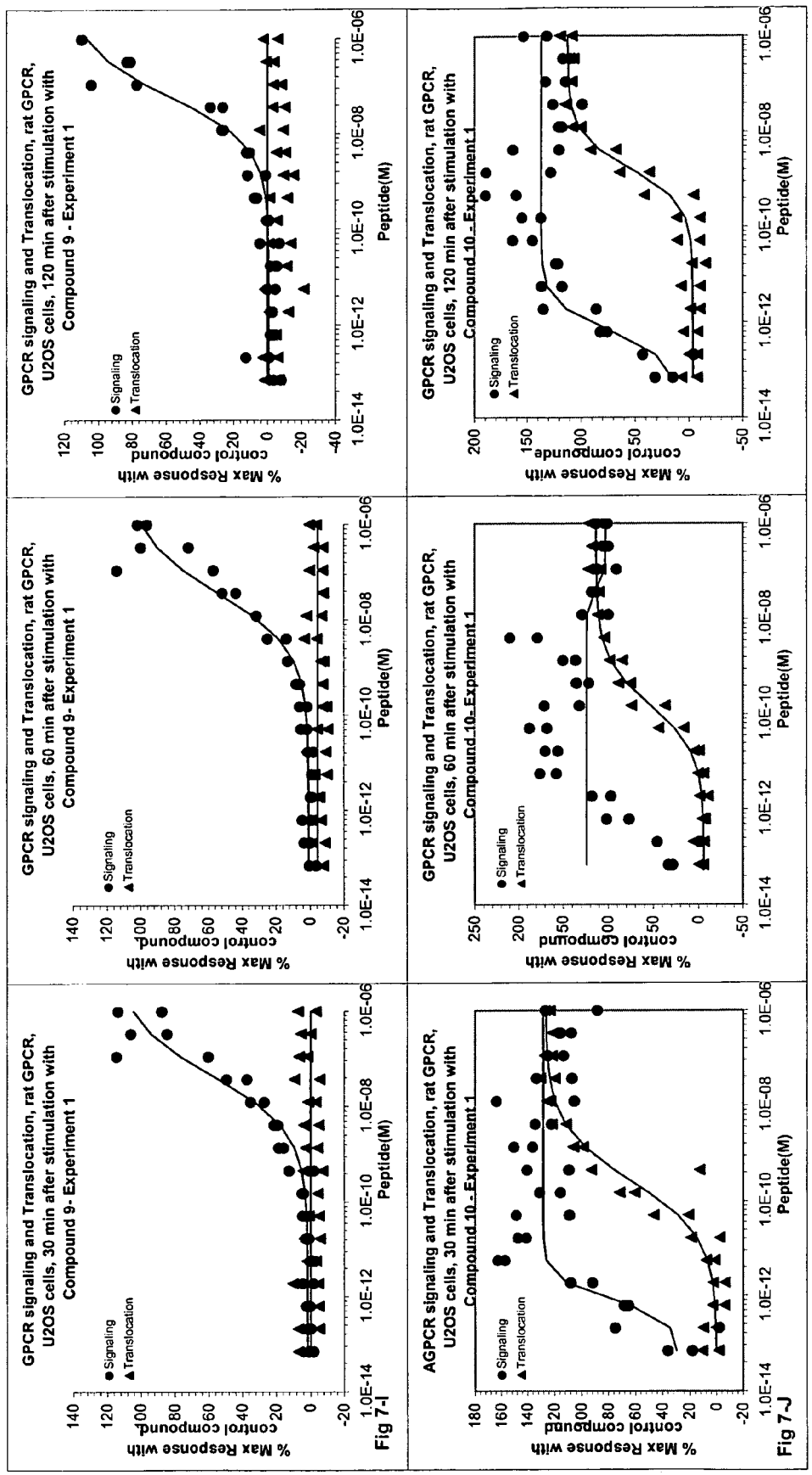

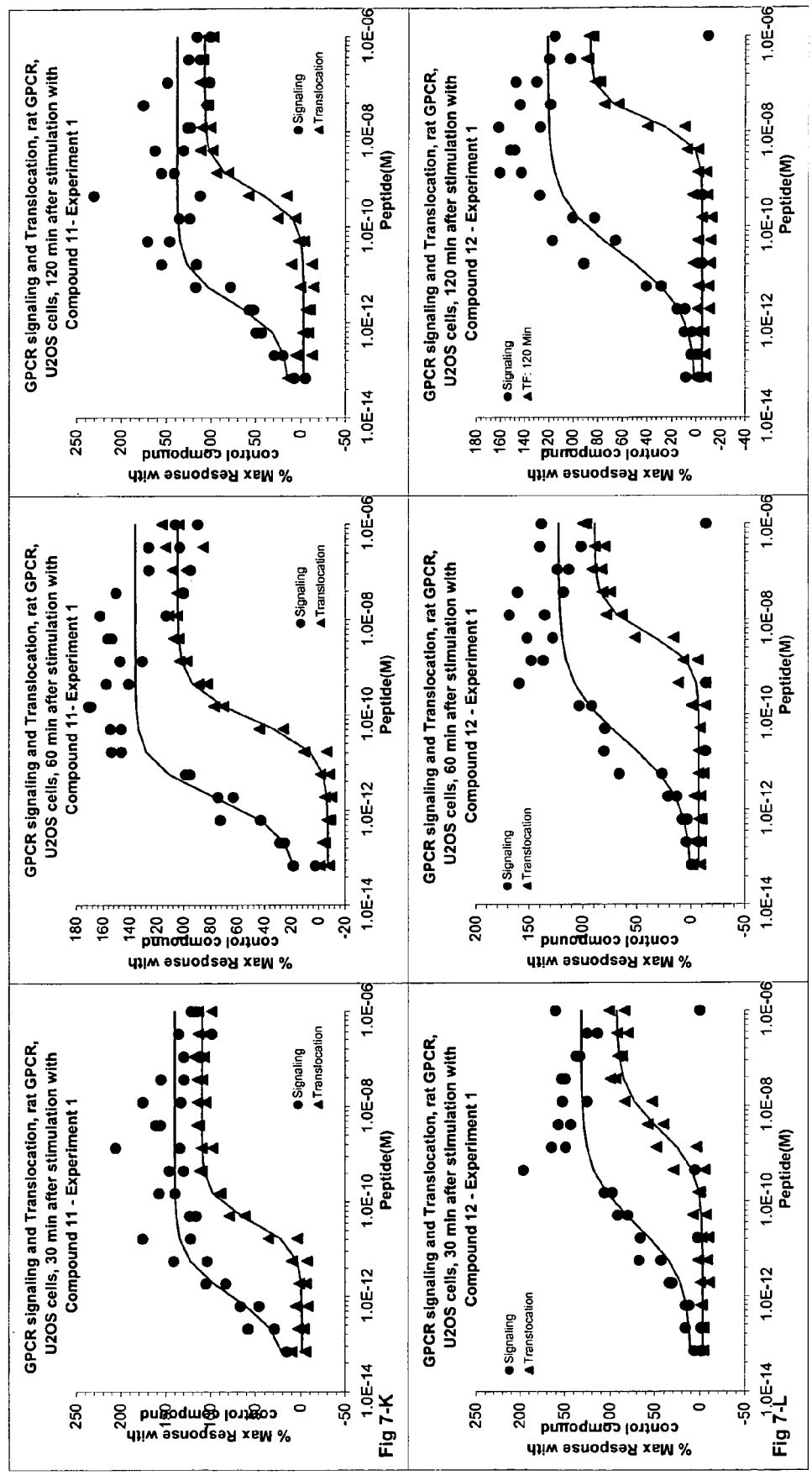

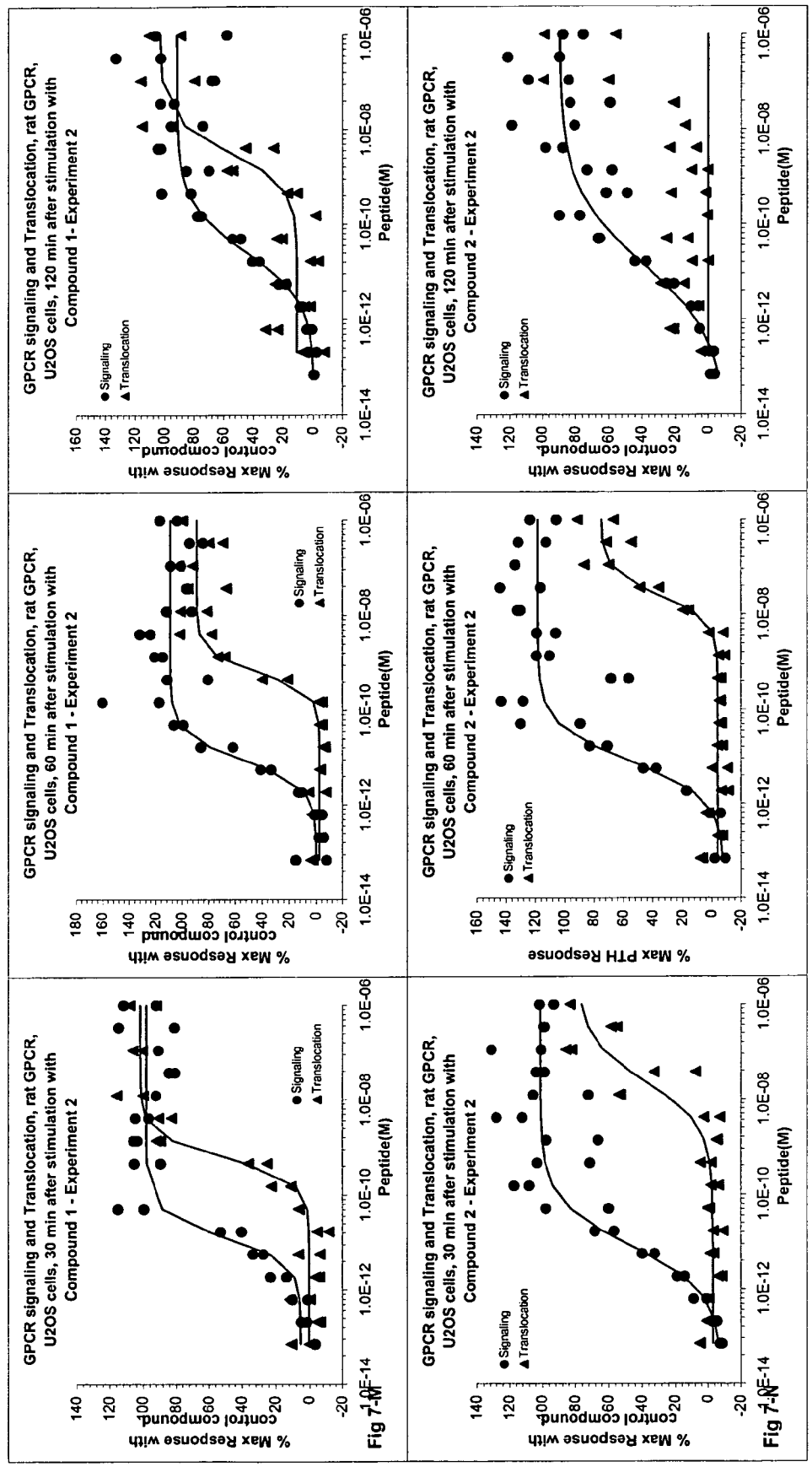
Fig 7-M
Fig 7-N

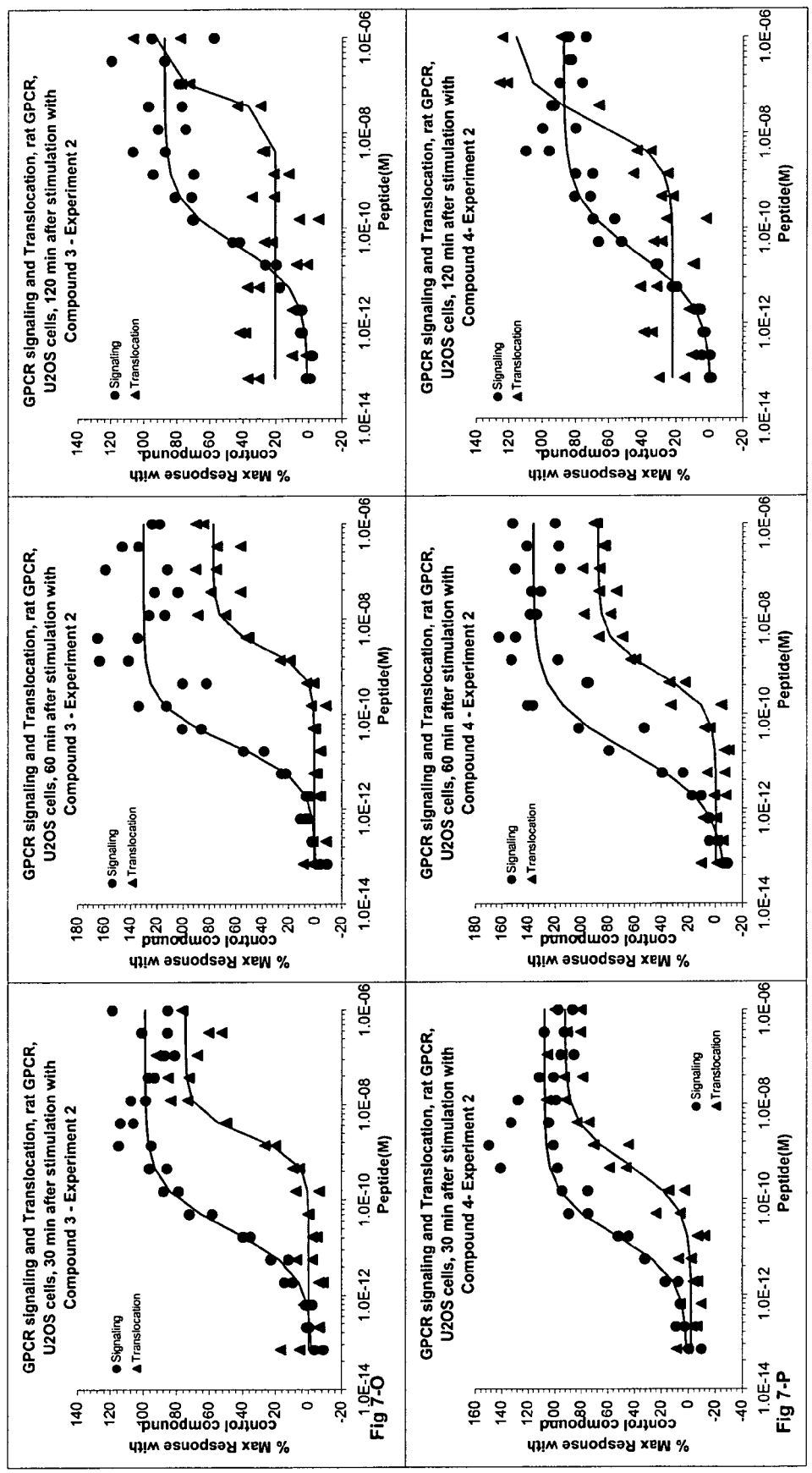

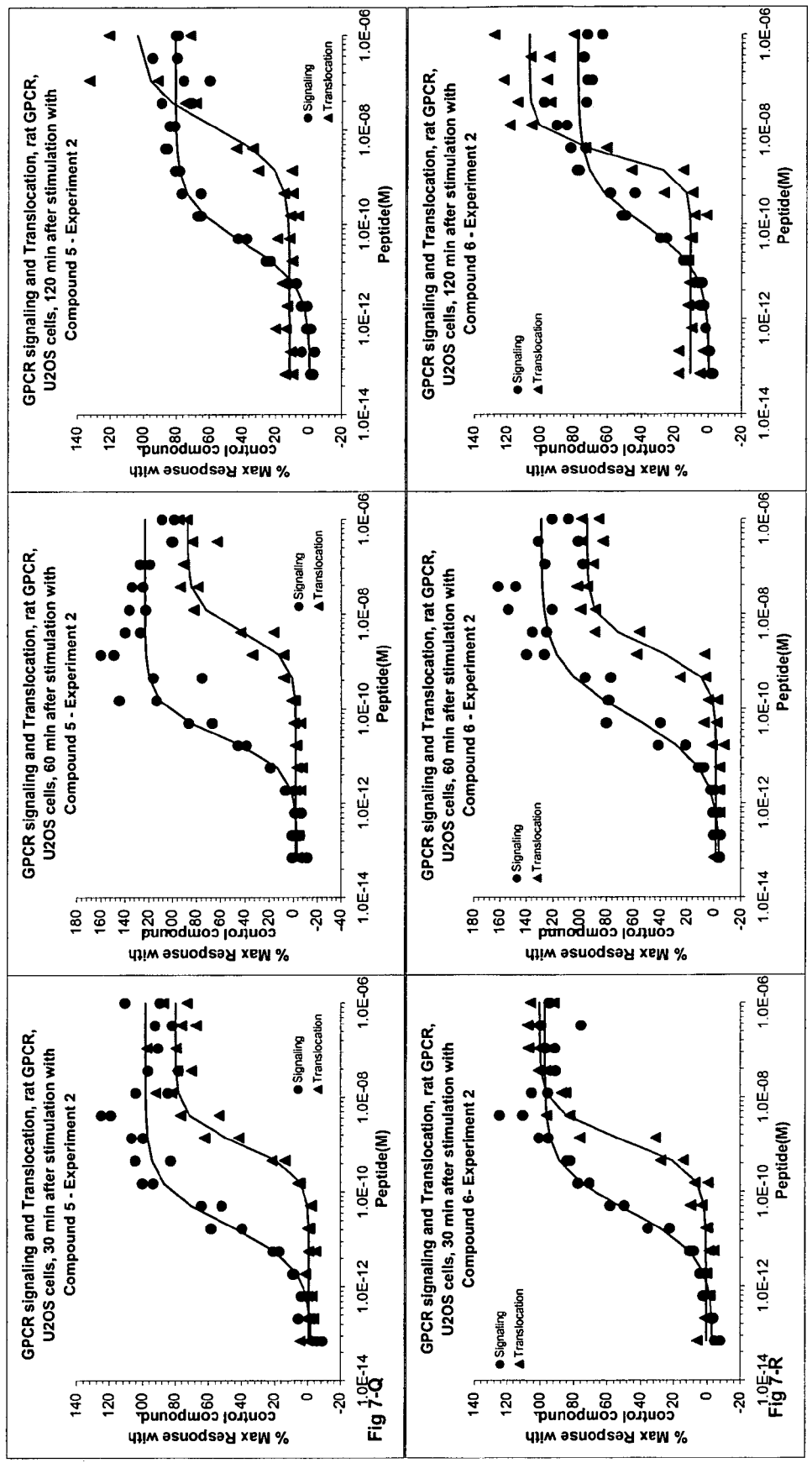

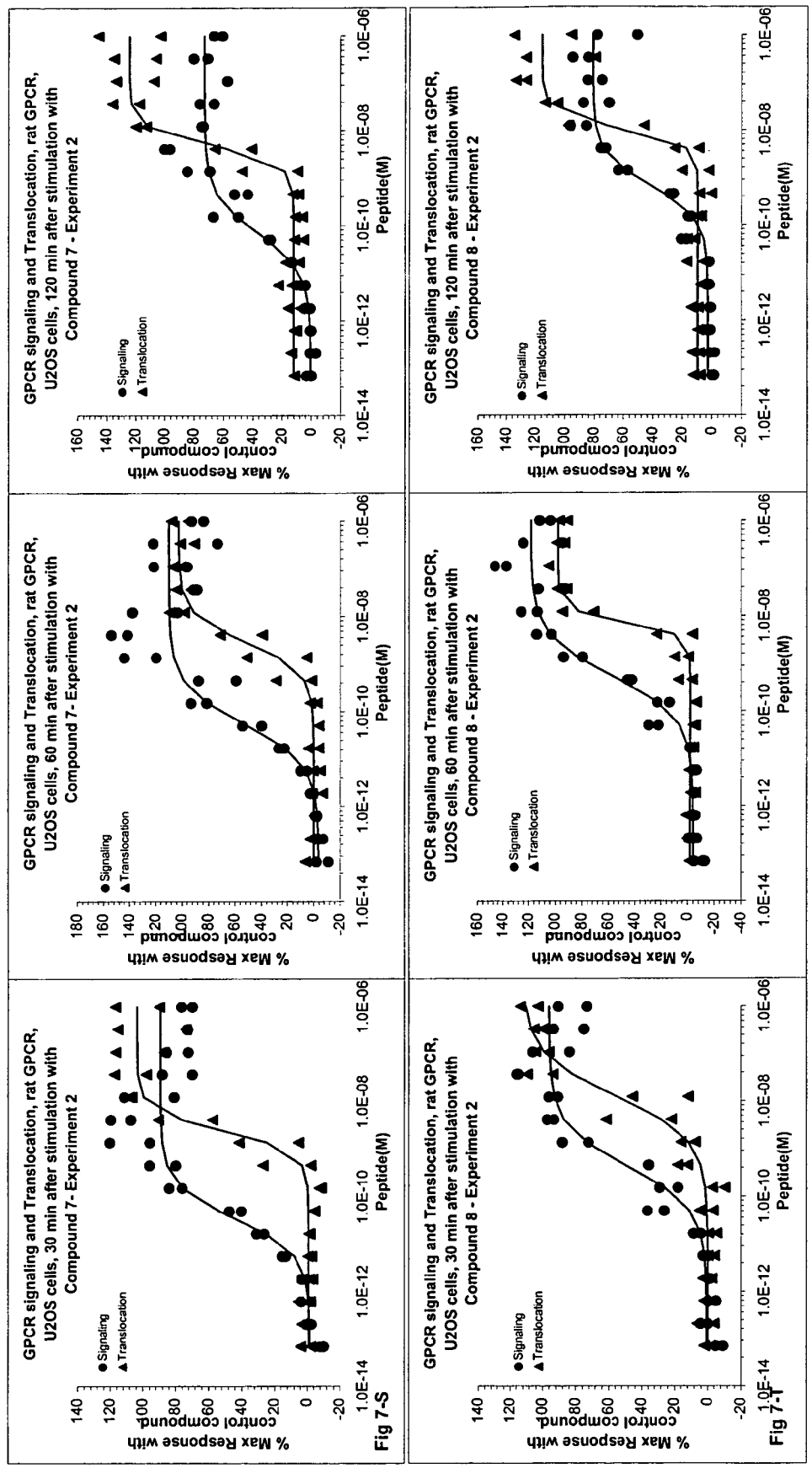

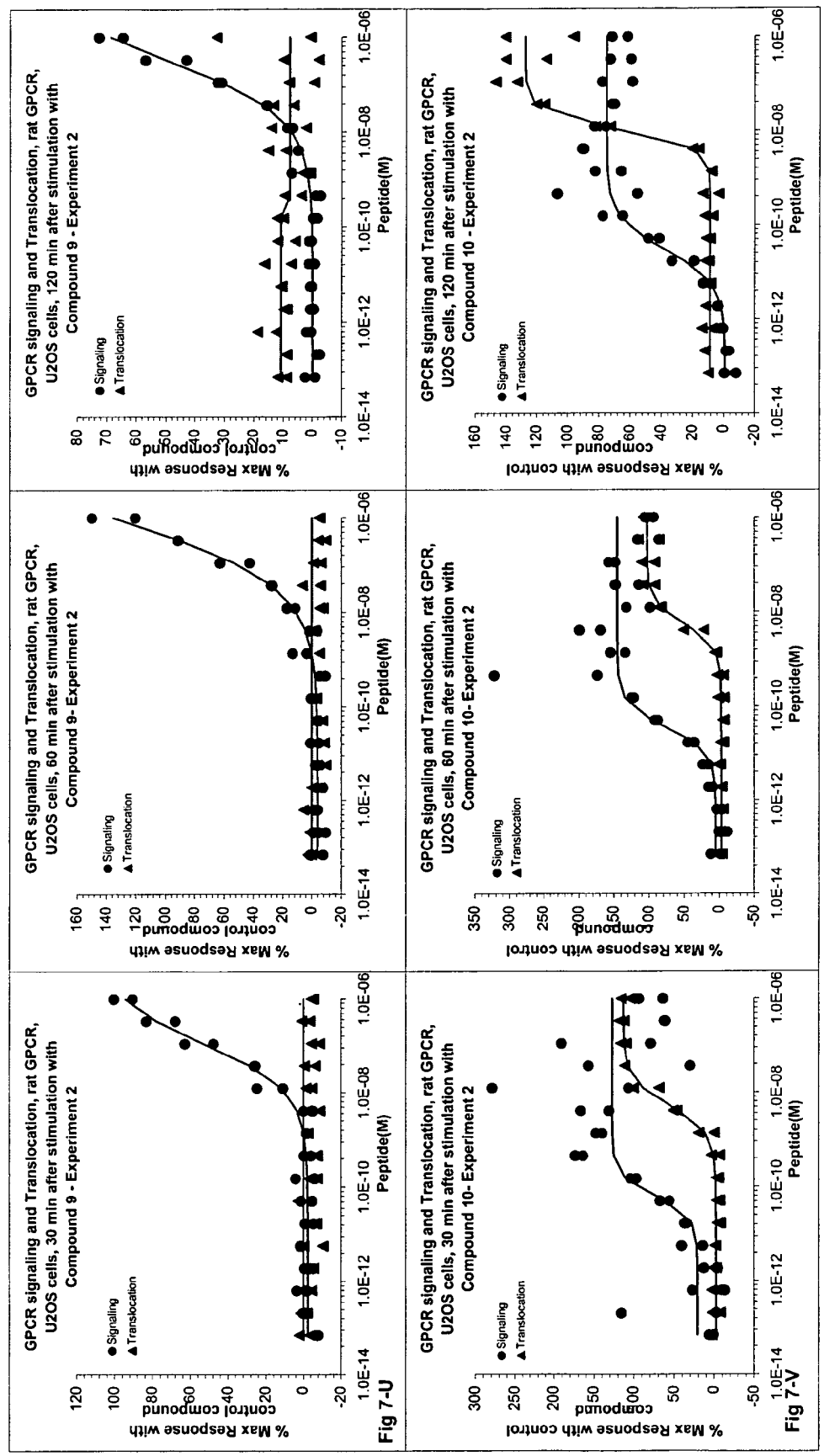
Fig 7-U
Fig 7-V

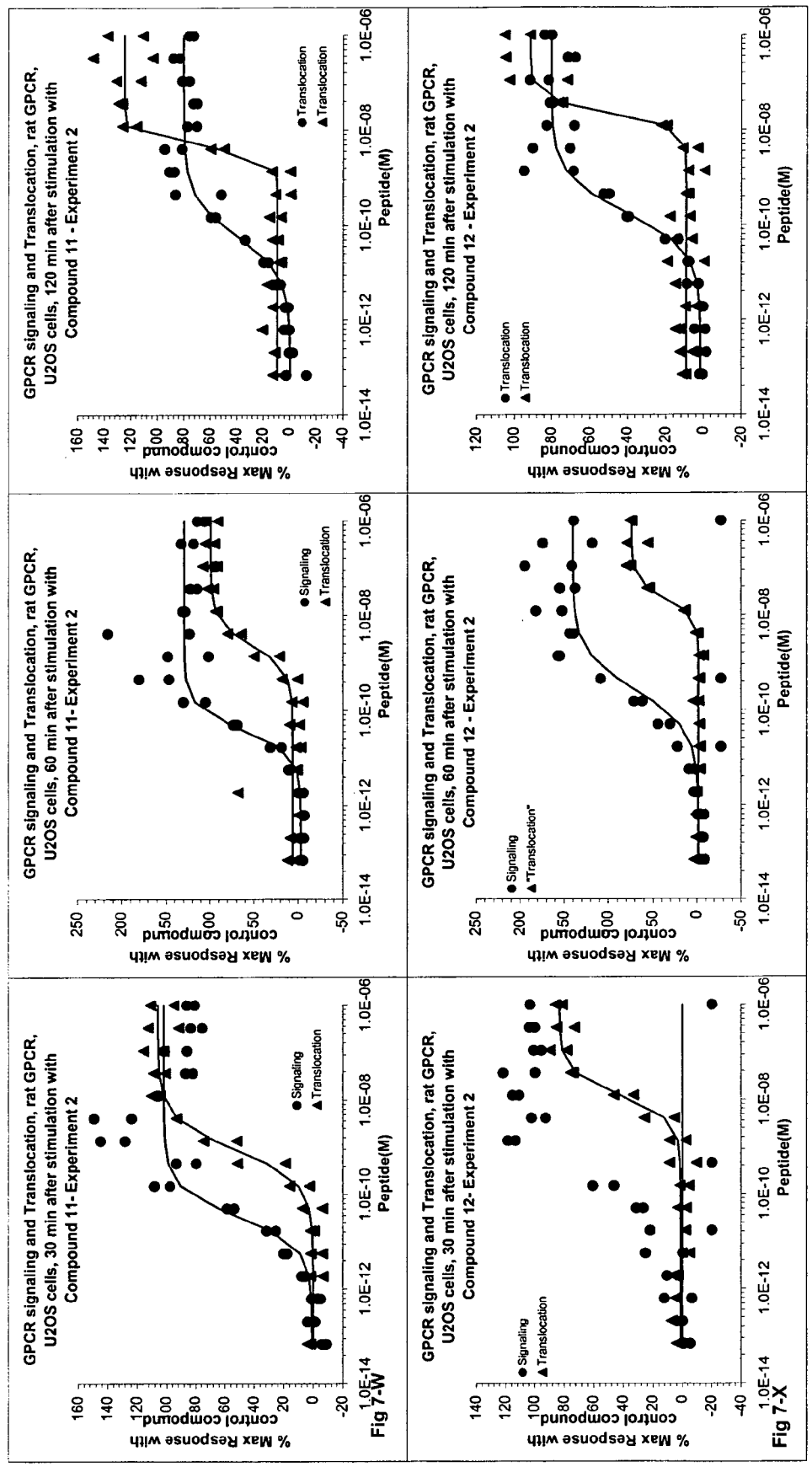

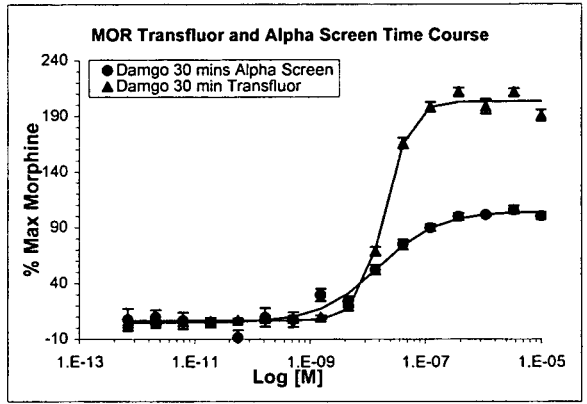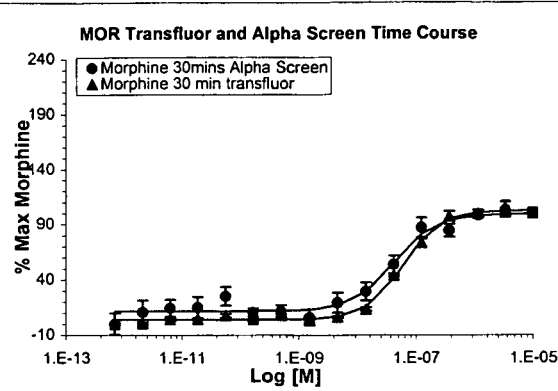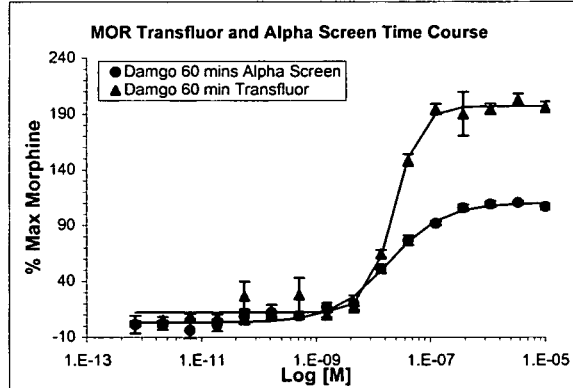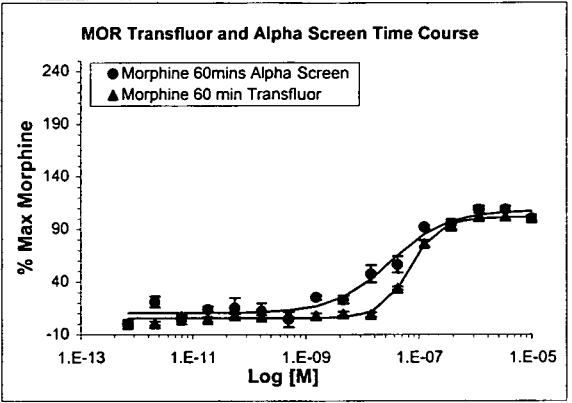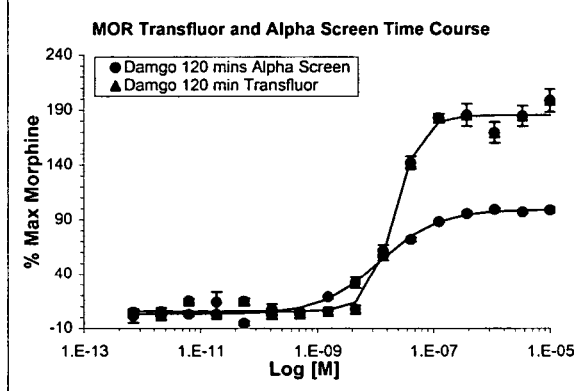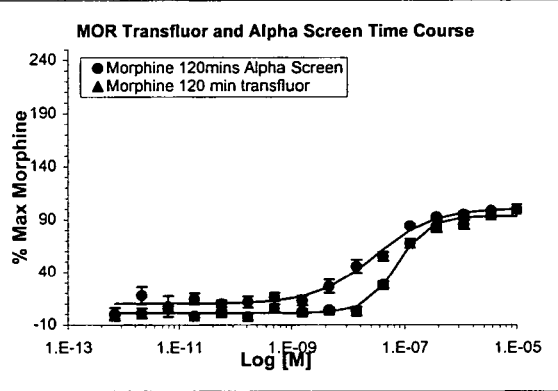
Fig 8-A         Fig 8-B

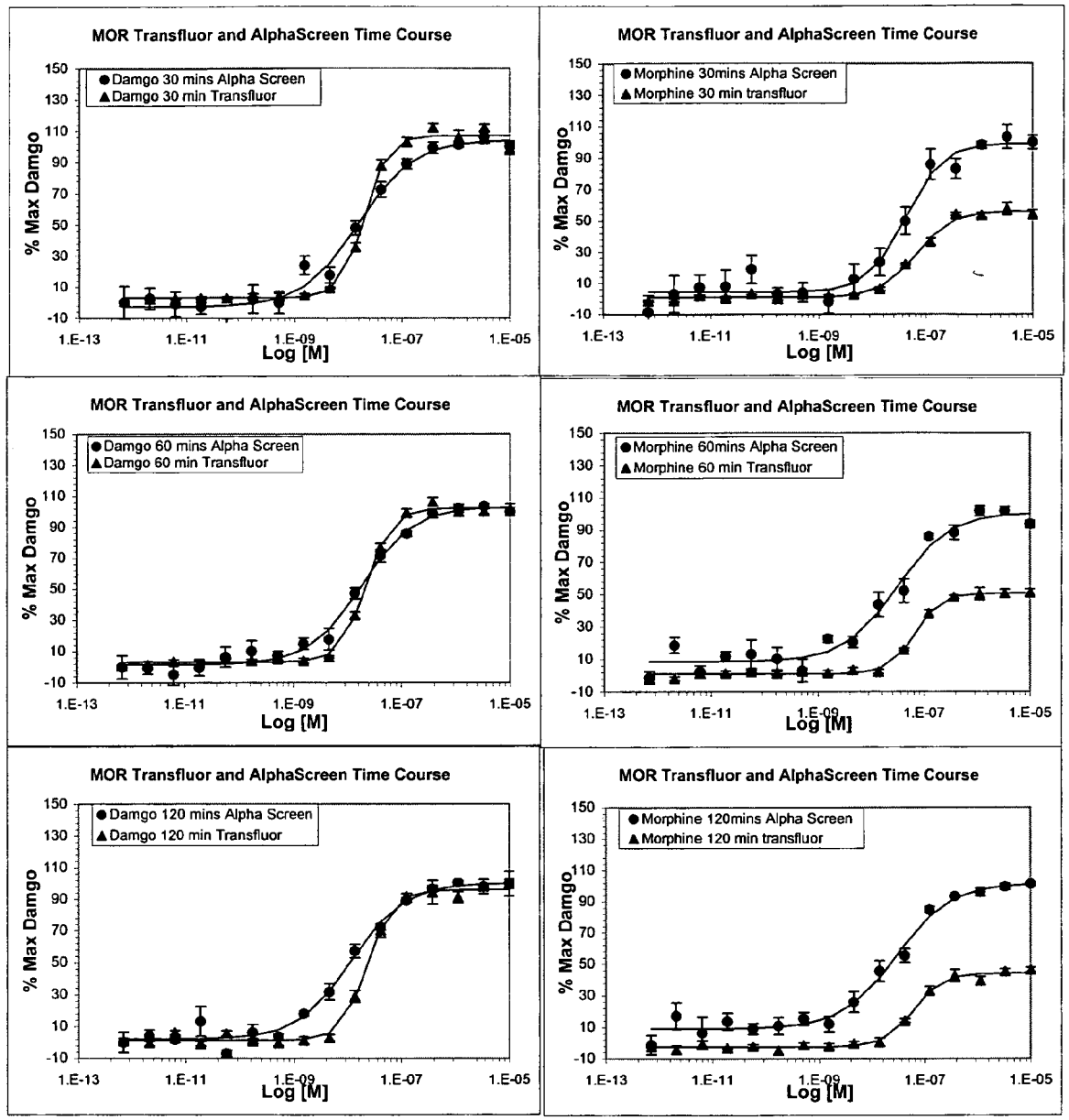
Fig 8-C    Fig 8-D

METHODS OF IDENTIFYING REDUCED INTERNALIZATION TRANSMEMBRANE RECEPTOR AGONISTS

This application claims priority to U.S. Ser. No. 60/421,538 filed on Oct. 25, 2002, the contents of which are incorporated by reference in their entirety.

FIELD OF THE INVENTION

Methods of identifying Reduced Internalization Transmembrane Receptor Agonists are disclosed.

BACKGROUND

Transmembrane receptors (TMRs) are proteins that span membranes and have the ability to interact with or bind a ligand, which may be a hormone, small molecule, lipid, nucleic acid, or peptide, for example. G protein-coupled receptors (GPCRs) are cell surface transmembrane proteins that translate hormone or ligand binding into intracellular signals, as do most TMRs. TMRs, or GPCRs, are found in all animals, insects, and plants. TMR, or GPCR, signaling plays a pivotal role in regulating various physiological functions including phototransduction, olfaction, neurotransmission, vascular tone, cardiac output, digestion, pain, and fluid and electrolyte balance. GPCRs, although involved in numerous physiological functions, share a number of common structural features. They contain seven membrane domains bridged by alternating intracellular and extracellular loops and an intracellular carboxyl-terminal tail of variable length.

GPCRs and other transmembrane receptors have been implicated in a number of disease states, including, but not limited to: cardiac indications such as angina pectoris, essential hypertension, myocardial infarction, supraventricular and ventricular arrhythmias, congestive heart failure, atherosclerosis, renal failure, diabetes, respiratory indications such as asthma, chronic bronchitis, bronchospasm, emphysema, airway obstruction, upper respiratory indications such as rhinitis, seasonal allergies, inflammatory disease, inflammation in response to injury, rheumatoid arthritis, chronic inflammatory bowel disease, glaucoma, hypergastrinemia, gastrointestinal indications such as acid/peptic disorder, erosive esophagitis, gastrointestinal hypersecretion, mastocytosis, gastrointestinal reflux, peptic ulcer, Zollinger-Ellison syndrome, pain, obesity, bulimia nervosa, depression, obsessive-compulsive disorder, organ malformations (for example, cardiac malformations), neurodegenerative diseases such as Parkinson's Disease and Alzheimer's Disease, multiple sclerosis, Epstein-Barr infection and cancer.

The magnitude of the physiological responses controlled by TMRs can be linked to the balance between TMR signaling and signal termination. The signaling of GPCRs and some other TMRs is controlled by a family of intracellular proteins called arresting. GPCRs are an example of transmembrane receptors which bind arrestin, activate signaling, and the like. Arrestins bind activated GPCRs, including those that have been agonist-activated and especially those that have been phosphorylated by G protein-coupled receptor kinases (GRKs).

Receptors, including GPCRs, have historically been targets for drug discovery and therapeutic agents because they bind ligands, hormones, and drugs with high specificity. Approximately fifty percent of the therapeutic drugs in use today target or interact directly with GPCRs. See e.g., Jurgen Drews, (2000) "Drug Discovery: A Historical Perspective," Science 287:1960-1964.

TMRs, of which GPCRs are but one example, may be useful in the methods described herein.

TMRs and Signaling

TMRs, or GPCRs, can activate intracellular signaling. GPCRs recruit and regulate the activity of intracellular heterotrimeric G proteins. The activated receptor typically induces a conformational change in the associated G protein α-subunit leading to release of GDP followed by binding of GTP. Subsequently, the GTP-bound form of the α-subunit dissociates from the receptor as well as from the stable βγ-dimer. Both the GTP-bound α-subunit and the released βγ-dimer can modulate several cellular signaling pathways. These include, among others, stimulation or inhibition of adenylate cyclases and activation of phospholipases, as well as regulation of potassium and calcium channel activity. GPCRs also may not solely act via heterotrimeric G proteins.

Transmembrane Receptors (TMRs) and Internalization

Internalized TMRs, or GPCRs, are not responsive to agonists or ligands.

Subsequent to agonist or ligand exposure, initial steps of internalization produce attenuation of the signaling ability of the TMR or GPCR that may involve uncoupling of the GPCR from its cognate heterotrimeric G-protein. The cellular mechanism mediating initial steps of agonist-specific internalization is a two-step process in which agonist-occupied receptors are phosphorylated by a kinase, for example a GPCR kinase (GRK), and then bind an arrestin protein. TMRs, of which GPCRs are but one example, may bind an arrestin protein, and subsequently be internalized. The type III TGF-beta receptor is an example of a TMR, other than a GPCR, that binds arrestin, and undergoes subsequent internalization and signaling down-regulation (Chen et al., 2003, Science 301:1394-1397).

It is known, for example, that after agonists bind GPCRs, G-protein coupled receptor kinases (GRKS) phosphorylate intracellular domains of GPCRs. After phosphorylation, an arrestin protein associates with the GRK-phosphorylated receptor and uncouples the receptor from its cognate G protein. The interaction of the arrestin with the phosphorylated GPCR terminates GPCR signaling, initiates internalization, and produces a non-signaling receptor.

The arrestin bound to the GPCR targets the GPCR to claibrin-coated pits or other cellular machinery for endocytosis (i.e., internalization) by functioning as an adaptor protein, which links the GPCR to components of the endocytic machinery, such as adaptor protein-2 (AP-2) and clathrin. The internalized GPCRs are dephosphorylated and are recycled back to the cell surface, or are retained within the cell and degraded. The stability of the interaction of arrestin with the GPCR is one factor that dictates the rate of GPCR dephosphorylation, and recycling. The involvement of GPCR phosphorylation and dephosphorylation in the internalization process has been exemplified in U.S. Ser. No. 09/933,844, filed Nov. 5, 2001, now U.S. Pat. No. 6,459,604, the disclosure of which is hereby incorporated by reterence in its entirety.

There is a need for methods to identify compounds that can activate TMR signaling, or GPCR signaling, with reduced internalization of the TMR. Such compounds have increased signaling with decreased signal termination.

SUMMARY

The present invention relates to methods of identifying a compound that activates TMR signaling with reduced internalization of the TMR. Considering the importance of modulation of TMR, or GPCR, activity in drug discovery and disease treatment, these methods for the identification of these compounds satisfies a great need.

This disclosure relates to methods of identifying a compound that activates TMR signaling with reduced internalization of the TMR.

BRIEF DESCRIPTION OF DRAWINGS

The objects and advantages of the invention will be understood by reading the following detailed description in conjunction with the drawings in which:

FIG. 1 is a list of GPCRs that may be used with the present invention.

FIG. 2 is a list of certain Class A and Class B GPCRs (A1 adenosine receptor (SEQ ID NO:03), adrenegic, alpha-1B-, receptor (SEQ ID NO:04), adrenergic alpha-2A receptor, (SEQ ID NO:05), alpha-2B-adrenergic receptor, (SEQ ID NO:06), alpha-2C-adrenergic receptor,(SEQ ID NO:07), beta-1-adrenergic receptor, (SEQ ID NO:08), beta-2-adrenergic receptor, (SEQ ID NO:09), dopamine receptor D1 (SEQ ID NO:10), D(2) dopamine receptor (SEQ ID NO:11), d3 dopamine receptor (SEQ ID NO:12), dopamine receptor D4 (SEQ ID NO:13), dopamine receptor D5 (SEQ ID NO:14), muscarinic acetycholine receptor M1 (SEQ ID NO:15), muscarinic acetylcholine receptor M2 (SEQ ID) NO:16), muscarinic acetylcholine receptor M3 (SEQ ID NO:17), muscarinic acetylcholine receptor M4 (SEQ ID NO:18), m5 muscarinic receptor (SEQ ID NO:19), 5-hydroxtryptamine (serotonin) receptor 1A (SEQ ID NO:20). 5-hydroxytryptamine (serotonin) receptor 1B (SEQ ID NO:21), 5-hydroxytryptamine (serotonin) receptor 1E (SEQ ID NO:22), olfactory receptor 6A1 (SEQ ID NO:23), olfactory receptor 2C1 (SEQ ID NO:24), angiotensin receptor 1 (SEQ ID NO:25), angiotensin receptor 2 (SEQ ID NO:26), interlukin 8 receptor beta (SEQ ID NO:27), cx3c chemokine receptor 1 (SEQ ID NO:28), neurotensin receptor (SEQ ID NO:29), substance-p receptor (SEQ ID NO:30), vasopressin receptor type 2 (SEQ ID NO:31), thyrotropin-releasing hormone receptor (SEQ ID NO:32), oxytocin receptor (SEQ ID NO:33), neuromedin U receptor 1 (SEQ ID NO:34), gastrin receptor (SEQ ID NO:35), galanin receptor 3 (SEQ ID NO:36), edg-1 (SEQ ID NO:37), central canabinoid receptor (SEQ ID NO:38), delta onpoid receptor (SEQ ID NO:39), protinase activated receptor 2 (SEQ ID NO:40), and vasopressive intestinal peptide receptor (SEQ ID NO:41)).

FIG. 3 lists some GPCR agonists or ligands useful in the present invention.

FIGS. 4A-L depict the dose response curves for human GPCR signaling and translocation in CHO cells, in the presence of compounds 1-12, for 30 min, 60 min, and 120 min, in one experiment. FIGS. 4M-X depict the dose response curves for human GPCR signaling and translocation in CHO cells, in the presence of compounds 1-12, for 30 min, 60 min, and 120 min, in a second experiment.

FIGS. 5A-L depict the dose response curves for human GPCR signaling and translocation in U2OS cells, in the presence of compounds 1-12, for 30 min, 60 min, and 120 min, in one experiment. FIGS. 5M-X depict the dose response curves for human GPCR signaling and translocation in U2OS cells, in the presence of compounds 1-12, for 30 min, 60 min, and 120 min, in a second experiment.

FIGS. 6A-L depict the dose response curves for rat GPCR signaling and translocation in CHO cells, in the presence of compounds 1-12, for 30 min, 60 min, and 120 min, in one experiment. FIGS. 6M-X depict the dose response curves for rat GPCR signaling and translocation in CHO cells, in the presence of compounds 1-12, for 30 min, 60 min, and 120 min, in a second experiment.

FIGS. 7A-L depict the dose response curves for rat GPCR signaling and translocation in U2OS cells, in the presence of compounds 1-12, for 30 min, 60 min, and 120 min, in one experiment. FIGS. 7M-X depict the dose response curves for rat GPCR signaling and translocation in U2OS cells, in the presence of compounds 1-12, for 30 min, 60 min, and 120 min, in a second experiment.

FIG. 8A depicts the dose response curves for MOR signaling and translocation in U2OS cells, in the presence of DAMGO, for 30 min, 60 min, and 120 min, expressed as a % of the maximum response in the presence of morphine. FIG. 8B depicts the dose response curves for MOR signaling and translocation in U2OS cells, in the presence of morphine, for 30 min, 60 min, and 120 min, expressed as a % of the maximum response in the presence of morphine. FIG. 8C depicts the dose response curves for MOR signaling and translocation in U2OS cells, in the presence of DAMGO, for 30 min, 60 min, and 120 min, expressed as a % of the maximum response in the presence of DAMGO. FIG. 8D depicts the dose response curves for MOR signaling and translocation in U2OS cells, in the presence of morphine, for 30 min, 60 min, and 120 min, expressed as a % of the maximum response in the presence of DAMGO.

DETAILED DESCRIPTION

In accordance with the present invention there may be employed conventional molecular biology, microbiology, immunology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-II [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (2000)]; "Immobilized Cells And Enzymes" [IRL Press, (1986)]; B. Perbal, "A Practical Guide To Molecular Cloning" (1984); *Using Antibodies: A Laboratory Manual: Portable Protocol No. I*, Harlow, Ed and Lane, David (Cold Spring Harbor Press, 1998); *Using Antibodies: A Laboratory Manual*, Harlow, Ed and Lane, David (Cold Spring Harbor Press, 1999).

Unless otherwise stated, the following terms used in the specification and claims have the meanings given below:

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

"Arrestin" means all types of naturally occurring and engineered variants of arrestin, including, but not limited to, visual arrestin (sometimes referred to as Arrestin 1), cone arrestin (sometimes referred to as arrestin-4), β-arrestin 1 (sometimes referred to as Arrestin 2), and β-arrestin 2 (sometimes referred to as Arrestin 3). Modified arresting, for example arrestins that constitutively bind TMRs or GPCRs, are included.

"βAR" is a GPCR termed a β-adrenergic receptor.

"Carboxyl-terminal tail" means the carboxyl-terminal tail of a GPCR following membrane span 7. The carboxyl-terminal tail of many GPCRs begins shortly after the conserved NPXXY motif that marks the end of the seventh transmembrane domain (i.e. what follows the NPXXY motif is the carboxyl-terminal tail of the GPCR). The carboxyl-terminal tail may be relatively long (approximately tens to hundreds of amino acids), relatively short (approximately tens of amino acids), or virtually non-existent (less than approximately ten amino acids). As used herein, "carboxyl-terminal tail" shall mean all three variants (whether relatively long, relatively short, or virtually non-existent), and may or may not contain palmitoylated cysteine residue(s).

"Class A receptors" preferably do not translocate together with arrestin proteins to endocytic vesicles or endosomes in association with arrestin-GFP in HEK-293 cells.

"Class B receptors" preferably do translocate together with arrestin proteins to endocytic vesicles or endosomes associated with arrestin-GFP in HEK-293 cells.

"Detectable molecule" or "tag" or "label" means any molecule capable of detection by spectroscopic, photochemical, biochemical, immunochemical, electrical, radioactive, and optical means, including but not limited to, fluorescence, phosphorescence, and bioluminescence and radioactive decay. Detectable molecules include, but are not limited to, GFP, luciferase, β-galactosidase, rhodamine-conjugated antibody, and the like. Detectable molecules include radioisotopes, epitope tags, affinity labels, enzymes, fluorescent groups, chemiluminescent groups, and the like. Detectable molecules include molecules which are directly or indirectly detected as a function of their interaction with other molecule(s). Detectable molecules may be used to detect cellular molecules which are otherwise difficult to detect. For example, if detectably labeled, arrestin or a GPCR can be easily detected. The detectable label can be used to determine the localization of the labeled molecule. For example, detectably labeled arrestin or GPCR facilitates the determination of the localization of the molecule, or related molecules, in the plasma membrane, pits, cytosol, endocytic vesicles, or endosomes, for example.

"GFP" means Green Fluorescent Protein which refers to various naturally occurring forms of GFP which may be isolated from natural sources or genetically engineered, as well as artificially modified GFPs. GFPs are well known in the art. See, for example, U.S. Pat. Nos. 5,625,048; 5,777,079; and 6,066,476. It is well understood in the art that GFP is readily interchangeable with other fluorescent proteins, isolated from natural sources or genetically engineered, including but not limited to, yellow fluorescent proteins (YFP), red fluorescent proteins (RFP), cyan fluorescent proteins (CFP), blue fluorescent proteins, luciferin, UV excitable fluorescent proteins, or any wave-length in between. As used herein, "GFP" shall mean all fluorescent proteins known in the art.

"Unknown or Orphan Receptor" means a TMR, or a GPCR, whose function and/or ligands are unknown.

Amino acid substitutions may also be introduced to substitute an amino acid with a particularly preferable property. For example, a Cys may be introduced a potential site in order to allow formation of disulfide bridges with another Cys. A His may be introduced as a particularly "catalytic" residue (i.e., His can act as an acid or base and is the most common amino acid in biochemical catalysis). Pro may be introduced because of its particularly planar structure, which induces β-turns in the protein's structure.

Two amino acid sequences are "substantially homologous" when at least about 70% of the amino acid residues (preferably at least about 80%, and most preferably at least about 90 or 95%) are identical, or represent conservative substitutions.

"Antagonist(s)" include all agents that interfere with wild-type and/or modified TMR, or GPCR, binding to an agonist, wild-type and/or modified TMR, or GPCR, internalization, wild-type and/or modified TMR, or GPCR, binding arrestin, wild-type and/or modified TMR, or GPCR, endosomal localization, internalization, and the like, including agents that affect the wild-type and/or modified TMRs, including GPCRs, as well as agents that affect other proteins involved in wild-type and/or modified TMR, or GPCR, signaling, internalization, endosomal localization, and the like.

"Modified GPCR" or "modified TMR" means a GPCR or TMR that has one or more modifications in the amino acid sequence. As such, the GPCR or TMR may be modified in whole or in part. These modifications in the amino acid sequence include mutations of one or more amino acids, insertion of one or more amino acids, deletion of one or more amino acids, and substitutions of one or more amino acids in which one or more amino acids are deleted and one or more amino acids are added in place of the deleted amino acids. Such modified GPCRs are described herein, as well as in U.S. Ser. No. 09/993,844 and U.S. Ser. No. 10/054,616, which are incorporated herein by reference in their entireties.

"GPCR" means G protein-coupled receptor and includes GPCRs naturally occurring in nature, as well as GPCRs which have been modified.

"TMR" means transmembrane receptor and includes TMRs naturally occurring in nature, as well as TMRs which have been modified. GPCRs are an example of TMRs.

"Internalized TMR" means a TMR that has undergone internalization. The internalized TMR may be located at any point in the internalization pathway. It presently does not have ability to bind to agonist and activate conventional signaling. The TMR may be a GPCR. The signaling may be G protein signaling.

"Internalization pathway" means any cellular component of the internalization process, as well as any cellular structure implicated in the internalization process and subsequent processes, including but not limited to, arresting, GRKs, GPCRs, AP-2 protein, clathrin, protein phosphatases, and the like. In the methods of assaying of the present invention, the polypeptides may be detected, for example, in the cytoplasm, at a cell membrane, in clathrin-coated pits, in endocytic vesicles, endosomes, any stages in between, and the like.

"TMR signaling" means TMR induced activation of signaling. This may result in, for example, cAMP production. The TMR may be a GPCR. The signaling may be G protein signaling.

"G protein-coupled receptor kinase" (GRK) includes any kinase that has the ability to phosphorylate a GPCR. Splice variants, biologically active fragments, modified GRKs, and GRKs from animals and other organisms are included.

"*Homo sapiens* TMR" means a naturally occurring TMR in a *Homo sapiens*. The TMR may be a GPCR.

"Naturally occurring TMR" means a TMR that is present in nature. The TMR may be a GPCR.

"Odorant ligand" means a ligand compound that, upon binding to a receptor, leads to the perception of an odor including a synthetic compound and/or recombinantly produced compound including agonist and antagonist molecules.

"Odorant receptor" means a receptor protein normally found on the surface of olfactory neurons which, when activated (normally by binding an odorant ligand) leads to the perception of an odor.

"Modulation" includes at least an up-regulation or down-regulation of the expression, or an increase or decrease in activity of a protein. Modulation of a protein includes the up-regulation, down-regulation, increase or decrease in activity of a protein or compound that regulates a protein. Modulation also includes the regulation of the gene, the mRNA, or any other step in the synthesis of the protein of interest.

An "overexpressed" protein refers to a protein that is expressed at levels greater than wild-type expression levels.

"Modified GRK" means a GRK that has one or more modifications in the amino acid sequence at the C-terminus of the GRK. The modified GRK constitutively localizes to the plasma membrane. Preferably, the GRK is modified by the addition of a CAAX motif.

"CAAX" motif means a four amino acid sequence, wherein C is cysteine; A is an aliphatic amino acid; and X is the C-terminal amino acid of the protein.

A "constitutive" activity means an activity that occurs in the absence of agonist. For example, the modified GRK constitutively localizes to the plasma membrane means that the modified GRK localizes to the plasma membrane in the absence of agonist.

"Reduced Internalization" means that the TMR, or GPCR, internalization is reduced or delayed as compared with the TMR, or GPCR, internalization activated by a control compound. The control compound may be a natural agonist or natural ligand of the TMR, but may be any other compound used as a control. Reduced internalization may be demonstrated by a number of factors. For example, reduced internalization may be demonstrated by a decrease in the Max of internalization of the receptor as compared to the internalization stimulated by a natural agonist or natural ligand of the TMR. In another example, reduced internalization may be demonstrated by an increase in the EC50 of internalization of the TMR as compared to the internalization stimulated by a natural agonist or natural ligand of the TMR. In a further example, if the amount of compound required to activate internalization is greater than the amount of natural agonist or natural ligand required to activate internalization, then the internalization would be reduced. In yet another example, if the length of time that the TMR is required to be exposed to the compound in order to activate internalization is greater than the length of time that the TMR is required to be exposed to a natural agonist or natural ligand in order to activate internalization, then the internalization would be reduced.

"EC50" represents the median effective concentration of a compound; the smallest concentration required to produce 50% of a maximal stated effect.

The "stated effect" means the effect of interest. The stated effect, for example, may be activation of signaling, inhibition of signaling, amount of signaling, activation of internalization, inhibition of internalization, amount of internalization, or ligand binding.

A "Max" represents the maximal stated effect. The Max may be empirically determined or extrapolated. Bmax and Vmax are examples of Max. For example, Max may be the maximal response as plotted on a response curve. For example, in a measurement of signaling, cAMP production may be plotted with respect to different concentrations of a test compound to yield a dose response curve; the Max represents the maximal cAMP production on the dose response curve. As an additional example, in a measurement of translocation, translocation may be plotted with respect to different concentrations of a test compound to yield a dose response curve; the Max represents the maximal translocation on the dose response curve.

A "control" compound is a compound against which the test compound is compared. Preferably, the control compound in the present invention may activate and internalize a TMR, or a GPCR. Preferably, the control compound may be an agonist or ligand of a TMR, or a GPCR.

A "dose response curve" represents a stated effect in the presence of different concentrations of a compound. In the dose response curves in the present invention, the stated effect is preferably the signaling or internalization of a TMR, or a GPCR.

"Measuring translocation of a TMR" means detection of the localization of a TMR in a cell. The TMR may be a GPCR. Preferably, the TMR, or GPCR, is detected by visualizing the TMR, arrestin, GRK, or another molecule. The molecule to be detected may be detectably labeled. Examples of detectably labeled molecules are described herein. Preferably, the molecule is localized at the cell membrane, in pits, endosomes, endocytic vesicles, and/or in the cytosol. Methods of monitoring translocation include Transfluor, BRET, FRET, polarization microscopy, evanescent wave excitation microscopy, and standard or confocal microscopy. Useful TMRs, GPCRs, methods, and methods of detection, for example, are as described herein, in U.S. Ser. No. 08/869,568 (now Issued U.S. Pat. No. 5,891,646), Ser. No. 09/233,530 (now Issued U.S. Pat. No. 6,110,693), Ser. No. 09/469,554 (now Issued U.S. Pat. No. 6,528,271), Ser. Nos. 10/054,616, 09/993,844, 10/095,620, 10/101,235, 09/631,468, 10/141,725 now U.S. Pat. No. 7,138,240, Ser. Nos. 10/161,916, 09/772,644 now U.S. Pat. No. 6,770,449, Ser. Nos. 10/336,276, 60/421,538, 60/442,403, 60/470,325, 60/401,698, 60/275,339, 60/263,406, 60/245,772, 60/260, 363, 60/295,945, 60/393,789, and 60/379,986, and PCT applications PCT/US03/20838, and PCT/US03/14581 which are incorporated by reference herein.

"Quantitatively determining" internalization can include any analytical method of measuring amount of TMR or GPCR internalization, including for example measuring the intensity of pixels, amount of fluorescence, EC50, Max, dose response curve, or any other quantitative analysis for comparison known to those of skill in the art. Examples of quantitatively determining internalization are described herein. Various methods of detection, including but not limited to those as described herein, may be used for quantitatively determining internalization.

A "TMRA" means a transmembrane receptor (TMR) agonist, which is capable of activating TMR signaling while exhibiting reduced TMR internalization over a control compound. The internalization is reduced if the TMR internalization in the presence of the test compound is reduced as compared to the TMR internalization in the presence of a control compound. The signaling is activated if the TMR signaling in the presence of the test compound is activated as compared to in the absence of agonist.

There is a need for methods of identifying a compound that activates TMR or GPCR signaling with reduced internalization of the TMR or GPCR. Such a compound may increase signaling in response to a given dose of compound, decrease signal termination, and maintain responsiveness of a given TMR or GPCR to a given dose of compound.

The present invention relates to methods of screening for a TMRA. Methods of determining if a compound activates signaling but has altered internalization properties are included.

TMRAs are useful for a variety of reasons. While compounds which activate signaling and also activate internalization pathways are known, many of these have less than desirable characteristics, including certain side effects. Increased internalization of TMRs would result in fewer receptors available at the membrane or cell surface for interaction with agonist, which may be over repeated dosage. Reduced internalization of TMRs would result in more receptors available at the membrane or cell surface for interaction with agonist or TMRA. This reduced internalization may decrease the amount and/or frequency of agonist or TMRA that is necessary to activate signaling. Methods of identifying TMRAs are necessary. Methods of identifying these compounds would be useful in the treatment of numerous diseases.

The present invention utilizes quantitative measurements of internalization. The quantitative measurements of internalization are necessary in the methods of identifying reduced internalization agonists as described herein.

Methods of Quantitating TMR Signaling

TMR or GPCR signaling may be quantitated by any of a number of indicators of TMR or GPCR signaling. These include quantitating the activity of members of any of a number of signaling pathways, GPCR dimerization, and the like. As used herein, a "signaling pathway" refers to the modulation (e.g., stimulation or inhibition) of a cellular function/activity upon the binding of a ligand to the TMR or GPCR. Examples of such functions include mobilization of intracellular molecules that participate in a signal transduction pathway, e.g., phosphatidylinositol 4,5-bisphosphate, inositol 1,4,5-triphosphate, and adenylate cyclase; polarization of the plasma membrane; production or secretion of molecules; alteration in the structure of a cellular component; cell proliferation, e.g., synthesis of DNA; cell migration; cell differentiation; and cell survival.

The specific pathway to be measured may depend on the specific TMR or GPCR of interest. Many methods of quantitating the activity of members of signaling pathways are known to one of skill in the art.

When screening for bioactivity of compounds, intracellular second messenger generation can be measured directly. A variety of intracellular effectors have been identified as being G-protein-regulated, including cAMP, cyclic GMP, Calcium, a lipid, phosphatidylinositol, a hydrogen ion, an ion transport molecule, and the like. In addition, G proteins interact with a range of ion channels and are able to inhibit certain voltage-sensitive $Ca^{++}$ transients, as well as stimulating cardiac $K^+$ channels. Additionally, enzymes such as adenylyl cyclase, phosphodiesterase, phospholipase C, protein kinase, phospholipase $A_2$, and the like may be measured.

In one embodiment, the GTPase enzymatic activity by G proteins can be measured in plasma membrane preparations by determining the breakdown of $\gamma^{32}$ P GTP using techniques that are known in the art (For example, see Signal Transduction: A Practical Approach. G. Milligan, Ed. Oxford University Press, Oxford England). When receptors that modulate cAMP are tested, it will be possible to use standard techniques for cAMP detection, such as competitive assays which quantitate $[^3H]$cAMP in the presence of unlabelled cAMP.

"Cyclic AMP turnover and metabolism", the molecules involved in the turnover and metabolism of cyclic AMP (cAMP) as well as to the activities of these molecules, can be measured. Cyclic AMP is a second messenger produced in response to ligand-induced stimulation of certain TMRs or G protein coupled receptors. In the cAMP signaling pathway, binding of a ligand to a TMR or GPCR can lead to the activation of the enzyme adenyl cyclase, which catalyzes the synthesis of cAMP. The newly synthesized cAMP can in turn activate a cAMP-dependent protein kinase. This activated kinase can phosphorylate a voltage-gated potassium channel protein, or an associated protein, and lead to the inability of the potassium channel to open during an action potential. The inability of the potassium channel to open results in a decrease in the outward flow of potassium, which normally repolarizes the membrane of a neuron, leading to prolonged membrane depolarization.

Certain receptors stimulate the activity of phospholipase C which stimulates the breakdown of phosphatidylinositol 4,5, bisphosphate to 1,4,5-$IP_3$ (which mobilizes intracellular Ca++) and diacylglycerol (DAG) (which activates protein kinase C). Inositol lipids can be extracted and analyzed using standard lipid extraction techniques. DAG can also be measured using thin-layer chromatography. Water soluble derivatives of all three inositol lipids (IP1, IP2, IP3) can also be quantitated using radiolabelling techniques or HPLC.

"Phosphatidylinositol turnover and metabolism", the molecules involved in the turnover and metabolism of phosphatidylinositol 4,5-bisphosphate ($PIP_2$) as well as to the activities of these molecules, can also be measured. $PIP_2$ is a phospholipid found in the cytosolic leaflet of the plasma membrane. Binding of ligand to the receptor activates, in some cells, the plasma-membrane enzyme phospholipase C that in turn can hydrolyze $PIP_2$ to produce 1,2-diacylglycerol (DAG) and inositol 1,4,5-triphosphate ($IP_3$). Once formed $IP_3$ can diffuse to the endoplasmic reticulum surface where it can bind an $IP_3$ receptor, e.g., a calcium channel protein containing an $IP_3$ binding site. $IP_3$ binding can induce opening of the channel, allowing calcium ions to be released into the cytoplasm. $IP_3$ can also be phosphorylated by a specific kinase to form inositol 1,3,4,5-tetraphosphate ($IP_4$), a molecule which can cause calcium entry into the cytoplasm from the extracellular medium. $IP_3$ and $IP_4$ can subsequently be hydrolyzed very rapidly to the inactive products inositol 1,4-biphosphate ($IP_2$) and inositol 1,3,4-triphosphate, respectively. These inactive products can be recycled by the cell to synthesize $PIP_2$. The other second messenger produced by the hydrolysis of $PIP_2$, namely 1,2-diacylglycerol (DAG), remains in the cell membrane where it can serve to activate the enzyme protein kinase C. Protein kinase C is usually found soluble in the cytoplasm of the cell, but upon an increase in the intracellular calcium concentration, this enzyme can move to the plasma membrane where it can be activated by DAG. The activation of protein kinase C in different cells results in various cellular responses such as the phosphorylation of glycogen synthase, or the phosphorylation of various transcription factors, e.g., NF-kB. The language "phosphatidylinositol activity", as used herein, refers to an activity of $PIP_2$ or one of its metabolites.

The mobilization of intracellular calcium or the influx of calcium from outside the cell can be measured using standard techniques. The choice of the appropriate calcium indicator, fluorescent, bioluminescent, metallochromic, or Ca++-sensitive microelectrodes depends on the cell type and the magnitude and time constant of the event under study (Borle (1990) Environ Health Perspect 84:45-56). As an exemplary method of Ca++detection, cells could be loaded with the Ca++sensitive fluorescent dye fura-2 or indo-1, using standard methods, and any change in Ca++measured using a fluorometer.

Another exemplary high throughput calcium assay involves induction of a reporter gene operatively linked to a calcium-responsive promoter. In this method, a calcium flux resulting from the activation of a TMR or GPCR turns on the promoter which subsequently drives the expression of a reporter gene encoding a protein with an enzymatic activity that can be easily detected, preferably by a colorimetric or fluorescent assay. Commonly used reporter proteins include: β-galactosidase, β-lactamase, chloramphenicol acetyltransferase (CAT), luciferase, green fluorescent protein (GFP) and its derivatives, among others. Reporter proteins can also be linked to other proteins whose expression is dependent upon the stimulation of TMRs or GPCRs. An illustrative example would be a fusion protein comprising luciferase sequence in frame with the open-reading frame of nuclear factor of activated T cells (NFAT). Since the transcription of NFAT requires the co-activation of calcium and protein kinases C signaling pathways acting downstream of TMRs or GPCRs, an effective coupling of heterotrimeric G protein to the receptors can then be measured by assaying NFAT-mediated luciferase activity. This system has been employed to demonstrate a carbachol dependent luciferase response in cells co-expressing muscarinic m3 receptor and chimeric $α_q$ mutant i5q (Boss et al., J. Biol. Chem., 271: 10429-10482, 1996). In practice of this method, a preferred host cell is one of lymphoid or neuronal origin, such as Jurkat cells and pheochromocytoma PC12 cells. However, the choice of host cells is not limited to these two types, as NFAT and NFAT isoforms are present in a variety of cells including endothelial and myeloid cells (id).

Reporter gene based assays of this invention measure the end stage of the above described cascade of events, e.g., transcriptional modulation. Accordingly, in practicing one embodiment of the assay, a reporter gene construct is inserted into the reagent cell in order to generate a detection signal dependent on receptor signaling. Typically, the reporter gene construct will include a reporter gene in operative linkage with one or more transcriptional regulatory elements responsive to the signal transduction activity of the target receptor, with the level of expression of the reporter gene providing the receptor-dependent detection signal. The amount of transcription from the reporter gene may be measured using any method known to those of skill in the art to be suitable. For example, specific mRNA expression may be detected using Northern blots or specific protein product may be identified by a characteristic stain or an intrinsic activity.

Also, the activation of phospholipase A2 can easily be quantitated using known techniques, including, for example, the generation of arachadonate in the cell.

In the case of certain receptors, it may be desirable to screen for changes in cellular phosphorylation. Such assay formats may be useful when the receptor of interest is a receptor tyrosine kinase. For example, yeast transformed with the FGF receptor and a ligand which binds the FGF receptor could be screened using colony immunoblotting (Lyons and Nelson (1984) Proc. Natl. Acad. Sci. USA 81:7426-7430) using anti-phosphotyrosine. In addition, tests for phosphorylation could be useful when a receptor which may not itself be a tyrosine kinase, activates protein kinases that function downstream in the signal transduction pathway. Likewise, it is noted that protein phosphorylation also plays a critical role in cascades that serve to amplify signals generated at the receptor. Multi-kinase cascades allow not only signal amplification but also signal divergence to multiple effectors that are often cell-type specific, allowing a growth factor to stimulate mitosis of one cell and differentiation of another.

One such cascade is the MAP kinase pathway that appears to mediate both mitogenic, differentiation and stress responses in different cell types. Stimulation of growth factor receptors results in Ras activation followed by the sequential activation of c-Raf, MEK, and p44 and p42 MAP kinases (ERK1 and ERK2). Activated MAP kinase then phosphorylates many key regulatory proteins, including p90 RSK and Elk-1 that are phosphorylated when MAP kinase translocates to the nucleus. Homologous pathways exist in mammalian and yeast cells. For instance, an essential part of the S. cerevisiae pheromone signaling pathway is comprised of a protein kinase cascade composed of the products of the STE11, —STE7, and FUS3/KSS1 senes (the latter pair are distinct and functionally redundant). Accordingly, phosphorylation and/or activation of members of this kinase cascade can be detected and used to quantitate receptor engagement. Phosphotyrosine specific antibodies are available to measure increases in tyrosine phosphorylation and phospho-specific antibodies are commercially available (New England Biolabs, Beverly, Mass.).

The response mediated by the receptor protein depends on the type of cell. For example, in some cells, binding of a ligand to the receptor protein may stimulate an activity such as release of compounds, gating of a channel, cellular adhesion, migration, differentiation, etc., through phosphatidylinositol or cyclic AMP metabolism and turnover while in other cells, the binding of the ligand will produce a different result. Regardless of the cellular activity/response modulated by the receptor protein, it is universal that the protein is a TMR or GPCR and interacts with G proteins to produce one or more secondary signals, in a variety of intracellular signal transduction pathways, e.g., through phosphatidylinositol or cyclic AMP metabolism and turnover, in a cell.

The signaling assays may use spectrally-encoded assay bead systems. More than one measure of TMR or GPCR activation may be determined; they may be measured, for example, sequentially or in parallel.

Modified methods for detecting receptor-mediated signal transduction exist and one of skill in the art will recognize suitable methods that may be used to substitute for the example methods listed.

Methods of Measuring Internalization

Methods of detecting internalization are useful in the methods of the present invention. Such methods that are detected quantitatively are preferred. Methods that are optically detectable and quantitatable are preferred. Any method that will measure internalization of the TMR or GPCR by monitoring the localization of the TMR or GPCR or any molecule that interacts with the TMR or GPCR in the internalization pathway may be used. Examples include Transfluor, BRET, FRET.

Certain methods of detection useful in the present invention are described in U.S. Pat. No. 5,891,646, U.S. Pat. No. 6,110,693, U.S. Ser. No. 09/631,468, U.S. Ser. No. 10/141,725 U.S. Pat. No. 7,138,240, U.S. Ser. Nos. 10/161,916, 09/469,554 U.S. Pat. No. 6,528,271, U.S. Ser. No. 09/772,644 U.S. Pat. No. 6,770,449, U.S. Ser. No. 09/993,844 U.S. Pat. No. 7,018,812, U.S. Ser. No. 10/054,616, U.S. Ser. No. 10/095,620, U.S. Ser. No. 10/101,235, U.S. provisional application 60/393,789, U.S. provisional application 60/379,986, and U.S. provisional application 60/401,698, which are hereby incorporated by reference in their entireties. Other methods useful in the present invention are described in U.S. Ser. No. 09/759,152 U.S. Pat. No. 6,800,445, U.S. Ser. No. 09/654,499 U.S. Pat. No. 6,893,827, WO 99/66324, WO 01/46691, WO 01/46694, WO 98/00715, and WO 02/46763.

Methods of detecting the intracellular location of the detectably labeled arrestin, the intracellular location of a detectably labeled TMR or GPCR, or interaction of the detectably labeled arrestin, or other member of a TMR or GPCR/arrestin complex with a TMR or GPCR or any other cell structure, including for example, the concentration of arrestin or TMR or GPCR at a cell membrane, colocalization of arrestin with TMR or GPCR in endosomes, and concentration of arrestin or TMR or GPCR in clathrin coated pits, and the like, will vary dependent upon the detectable molecule(s) used.

One skilled in the art readily will be able to devise detection methods suitable for the detectable molecule(s) used. For optically detectable molecules, any optical method may be used where a change in the fluorescence, bioluminescence, or phosphorescence may be measured due to a redistribution or reorientation of emitted light. Such methods include, for example, polarization microscopy, BRET, FRET, evanescent wave excitation microscopy, and standard or confocal microscopy.

In a preferred embodiment arrestin may be conjugated to GFP and the arrestin GFP conjugate may be detected by confocal microscopy. In another preferred embodiment, arrestin may conjugated to a GFP and the TMR or GPCR may be conjugated to an immunofluorescent molecule, and the conjugates may be detected by confocal microscopy. In an additional preferred embodiment, arrestin may be conjugated to a GFP and the carboxy terminus of the TMR or GPCR may be conjugated to a luciferase and the conjugates may be detected by bioluminescence resonance emission technology. In a further preferred embodiment arrestin may be conjugated to a luciferase and TMR or GPCR may be conjugated to a GFP, and the conjugates may be detected by bioluminescence resonance emission technology. In a further preferred embodiment, arrestin may be conjugated to a detectable molecule fragment (or portion, domain, and the like), TMR or GPCR may be conjugated to a detectable molecule fragment (or portion, domain, and the like), and the interaction of the two fragments can be detected. In a further preferred embodiment, the TMR or GPCR or arrestin may be labeled with a detectable molecule which is specifically detectable upon localization at certain cellular locations. The methods of the present invention are directed to detecting TMR or GPCR activity. The methods of the present invention allow enhanced monitoring of the GPCR pathway in real time.

In a preferred embodiment, the localization pattern of the detectable molecule is determined. In a further preferred embodiment, alterations of the localization pattern of the detectable molecule may be determined. The localization pattern may indicate cellular distribution of the detectable molecule. Certain methods of detection are described in U.S. Ser. No. 10/095,620, filed Mar. 12, 2002, which claims priority to U.S. Provisional Patent Application No. 60/275,339, filed Mar. 13, 2001, the contents of which are incorporated by reference in their entirety. The quantitation of the detectable molecules is also described in U.S. Ser. No. 10/161,916.

Molecules may also be detected by their interaction with another detectably labeled molecule, such as an antibody.

Additional methods of quantitating internalization may be used in accordance with the present invention.

Methods of Identifying a Compound that Modulates a TMR or GPCR Signaling and/or Internalization Response A method of identifying a TMRA is described below. The TMRA is capable of activating TMR signaling while reducing TMR internalization. The method includes providing a cell including at least one TMR or a biologically active fragment thereof. The cell may also include arrestin or biologically active fragments thereof, and/or GRK or biologically active fragments thereof. A component or components of the cell may be detectably labeled. The label may be detectable as the result of an interaction with another detectably labeled molecule, or the like. The detectably labeled molecule may be detected at the plasma membrane, in endosomes, endocytic vesicles, or in the cytosol, for example. The detectable molecule may be a radioisotope, an epitope tag, an affinity label, an enzyme, a fluorescent group, or a chemiluminescent group, for example. The method may include the additional steps of providing a agonist or ligand of a TMR, and modifying the agonist or ligand, for example.

The TMR may be a GPCR. Certain GPCRs useful in the present invention are listed in FIG. 1. The GPCR may be a class A receptor, a class B receptor, a µ opioid, $\beta_1$AR, $\beta_2$AR, or dopamine receptor, for example. Certain ligands or agonists useful in the present invention are listed in FIG. 3, for example.

The compound may be a modified natural ligand or natural agonist. The compound may be a known pharmaceutically relevant compound, or may be derived from a known pharmaceutically relevant compound. The cell may be exposed to a compound or compounds. The compound or compounds may be derived from a natural ligand or natural agonist. The compound or compounds may be present in a compound library.

The signaling may be measured. Certain methods of measuring signaling are described herein, but other methods of measuring signaling may also be used. The measurement of the signaling may be useful in a quantitative determination of whether signaling is activated. A dose response curve for signaling may be determined. Signaling may be quantitated by measuring an intracellular effector, wherein said effector may be cAMP, cyclic GMP, Calcium, a lipid, phosphatidylinositol, a hydrogen ion, or an ion transport molecule. Signaling in the presence of the compound may be compared to signaling in the absence of compound to determine if the signaling is activated. The signaling may be activated for a longer time period after stimulation by the TMRA than the length of time of activation after stimulation by the natural ligand or natural agonist.

The internalization may be measured. Certain methods of measuring internalization are described herein, but other methods of measuring internalization may also be used. The measurement of the internalization may be useful in a quantitative determination of whether internalization is reduced. The internalization may be reduced as compared to the TMRA internalization in the presence of a control compound. A dose response curve for signaling may be determined.

Agonists and ligands of TMRs may be modified. Such modifications may result in modified chemical and/or physical properties of the compounds. The modified agonists and ligands may be analyzed by methods of the present invention to identify a TMRA. The modified agonists and ligands may be used to create a panel of compounds. This panel of compounds may be used in the methods as described herein to identify a TMRA.

The TMR or GPCR sequence in a cell of the methods described herein may be a human TMR or GPCR, rat TMR or GPCR, mouse TMR or GPCR, pig TMR or GPCR, primate TMR or GPCR, or a TMR or GPCR from any species. For certain TMRs or GPCRs, the TMR or GPCR from a specific species may be preferred in the methods of the present invention. The methods of the present invention may be repeated; the repeat of method may use cells containing TMRs or GPCRs from different species than in the cells of the first method. A test compound may have TMRA properties in a method using cells including TMRs or GPCRs from a specific species. The same test compound may be a TMRA for TMRs or GPCRs of a certain species, but may or may not be a TMRA for the same TMR or GPCR of a different species. Repeating the methods may be useful to determine the preferred TMR or GPCR species for use in methods using cells containing that TMR or GPCR.

Vectors and Nucleic Acids, Host Cells for Protein Expression

As is well known in the art, DNA sequences may be expressed by operatively linking them to an expression control sequence in an appropriate expression vector and employing that expression vector to transform an appropriate unicellular host. The transforming DNA may or may not be integrated (covalently linked) into chromosomal DNA making up the genome of the cell.

Such operative linking of a DNA sequence of this invention to an expression control sequence, of course, includes, if not already part of the DNA sequence, the provision of an initiation codon, ATG, in the correct reading frame upstream of the DNA sequence.

A wide variety of host/expression vector combinations may be employed in expressing the DNA sequences described herein. Useful expression vectors, for example, may consist of segments of chromosomal, non-chromosomal and synthetic DNA sequences. Suitable vectors include derivatives of SV40 and known bacterial plasmids, e.g., $E.$ $coli$ plasmids col EI, pCR1, pBR322, pMB9 and their derivatives, plasmids such as RP4; phage DNAS, e.g., the numerous derivatives of phage $\lambda$, e.g., NM989, and other phage DNA, e.g., M13 and filamentous single stranded phage DNA; yeast plasmids such as the 2μ plasmid or derivatives thereof; vectors useful in eukaryotic cells, such as vectors useful in insect or mammalian cells; vectors derived from combinations of plasmids and phage DNAS, such as plasmids that have been modified to employ phage DNA or other expression control sequences; and the like.

Any of a wide variety of expression control sequences—sequences that control the expression of a DNA sequence operatively linked to it—may be used in these vectors to express the DNA sequences in this invention. Such useful expression control sequences include, for example, the early or late promoters of SV40, CMV, vaccinia, polyoma or adenovirus, the lac system, the trp system, the TAC system, the TRC system, the LTR system, the major operator and promoter regions of phage $\lambda$, the control regions of fd coat protein, the promoter for 3-phosphoglycerate kinase or other glycolytic enzymes, the promoters of acid phosphatase (e.g., Pho5), the promoters of the yeast α-mating factors, and other sequences known to control the expression of genes of prokaryotic or eukaryotic cells or their viruses, and various combinations thereof.

A wide variety of unicellular host cells are also useful in expressing the DNA sequences described herein. These hosts may include well known eukaryotic and prokaryotic hosts, such as strains of $E.$ $coli,$ $Pseudomonas,$ $Bacillus,$ $Streptomyces$, fungi such as yeasts, plant cells, nematode cells, and animal cells, such as HEK-293, U2OS, CHO, RI.I, B-W and L-M cells, African Green Monkey kidney cells (e.g., COS 1, COS 7, BSC1, BSC40, and BMT10), insect cells (e.g., Sf9), and human cells and plant cells in tissue culture. In one aspect of the present invention, the host cells include a GRK-C20 and an arrestin. In a further aspect of the present invention, the host cells include a GRK, an arrestin, and a GPCR.

It will be understood that not all vectors, expression control sequences and hosts will function equally well to express the DNA sequences described herein.

Neither will all hosts function equally well with the same expression system. However, one skilled in the art will be able to select the proper vectors, expression control sequences, and hosts without undue experimentation to accomplish the desired expression without departing from the scope of this invention. For example, in selecting a vector, the host must be considered because the vector must function in it. The vector's copy number, the ability to control that copy number, and the expression of any other proteins encoded by the vector, such as antibiotic markers, will also be considered.

In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products.

Considering these and other factors a person skilled in the art will be able to construct a variety of vector/expression control sequence/host combinations that will express the DNA sequences described herein on fermentation or in large scale animal culture.

It is further intended that analogs may be prepared from nucleotide sequences of the protein complex/subunit. Analogs, such as fragments, may be produced, for example, by pepsin digestion. Other analogs, such as muteins, can be produced by standard site-directed mutagenesis of coding sequences. Analogs exhibiting biological activity, such as small molecules, whether functioning as promoters or inhibitors, may be identified by known in vivo and/or in vitro assays.

As mentioned above, a DNA sequence can be prepared synthetically rather than cloned. The DNA sequence can be designed with the appropriate codons for the amino acid sequence. In general, one will select preferred codons for the intended host if the sequence will be used for expression. The complete sequence is assembled from overlapping oligonucleotides prepared by standard methods and assembled into a complete coding sequence. See, e.g., Edge, Nature, 292:756 (1981); Nambair et al., Science, 223:1299 (1984); Jay et al., J. Biol. Chem., 259:6311 (1984).

Synthetic DNA sequences allow convenient construction of genes which will express analogs or "muteins". Alternatively, DNA encoding muteins can be made by site-directed mutagenesis of native or modified genes or cDNAs, and muteins can be made directly using conventional polypeptide synthesis.

A general method for site-specific incorporation of unnatural amino acids into proteins is described in Christopher J. Noren, Spencer J. Anthony-Cahill, Michael C. Griffith, Peter G. Schultz, Science, 244:182-188 (April 1989). This method may be used to create analogs with unnatural amino acids.

Additional motifs, such as epitope tags or sequences to aid in purification, may be incorporated into the nucleic acids. Preferably, the nucleic acids encoding the motifs may be at the 5' or 3' end of the nucleic acid, resulting in the presence of the motif at the N or C teriminus of the protein.

The cells used in the methods described herein may comprise a conjugate of an arrestin protein and a detectable molecule. In these methods, the cells may also comprise a conjugate of a GPCR and a detectable molecule.

The GPCR may be modified to have enhanced phosphorylation by a GRK. The GPCR may be $\beta_2AR(Y326A)$, a GPCR listed in FIG. 1, an orphan GPCR, a modified GPCR, a taste receptor, a Class A GPCR, a Class B GPCR, a mutant GPCR, or a biologically active fragment thereof.

All forms of arrestin, naturally occurring and engineered variants, including but not limited to, visual arrestin, βarrestin 1 and βarrestin 2, may be used in the present invention.

Detectable molecules that may be used to conjugate with the arrestin include, but are not limited to, molecules that are detectable by spectroscopic, photochemical, biochemical, immunochemical, electrical, radioactive, and optical means, including but not limited to bioluminescence, phosphorescence, and fluorescence. Detectable molecules include, but are not limited to, GFP, luciferase, β-galactosidase, rhodamine-conjugated antibody, and the like. Detectable molecules include radioisotopes, epitope tags, affinity labels, enzymes, fluorescent groups, chemiluminescent groups, and the like. Detectable molecules include molecules which are directly or indirectly detected as a function of their interaction with other molecule(s). These detectable molecules should be a biologically compatible molecule and should not compromise the ability of the arrestin to interact with the GPCR system and the interaction of the arrestin with the GPCR system must not compromise the ability of the detectable molecule to be detected. Preferred detectable molecules are optically detectable molecules, including optically detectable proteins, such that they may be excited chemically, mechanically, electrically, or radioactively to emit fluorescence, phosphorescence, or bioluminescence. More preferred detectable molecules are inherently fluorescent molecules, such as fluorescent proteins, including, for example, Green Fluorescent Protein (GFP). The detectable molecule may be conjugated to the arrestin protein by methods as described in Barak et al. (U.S. Pat. Nos. 5,891, 646 and 6,110,693). The detectable molecule may be conjugated to the arrestin at the front-end, at the back-end, or in the middle.

The TMR or GPCR or biologically active fragments thereof may also be conjugated with a detectable molecule. Preferably, the carboxyl-terminus of the TMR or GPCR is conjugated with a detectable molecule. A carboxyl-terminal tail conjugated or attached to a detectable molecule can be used in a carboxyl-terminal tail exchange to provide the detectably labeled GPCR.

If the TMR or GPCR is conjugated with a detectable molecule, proximity of the TMR or GPCR with the arrestin may be readily detected. In addition, if the TMR or GPCR is conjugated with a detectable molecule, compartmentalization of the TMR or GPCR with the arrestin may be readily confirmed. The detectable molecule used to conjugate with the TMRs or GPCRs may include those as described above, including, for example, optically detectable molecules, such that they may be excited chemically, mechanically, electrically, or radioactively to emit fluorescence, phosphorescence, or bioluminescence. Preferred optically detectable molecules may be detected by immunofluorescence, luminescence, fluorescence, and phosphorescence.

For example, the TMRs or GPCRs may be antibody labeled with an antibody conjugated to an immunofluorescence molecule or the TMRs or GPCRs may be conjugated with a luminescent donor. In particular, the TMRs or GPCRs may be conjugated with, for example, luciferase, for example, *Renilla* luciferase, or a rhodamine-conjugated antibody, for example, rhodamine-conjugated anti-HA mouse monoclonal antibody. Preferably, the carboxyl-terminal tail of the GPCR may be conjugated with a luminescent donor, for example, luciferase. The GPCR, preferably the carboxyl-terminal tail, also may be conjugated with GFP as described in L. S. Barak et al. "Internal Trafficking and Surface Mobility of a Functionally Intact $\beta_2$-Adrenergic Receptor-Green Fluorescent Protein Conjugate", *Mol. Pharm.* (1997) 51, 177-184.

Cell Types and Substrates

Cells derived from different species may be useful in the present invention. Cells may be derived from rat, mouse, pig, primate, or human, for example. Cells derived from particular animals, for example higher primates, may be required to detect the reduced internalization in the methods described herein. In certain aspects of the invention, cells derived from a particular species may be useful, or preferred. In certain aspects of the invention, cells derived from mammals are useful. In certain aspects of the invention, cells derived from rat, mouse, pig, primate, or human are useful.

The cells of the present invention may express at least one GPCR. The cells may further comprise a conjugate of an arrestin protein and a detectable molecule. Useful cells include eukaryotic and prokaryotic cells, including, but not limited to, bacterial cells, yeast cells, fungal cells, insect cells, nematode cells, plant cells, and animal cells. Suitable animal cells include, but are not limited to, HEK-293 cells, U2OS cells, HeLa cells, COS cells, and various primary mammalian cells. An animal model expressing a conjugate of an arrestin and a detectable molecule throughout its tissues or within a particular organ or tissue type, may also be used.

The cells of the present invention may express one modified protein that results in agonist-independent localization of TMRs or GPCRs to endocytic vesicles or endosomes.

A substrate may have deposited thereon a plurality of cells of the present invention. The substrate may be any suitable biologically substrate, including but not limited to, glass, plastic, ceramic, semiconductor, silica, fiber optic, diamond, biocompatible monomer, or biocompatible polymer materials.

The following examples are presented in order to more fully illustrate the preferred embodiments of the invention. They should in no way be construed, however, as limiting the broad scope of the invention.

EXAMPLES

Example 1

Method of Identifying a Transmembrane Receptor (TMR) Agonist

Cells containing human or rat GPCR, and arrestin-GFP were provided. Cells were exposed to 11 test compounds and 1 control compound. The signaling was measured at 30 min, 60 min, and 120 min after exposure to the compound. Translocation was measured at 30 min, 60 min, and 120 min after exposure to the compound. GPCR internalization was quantitatively determined in the presence of each test compound, as compared to the GPCR internalization in the presence of the control compound. See for example, FIG. 4-7. The GPCR internalization was reduced in the presence of certain compounds, as compared to the control compound. It was determined that signaling was activated in the presence of certain test compounds, as compared to signaling in the absence of agonist. Signaling and translocation were measured at multiple concentrations of compound. Dose response curves for signaling and translocation were generated. These experiments demonstrated that TMRAs could be identified by this method.

Signaling Measurement Method

GPCR signaling was measured using AlphaScreen™ from PerkinElmer.

The day before the experiment, two 125 ml spinner flasks of CHO cells were seeded at 100,000/ml in 90 ml of Ex-Cell Media (suspension media)+10% FBS+2 mM Glutamine+10 mM Hepes in a 125 ml spinner flask. To spinner flask #1, Baculovirus with a pFastBac plasmid containing Human GPCR DNA was added to yield 75 viral particles per cell (75 MOI). To spinner flask #2, Baculovirus with a pFastBac plasmid containing Rat GPCR DNA was added to yield 250 viral particles per cell (250 MOI). Incubated at 37° C. overnight.

The day before the experiment, two 125 ml spinner flasks of U2OS Rr#7 cells were seeded at 200,000/ml in 120 ml of Ex-Cell Media (suspension media)+10% FBS+2 mM Glutamine+10 mM Hepes in a 125 ml spinner flask. To spinner flask #3, Baculovirus with a pFastBac plasmid containing Human GPCR DNA was added to yield 75 viral particles per cell (75 MOI). To spinner flask #4, Baculovirus with a pFastBac plasmid containing Rat GPCR DNA was added to yield 250 viral particles per cell (250 MOI). Incubated at 37° C. overnight.

The day of the experiment: all reagents were prepared using silinized labware from frozen stocks brought to room temperature. Drug Media: EMEM supplemented with 2 mM Glutamine, 9% DMSO, 10 mM Hepes, 0.1% BSA. Cell Media: EMEM supplemented with 500 µM IBMX. cAMP: starting cAMP concentration for addition to plate was 1 µM and was serial diluted 1:3 for 16 total concentrations. Acceptor Beads: 272 µl of 3.75 mg/ml Anti-cAMP Acceptor Beads. Donor Bead Mix: a. For U2OS Rr#7: To EMEM added 5 µM Glutamine, 0.6% Tween 20, 3.3 nM biotinylated cAMP, 6.67 nM Streptavidin Donor Beads. b. For CHO: To EMEM add 5 µM Glutamine, 0.3% Tween 20, 3.3 nM biotinylated cAMP, 6.67 nM Streptavidin Donor Beads.

Compounds: compounds 1-12 were serially diluted (1:3) from a starting concentration of 1 µM in EMEM with 10 mM Hepes, 2 mM Glutamine and 0.1% BSA. Diluted compounds were consolidated on a Greiner deep well 384 plate for ease of dispensing via Minitrak.

Procedure: Time course of 30, 60, and 120 minutes for each of the four conditions (CHO/Human GPCR, CHO/Rat GPCR, U2OS Rr#7/Human GPCR, and U2OS Rr#7 Rat GPCR). 1. Labeled 13 clean 384 well Perkin Elmer Optiplates (12 plates for Compounds and 1 plate for cAMP standard curve) for each condition at 3 time points. 2. Prepared Drug Media. 3. Prepared Cell Media. 4. Prepared cAMP serial dilutions. 5. Counted cells for each of the 4 spinner flasks. 6. Centrifuged two aliquots (human GPCR and rat GPCR) of 4.5e6 CHO cells and resuspended in 30 ml of Cell Media (final concentration was 150000 cells/mL). 7. Centrifuged two aliquots (human GPCR and rat GPCR) of 12e6 U2OS Rr#7 cells and resuspended in 30 ml of Cell Media (final concentration was 400000 cells/mL). 8. Added 1.1 µl of compound serial dilution curves from the 384 deep well Greiner plate to dry Optiplates using the Minitrak. 9. Added 1.1 µl of cAMP serial dilution standard curves to a dry Optiplate using a BioHit manual pipettor. All subsequent steps are light sensitive and all plates and reagents remained under green filtered light or in the dark. 10. Prepared Donor Bead Mix (made at least 30 minutes prior to use). 11. Added 65.2 µl of 3.75 mg/ml Anti-cAMP Acceptor beads to each of the four 30 ml of cells/Cell Media. 12. Added 10.9 µl of 3.75 mg/ml Anti-cAMP Acceptor beads to 5 ml of Cell Media. 13. Added 20 µl/well of cells/cell media/acceptor beads to the Compound serial dilutions using the Multidrop. 14. Added 20 µl/well of cell media/acceptor beads to the cAMP serial dilutions. 15. Incubated at 37° Celsius and started timers. 16. After 30 minutes, added 10 µl/well Donor Bead Mix to the first set of four plates using the donor bead mix corresponding to the cell type. 17. After 60 minutes, added 10 µl/well Donor Bead Mix to the second set of four plates and the cAMP standard curve control plate using the donor bead mix corresponding to the cell type. 18. After 120 minutes, manually added 10 µl/well Donor Bead Mix to the third set of four plates using the donor bead mix corresponding to the cell type. 19. Sealed with clear adhesive TopSeal (PerkinElmer). 20. Read plates on the AlphaFusion™ (PE) 12 hrs after the assay. Left plates at room temperature in dark until read time. 21. Agonist curves were back calculated against cAMP standard curves Translocation Measurement Method GPCR translocation was measured using Transfluor™.

The day before the experiment, six IPA washed 384 well Matrical plates were labeled according to human GPCR at 3 time points (30, 60, 120 minutes) and Rat GPCR at 3 time point (30, 60, 120 minutes). U2OS Rr#7 cells (5.6e6) in 35 ml of Cell Growth Media were transduced with Human GPCR via baculovirus to achieve 75 viral particles per cell (75 MOI). U2OS Rr#7 cells (5.6e6) in 35 ml of Cell Growth Media* were transduced with Rat GPCR via baculovirus to achieve 250 viral particles per cell (250 MOI). U2OS Rr#7/Human GPCR cells were plated at 25 µl/well into three IPA washed, 384-well Matrical plates (4,000 cells/well final). U2OS Rr#7/Rat GPCR cells were plated at 25 µl/well into three IPA washed, 384-well Matrical plates (4,000 cells/well final). Incubated at 37° C. overnight. Cell Growth Media: MEM in addition to, 10% FBS, 10 mM Hepes, 2 mM Glutamine, 10 µg/ml Gentamicin, 0.4 mg/ml G418.

The day of the experiment: Reagent and Compound Preparation: all reagents were prepared using silinized labware from frozen stocks brought to room temperature. All values listed are final concentrations. Cell Media: EMEM supplemented with 2 mM Glutamine, 10 mM Hepes, 0.1% BSA. Compounds: compounds 1-12 were serially diluted (1:3) from a starting concentration of 1 μM in EMEM with 10 mM Hepes, 2 mM Glutamine and 0.1% BSA. Diluted compounds were consolidated on a Greiner deep well 384 plate for ease of dispensing via Minitrak. Fix and Stain: 1 μM DRAQ5 stain and 2% Formaldehyde.

Procedure: Time course of 30, 60, and 120 minutes for each of the two conditions (U2OS Rr#7 Human GPCR and U2OS Rr#7 Rat GPCR). 1. Prepared cell media. 2. Prepared compound serial dilution curves and consolidated in a 384 deep well Greiner plate. 3. Removed Cell growth media. 4. Added 25 μl/well Cell Media using the Multidrop. 5. Incubated for 30 minutes at 37° C. 6. Added 1.3 μl of Compound serial dilutions from the 384 deep well Greiner plate to the six Matrical plates using the Minitrak. 7. Incubated at 37° C. 8. Prepared Fix and Stain. 9. After 30 minutes, manually added 25 μl/well Fix and Stain to the first set of two plates. 10. After 60 minutes, manually added 25 μl/well Fix and Stain to the second set of two plates. 11. After 120 minutes, manually added 25 μl/well Fix and Stain to the third set of two plates. 12. Sealed plates with foil, adhesive seals. 13. Read on InCell Analyzer 3000, Generation 1 and analyzed for f-grains.

Example 2

Method of Identifying a Transmembrane Receptor (TMR) Agonist—Morphine Example

Cells containing μ opioid receptor, and arrestin-GFP were provided. Cells were exposed to morphine, the test compound. Cells were exposed to DAMGO, the control compound. The signaling was measured at 30 min, 60 min, and 120 min after exposure to the compound. Translocation was measured at 30 min, 60 min, and 120 min after exposure to the compound. It was then quantitatively determined that the MOR internalization was reduced in the presence of morphine, the test compound, as compared to the MOR internalization in the presence of DAMGO, the control compound. It was determined that signaling was activated in the presence of morphine, the test compound, as compared to signaling in the absence of agonist. Signaling and translocation were measured at multiple concentrations of compound. Dose response curves for signaling and translocation were generated. The results are shown in FIG. 8. These experiments demonstrated that morphine is a TMRA. While morphine is a TMRA, it may be derivitized to form a compound which further reduces MOR internalization.

Signaling Measurement Method

μ opioid receptor signaling was measured using ALPHASCREEN™ from PerkinElmer.

The day before the experiment, CHO cells were seeded at 100,000/ml in 70 ml of Ex-Cell Media (suspension media)+ 10% FBS+2 mM Glutamine+10 mM Hepes in a 125 ml spinner flask; 4.2 ml (1e9 stock) baculovirus was added at seeding thus yielding 600 viral particles per cell (600 MOI). Incubated at 37° C. overnight.

The day of the experiment: all reagents were made up fresh on the day of the assay unless noted otherwise. Agonists were from frozen stocks. Buffer: EMEM (SFM) in addition to 10 mM Hepes, 2 mM Glutamine. Drug Media: 4.5 ml 100% DMSO; 45.5 ml EMEM (SFM) in addition to 10 mM Hepes, 2 mM Glutamine (1:11 dilution); (1%=1 g/100 ml) 0.5 g BSA; Yields 10% DMSO, 1% BSA working concentration. Cell Media: 35 ml EMEM (SFM) in addition to 10 mM Hepes, 2 mM Glutamine; Add 35 μl (500 μM) IBMX (1:1000 dilution). Forskolin Media: 1 μl (1 mM) forskolin into 62.7 μl EMEM (SFM) in addition to 10 mM Hepes, 2 mM Glutamine (1:63.7 dilution). Yields 1.57e-3 working concentration. 36 μl (1.57e-3M forskolin) into 17.96 ml EMEM (SFM) in addition to 10 mM Hepes, 2 mM Glutamine (1:500 dilution); Yields 3.15e-6M working concentration. DAMGO: 2 μl (10 mM) DAMGO into 93.2 μl Drug Media (1:47.6 dilution); Yields 2.1e4M working concentration. 2.1e-4 M high concentration DAMGO (1:3) serial dilutions, 16 pts; 40 μl into 80 μl Drug media (using silinized tips and tip changes between dilutions). Morphine: 2 μl (10 mM) morphine into 93.2 μl Drug Media (1:47.6 dilution); Yields 2.1e-4M working concentration. 2.1e-4 M high concentration DAMGO (1:3) serial dilutions, 16 pts; 40 μl into 80 μl Drug media (using silinized tips and tip changes between dilutions). cAMP: 1 μl 5 mM cAMP into 179.7 μl Drug Media (1:180.7 dilution); Yields 2.8e-5 M working cAMP concentration. 2.8e-5 M high concentration cAMP (1:3) serial dilutions, 16 pts; 40 μl into 80 μl Drug media (using silinized tips and tip changes between dilutions). Acceptor Beads: 71.76 μl (3.75 mg/ml) beads added to 26 ml cells+cell media (1:362.3) dilution. 11 μl (3.75 mg/ml) beads added to 4 ml cell media (for cAMP wells). Donor Beads: (1:8) 2 ml 10% Tween-20; (1:730) 29 μl (10 μM) Biotinylated-cAMP; (1:180.5) 88.6 μl (5 mg/ml) donor beads; 13.89 ml EMEM (SFM) in addition to 10 mM Hepes, 2 mM Glutamine.

Procedure: 1. Made drug media. 2. Made cell media (thoroughly vortex IBMX into solution). 3. Made DAMGO, morphine and cAMP serial dilutions in drug media (using a Biohit pipette). 4. Added 10 μl of each concentration into designated wells of a silinized, 384-well Remp polypropylene plate. 5. Added 10 μl of buffer (drug media) to basal wells and wells that will receive only a maximum concentration of forskolin. (stock plate). 6. Aspirated appropriate volume from the stock plate and transfered 1.5 μl of drug/buffer into each of three Optiplates (PE) using a Minitrack instrument (PE). 7. Counted cells from spinner flask. Pelleted cells and resuspended in 26 ml of cell media (26 ml is enough volume for 3×384 plate). Final cell concentration was 6,000 cells per 20 μl. 8. Placed 4 ml of cell media in a separate tube (no cells). This was used for the cAMP serial dilutions. 9. All subsequent steps are light sensitive and all plates and reagents remained under green filtered light or in the dark. 10. Added 71.76 μl of acceptor beads to the resuspended cells and mixed gently. 11. Added 11 μl of acceptor beads to the cell media (containing no cells) and mixed. 12. Using a multidrop, dispensed 20 μl of cells+ acceptor to all wells except cAMP wells. 13. Added 20 μl of plain cell media+acceptor to cAMP wells, using a BioHit pipette. 14. Tapped plates gently to mix. 15. Incubated plate for 30 min at room temperature. 16. During incubation, made forskolin media. 17. After 30 min, added 10 μl of the working concentration of forskolin to all wells except for the basal and cAMP wells using a multidrop instrument. 18. Added 10 μl to basal and cAMP wells using a multidrop instrument. 19. Tapped plates gently to mix. 20. Incubated plate at 37° C. 21. Started timers. (Times set for 30 min, 60 min and 120 min). 22. Made donor bead media and incubated at room temperature in a drawer (complete darkness). This was incubated for at least 30 min before it was added to the first assay plate. 23. Dispensed 10 μl of donor mix to the entire assay plate using a multidrop instrument when each plate's time was up. 24. Tapped plates gently to mix. 25. Sealed with clear adhesive TopSeal (PerkinElmer). 26. Read plates on the AlphaFusion™ (PE) 12 hrs after the assay. Left plates at room temp in dark until read time. 27. Curves were fit using MDL's LSW data analysis wizard. 28. Agonist curves were back calculated against cAMP standard curves.

Final Concentrations: DAMGO: Serial dilutions started at 1 e-5M (1:3 16 pts), Morphine: Serial dilutions started at 1e-5M (1:3 16 pts), cAMP: Serial dilutions started at 1 e-6M (1:3 16 pts), Acceptor: 5 µg/ml, Forskolin: 1 e-6M, Donor: 0.3% Tween-20; 3.3 nM Biotinylated-cAMP; 6.67 µg/ml donor beads, Cells: 6,000/20 µl, DMSO: 0.36%, BSA: 0.036%

Translocation Measurement Method

µ opioid receptor (MOR) translocation was measured using Transfluor™.

The day before the experiment, U2OS-GFP-MOR stable cell line, containing MOR and arrestin-GFP, was plated in each of 3 IPA washed, 384-well Matrical plates at 5,000 cells/25 µl. Growing media: MEM in addition to, 10% FBS, 10 mM Hepes, 2 mM Glutamine. Incubate at 37° C. overnight.

The day of assay: Reagents Prep and dilutions. All reagents were made up fresh on the day of the assay unless noted otherwise. Agonists were from frozen stocks. All dilutions were performed with silinized tips and tip changes between dilutions. 1. Diluted DAMGO: 20 µl (1e-2) stock DAMGO into 180 µl of EMEM (SFM) in addition to 10 mM Hepes, 10% DMSO (1:100 dilution), 1% BSA (1 g/l 00 ml).

Yields: 1e-3M DAMGO working concentration. Serial dilutions (1:3) of the 1e-3M working stock (16 pts) in a 96-well polypropylene, silinized plate (40 µl into 80 µl). 2. Diluted Morphine: 20 µl (1e-2) stock morphine into 180 µl of EMEM (SFM) in addition to 10 mM Hepes, 10% DMSO (1:100 dilution), 1% BSA (1 g/100 ml). Yields: 1 e-3M morphine working concentration. Serial dilutions (1:3) of the 1 e-3M working stock (16 pts) in a 96-well polypropylene, silinized plate (40 µl into 80 µl). 3. Added 2 µl of serial dilutions into designated wells of a silinized, polypropylene, Remp 384-well plate. 4. Added 2 µl of buffer EMEM (SFM) in addition to 10 mM Hepes, 10% DMSO, 1% BSA to basal wells. 5. Added 2 µl of high concentration from the serial dilutions to a block of wells (max agonist) to use in order to calculate statistics. 6. Using a multidrop, dispensed 15 µl buffer EMEM (SFM) in addition to 10 mM Hepes, 10% DMSO, 1% BSA to the entire plate containing the 2 µl. This brought the serial dilution, high concentration to 1.18e-4 M. 7. Tapped plate to mix. 8. Removed the 25 µl of growing media from cells and replaced with 23 µl EMEM (SFM) in addition to 10 mM Hepes. (Minitrack instrument (PE)). 9. Aspirated 2 µl from the diluted drug plate and stamped onto the 23 µl in the assay plate. (Minitrack instrument (PE)). 10. Mixed using a 10 µl aspirate and dispense step. (Minitrack instrument (PE)). 11. Started timers. (Times were set for 30 min for plate 1, 60 min for plate2 and 120 min for plate3) 12. Added 25 µl of 4% formaldehyde+2 µM DRAQ5 nuclear dye to each assay plate when time has expired for each plate. (Final concentrations: 2% formaldehyde, 1 µM DRAQ5). 13. Sealed plates with foil, adhesive seals. 14. Read on InCell Analyzer 3000, Generation1 and analyzed for f-grains. 15. Curves were fit from MDL's LSW data analysis wizard.

While the invention has been described and illustrated herein by references to various specific material, procedures and examples, it is understood that the invention is not restricted to the particular material combinations of material, and procedures selected for that purpose. Numerous variations of such details can be implied as will be appreciated by those skilled in the art.

The following is a list of documents related to the above disclosure and particularly to the experimental procedures and discussions. The following documents, as well as any documents referenced in the foregoing text, should be considered as incorporated by reference in their entirety.

Attramadal, H., Arriza, J. L., Aoki, C., Dawson, T. M., Codina, J., Kwatra, M. M., Snyder, S. H., Caron, M. G. & Lefkowitz, R. J. (1992) J. Biol. Chem. 267, 17882-17890

Barak, L. S., Oakley, R. H., Laporte, S. A. and Caron, M. G. (2001) Proc. Natl. Acad. Sci. USA 98, 93-98

Barak, L. S., Warabi, K., Feng, X., Caron, M. G. & Kwatra, M. M. (1999) J. Biol. Chem. 274, 7565-7569

Barak, L. S., Ferguson, S. S., Zhang, J. & Caron, M. G. (1997) J. Biol. Chem. 272, 27497-27500

Barak, L. S., Ferguson, S. S., Zhang, J., Martenson, C., Meyer, T. & Caron, M. G. (1997) Mol. Pharmacol. 51,177-184

Barak, L. S., Menard, L., Ferguson, S. S., Colapietro, A. M. & Caron, M. G. (1995) Biochemistry 34, 15407-15414

Ferguson, S. S., Barak, L. S., Zhang, J. & Caron, M. G. (1996) Can. J. Physiol. Pharmacol. 74,1095-1110

Ferguson, S. S., Menard, L., Barak, L. S., Koch, W. J., Colapietro, A. M. & Caron, M. G. (1995) J. Biol. Chem. 270, 24782-24789

Inglese, J., Koch, W. J., Caron, M. G., Lefkowitz, R. J. (1992) Nature 359:147-150

Kim, K.-M., Valenzano, K. J., Robinson, S. R., Yao, W. D., Barak, L. S., Caron, M. G. (2001) J. Biol. Chem. 276: 37409-37414

Laporte, S. A., Oakley, R. H., Holt, J. A., Barak, L. S. & Caron, M. G. (2000) J. Biol. Chem. 275, 23120-23126

Laporte, S. A., Oakley, R. H., Zhang, J., Holt, J. A., Ferguson, S. S., Caron, M. G. & Barak, L. S. (1999) Proc. Natl. Acad. Sci. USA 96, 3712-3717

Menard, L., Ferguson, S. S., Zhang, J., Lin, F. T., Lefkowitz, R. J., Caron, M. G. &

Barak, L. S. (1997) Mol. Pharmacol. 51, 800-808

Mhaouty-Kodja, S., Barak, L. S., Scheer, A., Abuin, L., Diviani, D., Caron, M. G. &

Cotecchia, S. (1999) Mol. Pharmacol. 55, 339-347

Oakley, R. H., Laporte, S. A., Holt, J. A., Barak, L. S., Caron, M. G. (2001). J. Biol. Chem. 276: 19452-19460

Oakley, R. H., Laporte, S. A., Holt, J. A., Caron, M. G. & Barak, L. S. (2000) J. Biol. Chem. 275, 17201-17210

Oakley, R. H., Laporte, S. A., Holt, J. A., Barak, L. S. & Caron, M. G. (1999) J. Biol. Chem. 274, 32248-32257

Zhang, J., Barak, L. S., Anborgh, P. H., Laporte, S. A., Caron, M. G. & Ferguson, S. S. (1999) J. Biol. Chem. 274, 10999-11006

Zhang, J., Barak, L. S., Winkler, K. E., Caron, M. G. & Ferguson, S. S. (1997) J. Biol. Chem. 272, 27005-27014

The invention claimed is:

1. A method of identifying a G protein-coupled receptor (GPCR) agonist, wherein the GPCR agonist is capable of activating GPCR signaling while exhibiting reduced GPCR internalization as compared to a control compound, comprising the steps of:
   (a) providing a cell comprising at least one GPCR or a modified GPCR capable of activating intracellular signaling and an arrestin, or a fragment thereof capable of binding a GPCR,
   (b) exposing the cell to at least one test compound,
   (c) measuring GPCR signaling at two or more points in time,
   (d) measuring internalization of the GPCR at two or more points in time,
   (e) quantitatively determining if GPCR internalization is reduced by comparing GPCR internalization in the presence of the test compound to GPCR internalization in the presence of a control compound, and wherein-GPCR signaling is activated in the presence of the test compound as compared to GPCR signaling in the absence of the test compound,
   (f) wherein a reduction in GPCR internalization in the presence of the test compound as compared to the control compound indicates the test compound is a GPCR agonist capable of activating GPCR signaling while exhibiting reduced GPCR internalization.

2. The method of claim 1, wherein the internalization of the GPCR is measured by monitoring localization of a detectable molecule bound to the arrestin or to the GPCR.

3. The method of claim 1, wherein signaling is quantitated by measuring an intracellular effector, wherein said effector is cAMP, cyclic GMP, calcium, a lipid, phosphatidylinositol, a hydrogen ion, or an ion transport molecule.

4. The method of claim 1, wherein the signaling is activated for a longer time period after stimulation by the test compound than the length of time of activation after stimulation by the control compound.

5. The method of claim 1, wherein the internalization of the GPCR is measured by determining the localization of the GPCR in the plasma membrane, pits, endosomes, endocytic vesicles, or cytosol.

6. The method of claim 1, wherein the GPCR is a class A, or class B receptor.

7. The method of claim 1, wherein the GPCR is a μ opioid, $\beta_1 AR$, $\beta_2 AR$, or dopamine receptor.

8. The method of claim 1, wherein the internalization of the GPCR is measured by visualization of a radioisotope, an epirope tag, an affinity label, an enzyme, a fluorescent group, or a chemiluminescent group attached to the arrestin or the GPCR.

9. The method of claim 1, wherein the signaling is measured at the same time as the internalization is measured.

10. The method of claim 1, wherein the cell is exposed to the compound once, and wherein the cell is not exposed a second time to the compound.

11. The method of claim 1, wherein the GPCR is a rat, mouse, pig, or primate GPCR.

12. The method of claim 1, wherein the steps (a)-(f) are repeated, and wherein the GPCR used in the repeated steps is from a different species than ihe GPCR used in steps (a)(f).

13. The method of claim 12, wherein a test compound that is used in steps (a)-(f) is not used in the repeated steps.

14. The method of claim 1, wherein the test compound is from a combinatorial library.

15. The method of claim 1, wherein the signaling in the presence of the test compound is equal to or greater than the signaling in the presence of the control compound.

16. The method of claim 1, wherein the method is repeated at different concentrations of compound to yield a dose-response curve for the signaling measurement and a dose-response curve for the internalization measurement in the presence of the test compound.

17. The method of claim 16, wherein the quantitative determination includes a comparison of the dose-response curve for the signaling measurement to the dose-response curve for the internalization measurement.

18. The method of claim 16, wherein a second dose-response curve for the signaling measurement and a second dose-response curve for the internalization measurement are determined in the presence of control compound.

19. The method of claim 18, wherein the dose-response curve for the internalization measurement in the presence of the test compound is less than the dose-response curve for the internalization measurement in the presence of the control compound.

20. The method of claim 18, wherein the dose-response curve for the signaling measurement in the presence of the test compound is approximately equal to or greater than the dose-response curve for the signaling measurement in the presence of the control compound.

21. The method of claim 19, wherein the reduced internalization is determined by a decrease in the Max of the dose-response curve for the internalization measurement in the presence of the test compound, as compared to the Max of the dose-response curve for the internalization measurement in the presence of the control compound.

22. The method of claim 19, wherein the reduced internalization is determined by an increase in the EC50 of the dose-response curve for the internalization measurement in the presence of the test compound, as compared to the EC50 of the dose-response curve for the internalization measurement in the presence of the control compound.

23. A method of identifying a G protein-coupled receptor (GPCR) agonist, wherein the GPCR agonist is capable of activating GPCR signaling while exhibiting reduced GPCR internalization over a control compound, comprising the steps of:
(a) providing a cell comprising at least one GPCR or a modified GPCR capable of activating intracellular signaling and an arrestin, or a fragment thereof capable of binding a GPCR,
(b) exposing the cell to at least one test compound,
(c) measuring GPCR signaling at one or more concentration of the test compound,
(d) measuring internalization of the GPCR at one or more concentrations of the test compound,
(e) quantitatively determining if GPCR internalization is reduced by comparing GPCR internalization in the presence of the test compound to GPCR internalization in the presence of a control compound, and wherein GPCR signaling is activated in the presence of the test compound as compared to GPCR signaling in the absence of the test compound,
(f) wherein a reduction in GPCR internalization in the presence of the test compound as compared to the control compound indicates the test compound is a GPCR agonist capable of activating GPCR signaling while exhibiting reduced GPCR internalization.

24. The method of claim 23, wherein the internalization of GPCR is measured by monitoring localization of a detectable molecule bound to the arrestin or the GPCR.

25. The method of claim 23, wherein signaling is quantitated by measuring an intracellular effector, wherein said effector may be cAMP, cyclic GMP, calcium, a lipid, phosphatidylinositol, a hydrogen ion, or an ion transport molecule.

26. The method of claim 23, wherein the signaling is activated for a longer time period after stimulation by the test compound than the length of time of activation after stimulation by the control compound.

27. The method of claim 23, wherein the internalization of the GPCR is measured by determining the localization of the GPCR in the plasma membrane, pits, endosomes, endocytic vesicles, or cytosol.

28. The method of claim 23, wherein the GPCR is a class A, or class B receptor.

29. The method of claim 23, wherein the GPCR is a µ opioid, $\beta_1AR$, $\beta_2AR$, or dopamine receptor.

30. The method of claim 23, wherein the internalization of the GPCR is measured by visualization of a radioisotope, an epitope tag, an affinity label, an enzyme, a fluorescent group, or a chemiluminescent group attached to the arrestin or the GPCR.

31. The method of claim 23, wherein the signaling is measured at the same time as the internalization is measured.

32. The method of claim 23, wherein the cell is exposed to the compound once, and wherein the cell is not exposed a second time to the compound.

33. The method of claim 23, wherein the GPCR is a rat, mouse, pig, or primate GPCR.

34. The method of claim 23, wherein the steps (a)-(f) are repeated, and wherein the GPCR used in the repeated steps is from a different species than the GPCR used in steps (a)-(f).

35. The method of claim 34, wherein a test compound that is used in steps (a)-(f) is not used in the repeated steps.

36. The method of claim 23, wherein the rest compound is from a combinatorial library.

37. The method of claim 23, wherein the signaling in the presence of the test compound is approximately equal to or greater than the signaling in the presence of the control compound.

38. The method of claim 23, wherein the method is repeated at different concentrations of compound to yield a dose-response curve for the signaling measurement and a dose-response curve for the internalization measurements in the presence of the test compound.

39. The method of claim 38, wherein the quantitative determination includes a comparison of the dose-response curve for the signaling measurement to the dose-response curve for the internalization measurement.

40. The method of claim 38, wherein a second dose-response curve for the signaling measurement and a second dose-response curve for the internalization measurement are determined in the presence of control compound.

41. The method of claim 40, wherein the dose-response curve for the internalization measurement in the presence of the test compound is less than the dose-response curve for the internalization measurement in the presence of, the control compound.

42. The method of claim 40, wherein the dose-response curve for the signaling measurement in the presence of the test compound is approximately equal to or greater than the dose-response curve for the signaling measurement in the presence of the control compound.

43. The method of claim 41, wherein the reduced internalization is determined by a decrease in the Max of the dose-response curve for the internalization measurement in the presence of the test compound, as compared to the Max of the dose-response curve for the internalization measurement in the presence of the control compound.

44. The method of claim 41, wherein the reduced internalization is determined by an increase in the EC50 of the dose-response curve for the internalization measurement in the presence of the test compound, as compared to the EC50 of the dose-response curve for the internalization measurement in the presence of the control compound.

45. The method of claim 11, wherein the primate GPCR is a human GPCR.

46. The method of claim 33, wherein the primate GPCR is a human GPCR.

* * * * *

SEQUENCE LISTING

<160> NUMBER OF SEQ ID NOS: 41

<210> SEQ ID NO 1
<211> LENGTH: 5
<212> TYPE: PRT
<213> ORGANISM: Artificial Sequence
<220> FEATURE:
<223> OTHER INFORMATION: amino acid motif
<220> FEATURE:
<221> NAME/KEY: VARIANT
<222> LOCATION: 3, 4
<223> OTHER INFORMATION: Xaa = Any Amino Acid

<400> SEQUENCE: 1

Asn Pro Xaa Xaa Tyr
 1               5

<210> SEQ ID NO 2
<211> LENGTH: 4
<212> TYPE: PRT
<213> ORGANISM: Artificial Sequence
<220> FEATURE:
<223> OTHER INFORMATION: amino acid motif
<220> FEATURE:
<221> NAME/KEY: VARIANT
<222> LOCATION: 4
<223> OTHER INFORMATION: Xaa = Any Amino Acid

<400> SEQUENCE: 2

Cys Ala Ala Xaa
 1

<210> SEQ ID NO 3
<211> LENGTH: 43
<212> TYPE: PRT
<213> ORGANISM: Homo sapiens

<400> SEQUENCE: 3

Asn Pro Ile Val Tyr Ala Phe Arg Ile Gln Lys Phe Arg Val Thr Phe
 1               5                  10                  15

Leu Lys Ile Trp Asn Asp His Phe Arg Cys Gln Pro Ala Pro Pro Ile
                20                  25                  30

Asp Glu Asp Leu Pro Glu Glu Arg Pro Asp Asp
                35                  40

<210> SEQ ID NO 4
<211> LENGTH: 176
<212> TYPE: PRT
<213> ORGANISM: Homo sapiens

<400> SEQUENCE: 4

Asn Pro Ile Ile Tyr Pro Cys Ser Ser Lys Glu Phe Arg Ala Phe Val
 1               5                  10                  15

Arg Ile Leu Gly Cys Gln Cys Arg Gly Arg Gly Arg Arg Arg Arg Arg
                20                  25                  30

Arg Arg Arg Arg Leu Gly Gly Cys Ala Tyr Thr Tyr Arg Pro Trp Thr
                35                  40                  45

Arg Gly Gly Ser Leu Glu Arg Ser Gln Ser Arg Lys Asp Ser Leu Asp
                50                  55                  60

Asp Ser Gly Ser Cys Leu Ser Gly Ser Gln Arg Thr Leu Pro Ser Ala
65                  70                  75                  80

Ser Pro Ser Pro Gly Tyr Leu Gly Arg Gly Ala Pro Pro Pro Val Glu

```
                85                  90                  95
Leu Cys Ala Phe Pro Glu Trp Lys Ala Pro Gly Ala Leu Leu Ser Leu
            100                 105                 110

Pro Ala Pro Glu Pro Gly Arg Arg Gly Arg His Asp Ser Gly Pro
            115                 120                 125

Leu Phe Thr Phe Lys Leu Leu Thr Glu Pro Glu Ser Pro Gly Thr Asp
            130                 135                 140

Gly Gly Ala Ser Asn Gly Gly Cys Glu Ala Ala Ala Asp Val Ala Asn
145                 150                 155                 160

Gly Gln Pro Gly Phe Lys Ser Asn Met Pro Leu Ala Pro Gly Gln Phe
                165                 170                 175

<210> SEQ ID NO 5
<211> LENGTH: 29
<212> TYPE: PRT
<213> ORGANISM: Homo sapiens

<400> SEQUENCE: 5

Asn Pro Val Ile Tyr Thr Ile Phe Asn His Asp Phe Arg Arg Ala Phe
1               5                   10                  15

Lys Lys Ile Leu Cys Arg Gly Asp Arg Lys Arg Ile Val
            20                  25

<210> SEQ ID NO 6
<211> LENGTH: 29
<212> TYPE: PRT
<213> ORGANISM: Homo sapiens

<400> SEQUENCE: 6

Asn Pro Val Ile Tyr Thr Ile Phe Asn Gln Asp Phe Arg Arg Ala Phe
1               5                   10                  15

Arg Arg Ile Leu Cys Arg Pro Trp Thr Gln Thr Ala Trp
            20                  25

<210> SEQ ID NO 7
<211> LENGTH: 31
<212> TYPE: PRT
<213> ORGANISM: Homo sapiens

<400> SEQUENCE: 7

Asn Pro Val Ile Tyr Thr Val Phe Asn Gln Asp Phe Arg Pro Ser Phe
1               5                   10                  15

Lys His Ile Leu Phe Arg Arg Arg Arg Gly Phe Arg Gln
            20                  25                  30

<210> SEQ ID NO 8
<211> LENGTH: 105
<212> TYPE: PRT
<213> ORGANISM: Homo sapiens

<400> SEQUENCE: 8

Asn Pro Ile Ile Tyr Cys Arg Ser Pro Asp Phe Arg Lys Ala Phe Gln
1               5                   10                  15

Gly Leu Leu Cys Cys Ala Arg Arg Ala Ala Arg Arg Arg His Ala Thr
            20                  25                  30

His Gly Asp Arg Pro Arg Ala Ser Gly Cys Leu Ala Arg Pro Gly Pro
            35                  40                  45

Pro Pro Ser Pro Gly Ala Ala Ser Asp Asp Asp Asp Asp Val Val
        50                  55                  60
```

```
Gly Ala Thr Pro Pro Ala Arg Leu Leu Glu Pro Trp Ala Gly Cys Asn
 65                  70                  75                  80

Gly Gly Ala Ala Ala Asp Ser Asp Ser Ser Leu Asp Glu Pro Cys Arg
                 85                  90                  95

Pro Gly Phe Ala Ser Glu Ser Lys Val
            100                 105

<210> SEQ ID NO 9
<211> LENGTH: 92
<212> TYPE: PRT
<213> ORGANISM: Homo sapiens

<400> SEQUENCE: 9

Asn Pro Leu Ile Tyr Cys Arg Ser Pro Asp Phe Arg Ile Ala Phe Gln
  1               5                  10                  15

Glu Leu Leu Cys Leu Arg Arg Ser Ser Leu Lys Ala Tyr Gly Asn Gly
                 20                  25                  30

Tyr Ser Ser Asn Gly Asn Thr Gly Glu Gln Ser Gly Tyr His Val Glu
             35                  40                  45

Gln Glu Lys Glu Asn Lys Leu Leu Cys Glu Asp Leu Pro Gly Thr Glu
         50                  55                  60

Asp Phe Val Gly His Gln Gly Thr Val Pro Ser Asp Asn Ile Asp Ser
 65                  70                  75                  80

Gln Gly Arg Asn Cys Ser Thr Asn Asp Ser Leu Leu
                 85                  90

<210> SEQ ID NO 10
<211> LENGTH: 120
<212> TYPE: PRT
<213> ORGANISM: Homo sapiens

<400> SEQUENCE: 10

Asn Pro Ile Ile Tyr Ala Phe Asn Ala Asp Phe Arg Lys Ala Phe Ser
  1               5                  10                  15

Thr Leu Leu Gly Cys Tyr Arg Leu Cys Pro Ala Thr Asn Asn Ala Ile
                 20                  25                  30

Glu Thr Val Ser Ile Asn Asn Asn Gly Ala Ala Met Phe Ser Ser His
             35                  40                  45

His Glu Pro Arg Gly Ser Ile Ser Lys Glu Cys Asn Leu Val Tyr Leu
         50                  55                  60

Ile Pro His Ala Val Gly Ser Ser Glu Asp Leu Lys Lys Glu Glu Ala
 65                  70                  75                  80

Ala Gly Ile Ala Arg Pro Leu Glu Lys Leu Ser Pro Ala Leu Ser Val
                 85                  90                  95

Ile Leu Asp Tyr Asp Thr Asp Val Ser Leu Glu Lys Ile Gln Pro Ile
            100                 105                 110

Thr Gln Asn Gly Gln His Pro Thr
            115                 120

<210> SEQ ID NO 11
<211> LENGTH: 22
<212> TYPE: PRT
<213> ORGANISM: Homo sapiens

<400> SEQUENCE: 11

Asn Pro Ile Ile Tyr Thr Thr Phe Asn Ile Glu Phe Arg Lys Ala Phe
  1               5                  10                  15

Leu Lys Ile Leu His Cys
```

20

<210> SEQ ID NO 12
<211> LENGTH: 22
<212> TYPE: PRT
<213> ORGANISM: Homo sapiens

<400> SEQUENCE: 12

Asn Pro Val Ile Tyr Thr Thr Phe Asn Ile Glu Phe Arg Lys Ala Phe
1               5                   10                  15

Leu Lys Ile Leu Ser Cys
            20

<210> SEQ ID NO 13
<211> LENGTH: 24
<212> TYPE: PRT
<213> ORGANISM: Homo sapiens

<400> SEQUENCE: 13

Asn Pro Val Ile Tyr Thr Val Phe Asn Ala Glu Phe Arg Asn Val Phe
1               5                   10                  15

Arg Lys Ala Leu Arg Ala Cys Cys
            20

<210> SEQ ID NO 14
<211> LENGTH: 123
<212> TYPE: PRT
<213> ORGANISM: Homo sapiens

<400> SEQUENCE: 14

Asn Pro Val Ile Tyr Ala Phe Asn Ala Asp Phe Gln Lys Val Phe Ala
1               5                   10                  15

Gln Leu Leu Gly Cys Ser His Phe Cys Ser Arg Thr Pro Val Glu Thr
            20                  25                  30

Val Asn Ile Ser Asn Glu Leu Ile Ser Tyr Asn Gln Asp Ile Val Phe
        35                  40                  45

His Lys Glu Ile Ala Ala Ala Tyr Ile His Met Met Pro Asn Ala Val
    50                  55                  60

Thr Pro Gly Asn Arg Glu Val Asp Asn Asp Glu Glu Gly Pro Phe
65                  70                  75                  80

Asp Arg Met Phe Gln Ile Tyr Gln Thr Ser Pro Asp Gly Asp Pro Val
                85                  90                  95

Ala Glu Ser Val Trp Glu Leu Asp Cys Glu Gly Glu Ile Ser Leu Asp
            100                 105                 110

Lys Ile Thr Pro Phe Thr Pro Asn Gly Phe His
        115                 120

<210> SEQ ID NO 15
<211> LENGTH: 47
<212> TYPE: PRT
<213> ORGANISM: Homo sapiens

<400> SEQUENCE: 15

Asn Pro Met Cys Tyr Ala Leu Cys Asn Lys Ala Phe Arg Asp Thr Phe
1               5                   10                  15

Arg Leu Leu Leu Leu Cys Arg Trp Asp Lys Arg Arg Trp Arg Lys Ile
            20                  25                  30

Pro Lys Arg Pro Gly Ser Val His Arg Thr Pro Ser Arg Gln Cys
        35                  40                  45

<210> SEQ ID NO 16
<211> LENGTH: 31
<212> TYPE: PRT
<213> ORGANISM: Homo sapiens

<400> SEQUENCE: 16

Asn Pro Ala Cys Tyr Ala Leu Cys Asn Ala Thr Phe Lys Lys Thr Phe
1               5                   10                  15

Lys His Leu Leu Met Cys His Tyr Lys Asn Ile Gly Ala Thr Arg
            20                  25                  30

<210> SEQ ID NO 17
<211> LENGTH: 51
<212> TYPE: PRT
<213> ORGANISM: Homo sapiens

<400> SEQUENCE: 17

Asn Pro Val Cys Tyr Ala Leu Cys Asn Lys Thr Phe Arg Thr Thr Phe
1               5                   10                  15

Lys Met Leu Leu Leu Cys Gln Cys Asp Lys Lys Arg Arg Lys Gln
            20                  25                  30

Gln Tyr Gln Gln Arg Gln Ser Val Ile Phe His Lys Arg Ala Pro Glu
        35                  40                  45

Gln Ala Leu
    50

<210> SEQ ID NO 18
<211> LENGTH: 31
<212> TYPE: PRT
<213> ORGANISM: Homo sapiens

<400> SEQUENCE: 18

Asn Pro Ala Cys Tyr Ala Leu Cys Asn Ala Thr Phe Lys Lys Thr Phe
1               5                   10                  15

Arg His Leu Leu Leu Cys Gln Tyr Arg Asn Ile Gly Thr Ala Arg
            20                  25                  30

<210> SEQ ID NO 19
<211> LENGTH: 42
<212> TYPE: PRT
<213> ORGANISM: Homo sapiens

<400> SEQUENCE: 19

Asn Pro Ile Cys Tyr Ala Leu Cys Asn Arg Thr Phe Arg Lys Thr Phe
1               5                   10                  15

Lys Met Leu Leu Leu Cys Arg Trp Lys Lys Lys Val Glu Glu Lys
            20                  25                  30

Leu Tyr Trp Gln Gly Asn Ser Lys Leu Pro
        35                  40

<210> SEQ ID NO 20
<211> LENGTH: 24
<212> TYPE: PRT
<213> ORGANISM: Homo sapiens

<400> SEQUENCE: 20

Asn Pro Val Ile Tyr Ala Tyr Phe Asn Lys Asp Phe Gln Asn Ala Phe
1               5                   10                  15

Lys Lys Ile Ile Lys Cys Lys Phe
            20

<210> SEQ ID NO 21
<211> LENGTH: 26
<212> TYPE: PRT
<213> ORGANISM: Homo sapiens

<400> SEQUENCE: 21

Asn Pro Ile Ile Tyr Thr Met Ser Asn Glu Asp Phe Lys Gln Ala Phe
 1               5                  10                  15

His Lys Leu Ile Arg Phe Lys Cys Thr Ser
            20                  25

<210> SEQ ID NO 22
<211> LENGTH: 24
<212> TYPE: PRT
<213> ORGANISM: Homo sapiens

<400> SEQUENCE: 22

Asn Pro Leu Leu Tyr Thr Ser Phe Asn Glu Asp Phe Lys Leu Ala Phe
 1               5                  10                  15

Lys Lys Leu Ile Arg Cys Arg Glu
            20

<210> SEQ ID NO 23
<211> LENGTH: 37
<212> TYPE: PRT
<213> ORGANISM: Homo sapiens

<400> SEQUENCE: 23

Asn Pro Ile Ile Tyr Cys Leu Arg Asn Gln Glu Val Lys Arg Ala Leu
 1               5                  10                  15

Cys Cys Ile Leu His Leu Tyr Gln His Gln Asp Pro Asp Pro Lys Lys
            20                  25                  30

Gly Ser Arg Asn Val
        35

<210> SEQ ID NO 24
<211> LENGTH: 27
<212> TYPE: PRT
<213> ORGANISM: Homo sapiens

<400> SEQUENCE: 24

Asn Pro Leu Ile Tyr Thr Leu Arg Asn Met Glu Val Lys Gly Ala Leu
 1               5                  10                  15

Arg Arg Leu Leu Gly Lys Gly Arg Glu Val Gly
            20                  25

<210> SEQ ID NO 25
<211> LENGTH: 62
<212> TYPE: PRT
<213> ORGANISM: Homo sapiens

<400> SEQUENCE: 25

Asn Pro Leu Phe Tyr Gly Phe Leu Gly Lys Lys Phe Lys Arg Tyr Phe
 1               5                  10                  15

Leu Gln Leu Leu Lys Tyr Ile Pro Pro Lys Ala Lys Ser His Ser Asn
            20                  25                  30

Leu Ser Thr Lys Met Ser Thr Leu Ser Tyr Arg Pro Ser Asp Asn Val
        35                  40                  45

Ser Ser Ser Thr Lys Lys Pro Ala Pro Cys Phe Glu Val Glu
    50                  55                  60

```
<210> SEQ ID NO 26
<211> LENGTH: 50
<212> TYPE: PRT
<213> ORGANISM: Homo sapiens

<400> SEQUENCE: 26

Asn Pro Phe Leu Tyr Cys Phe Val Gly Asn Arg Phe Gln Gln Lys Leu
 1               5                  10                  15

Arg Ser Val Phe Arg Val Pro Ile Thr Trp Leu Gln Gly Lys Arg Glu
            20                  25                  30

Ser Met Ser Cys Arg Lys Ser Ser Leu Arg Glu Met Glu Thr Phe
        35                  40                  45

Val Ser
    50

<210> SEQ ID NO 27
<211> LENGTH: 51
<212> TYPE: PRT
<213> ORGANISM: Homo sapiens

<400> SEQUENCE: 27

Asn Pro Leu Ile Tyr Ala Phe Ile Gly Gln Lys Phe Arg His Gly Leu
 1               5                  10                  15

Leu Lys Ile Leu Ala Ile His Gly Leu Ile Ser Lys Asp Ser Leu Pro
            20                  25                  30

Lys Asp Ser Arg Pro Ser Phe Val Gly Ser Ser Ser Gly His Thr Ser
        35                  40                  45

Thr Thr Leu
    50

<210> SEQ ID NO 28
<211> LENGTH: 67
<212> TYPE: PRT
<213> ORGANISM: Homo sapiens

<400> SEQUENCE: 28

Asn Pro Leu Ile Tyr Ala Phe Ala Gly Glu Lys Phe Arg Arg Tyr Leu
 1               5                  10                  15

Tyr His Leu Tyr Gly Lys Cys Leu Ala Val Leu Cys Gly Arg Ser Val
            20                  25                  30

His Val Asp Phe Ser Ser Ser Glu Ser Gln Arg Ser Arg His Gly Ser
        35                  40                  45

Val Leu Ser Ser Asn Phe Thr Tyr His Thr Ser Asp Gly Asp Ala Leu
    50                  55                  60

Leu Leu Leu
65

<210> SEQ ID NO 29
<211> LENGTH: 59
<212> TYPE: PRT
<213> ORGANISM: Homo sapiens

<400> SEQUENCE: 29

Asn Pro Ile Leu Tyr Asn Leu Val Ser Ala Asn Phe Arg His Ile Phe
 1               5                  10                  15

Leu Ala Thr Leu Ala Cys Leu Cys Pro Val Trp Arg Arg Arg Arg Lys
            20                  25                  30

Arg Pro Ala Phe Ser Arg Lys Ala Asp Ser Val Ser Ser Asn His Thr
        35                  40                  45
```

```
Leu Ser Ser Asn Ala Thr Arg Glu Thr Leu Tyr
    50                  55
```

<210> SEQ ID NO 30
<211> LENGTH: 107
<212> TYPE: PRT
<213> ORGANISM: Homo sapiens

<400> SEQUENCE: 30

```
Asn Pro Ile Ile Tyr Cys Cys Leu Asn Asp Arg Phe Arg Leu Gly Phe
 1               5                  10                  15
Lys His Ala Phe Arg Cys Cys Pro Phe Ile Ser Ala Gly Asp Tyr Glu
            20                  25                  30
Gly Leu Glu Met Lys Ser Thr Arg Tyr Leu Gln Thr Gln Gly Ser Val
        35                  40                  45
Tyr Lys Val Ser Arg Leu Glu Thr Thr Ile Ser Thr Val Val Gly Ala
    50                  55                  60
His Glu Glu Pro Glu Asp Gly Pro Lys Ala Thr Pro Ser Ser Leu
65                  70                  75                  80
Asp Leu Thr Ser Asn Cys Ser Ser Arg Ser Asp Ser Lys Thr Met Thr
                85                  90                  95
Glu Ser Phe Ser Phe Ser Ser Asn Val Leu Ser
            100                 105
```

<210> SEQ ID NO 31
<211> LENGTH: 50
<212> TYPE: PRT
<213> ORGANISM: Homo sapiens

<400> SEQUENCE: 31

```
Asn Pro Trp Ile Tyr Ala Ser Phe Ser Ser Val Ser Ser Glu Leu Arg
 1               5                  10                  15
Ser Leu Leu Cys Cys Ala Arg Gly Arg Thr Pro Pro Ser Leu Gly Pro
            20                  25                  30
Gln Asp Glu Ser Cys Thr Thr Ala Ser Ser Ser Leu Ala Lys Asp Thr
        35                  40                  45
Ser Ser
    50
```

<210> SEQ ID NO 32
<211> LENGTH: 83
<212> TYPE: PRT
<213> ORGANISM: Homo sapiens

<400> SEQUENCE: 32

```
Asn Pro Val Ile Tyr Asn Leu Met Ser Gln Lys Phe Arg Ala Ala Phe
 1               5                  10                  15
Arg Lys Leu Cys Asn Cys Lys Gln Lys Pro Thr Glu Lys Pro Ala Asn
            20                  25                  30
Tyr Ser Val Ala Leu Asn Tyr Ser Val Ile Lys Glu Ser Asp His Phe
        35                  40                  45
Ser Thr Glu Leu Asp Asp Ile Thr Val Thr Asp Thr Tyr Leu Ser Ala
    50                  55                  60
Thr Lys Val Ser Phe Asp Asp Thr Cys Leu Ala Ser Glu Val Ser Phe
65                  70                  75                  80
Ser Gln Ser
```

```
<210> SEQ ID NO 33
<211> LENGTH: 65
<212> TYPE: PRT
<213> ORGANISM: Homo sapiens

<400> SEQUENCE: 33

Asn Pro Trp Ile Tyr Met Leu Phe Thr Gly His Leu Phe His Glu Leu
1               5                   10                  15

Val Gln Arg Phe Leu Cys Cys Ser Ala Ser Tyr Leu Lys Gly Arg Arg
            20                  25                  30

Leu Gly Glu Thr Ser Ala Ser Lys Lys Ser Asn Ser Ser Ser Phe Val
        35                  40                  45

Leu Ser His Arg Ser Ser Ser Gln Arg Ser Cys Ser Gln Pro Ser Thr
    50                  55                  60

Ala
65

<210> SEQ ID NO 34
<211> LENGTH: 75
<212> TYPE: PRT
<213> ORGANISM: Homo sapiens

<400> SEQUENCE: 34

Asn Pro Val Leu Tyr Ser Leu Met Ser Ser Arg Phe Arg Glu Thr Phe
1               5                   10                  15

Gln Glu Ala Leu Cys Leu Gly Ala Cys Cys His Arg Leu Arg Pro Arg
            20                  25                  30

His Ser Ser His Ser Leu Ser Arg Met Thr Thr Gly Ser Thr Leu Cys
        35                  40                  45

Asp Val Gly Ser Leu Gly Ser Trp Val His Pro Leu Ala Gly Asn Asp
    50                  55                  60

Gly Pro Glu Ala Gln Gln Glu Thr Asp Pro Ser
65                  70                  75

<210> SEQ ID NO 35
<211> LENGTH: 62
<212> TYPE: PRT
<213> ORGANISM: Homo sapiens

<400> SEQUENCE: 35

Asn Pro Leu Val Tyr Cys Phe Met His Arg Arg Phe Arg Gln Ala Cys
1               5                   10                  15

Leu Glu Thr Cys Ala Arg Cys Cys Pro Arg Pro Pro Arg Ala Arg Pro
            20                  25                  30

Arg Ala Leu Pro Asp Glu Asp Pro Pro Thr Pro Ser Ile Ala Ser Leu
        35                  40                  45

Ser Arg Leu Ser Tyr Thr Thr Ile Ser Thr Leu Gly Pro Gly
    50                  55                  60

<210> SEQ ID NO 36
<211> LENGTH: 82
<212> TYPE: PRT
<213> ORGANISM: Homo sapiens

<400> SEQUENCE: 36

Asn Pro Leu Val Tyr Ala Leu Ala Ser Arg His Phe Arg Ala Arg Phe
1               5                   10                  15

Arg Arg Leu Trp Pro Cys Gly Arg Arg Arg His Arg Ala Arg Arg
            20                  25                  30
```

```
Ala Leu Arg Arg Val Arg Pro Ala Ser Ser Gly Pro Pro Gly Cys Pro
        35                  40                  45

Gly Asp Ala Arg Pro Ser Gly Arg Leu Leu Ala Gly Gly Gln Gly
    50                  55                  60

Pro Glu Pro Arg Glu Gly Pro Val His Gly Gly Glu Ala Ala Arg Gly
65                  70                  75                  80

Pro Glu

<210> SEQ ID NO 37
<211> LENGTH: 76
<212> TYPE: PRT
<213> ORGANISM: Homo sapiens

<400> SEQUENCE: 37

Asn Pro Ile Ile Tyr Thr Leu Thr Asn Lys Glu Met Arg Arg Ala Phe
1               5                   10                  15

Ile Arg Ile Met Ser Cys Cys Lys Cys Pro Ser Gly Asp Ser Ala Gly
            20                  25                  30

Lys Phe Lys Arg Pro Ile Ile Ala Gly Met Glu Phe Ser Arg Ser Lys
        35                  40                  45

Ser Asp Asn Ser Ser His Pro Gln Lys Asp Glu Gly Asp Asn Pro Glu
    50                  55                  60

Thr Ile Met Ser Ser Gly Asn Val Asn Ser Ser
65                  70                  75

<210> SEQ ID NO 38
<211> LENGTH: 80
<212> TYPE: PRT
<213> ORGANISM: Homo sapiens

<400> SEQUENCE: 38

Asn Pro Ile Ile Tyr Ala Leu Arg Ser Lys Asp Leu Arg His Ala Phe
1               5                   10                  15

Arg Ser Met Phe Pro Ser Cys Glu Gly Thr Ala Gln Pro Leu Asp Asn
            20                  25                  30

Ser Met Gly Asp Ser Asp Cys Leu His Lys His Ala Asn Asn Ala Ala
        35                  40                  45

Ser Val His Arg Ala Ala Glu Ser Cys Ile Lys Ser Thr Val Lys Ile
    50                  55                  60

Ala Lys Val Thr Met Ser Val Ser Thr Asp Thr Ser Ala Glu Ala Leu
65                  70                  75                  80

<210> SEQ ID NO 39
<211> LENGTH: 59
<212> TYPE: PRT
<213> ORGANISM: Homo sapiens

<400> SEQUENCE: 39

Asn Pro Val Leu Tyr Ala Phe Leu Asp Glu Asn Phe Lys Arg Cys Phe
1               5                   10                  15

Arg Gln Leu Cys Arg Lys Pro Cys Gly Arg Pro Asp Pro Ser Ser Phe
            20                  25                  30

Ser Arg Pro Arg Glu Ala Thr Ala Arg Glu Arg Val Thr Ala Cys Thr
        35                  40                  45

Pro Ser Asp Gly Pro Gly Gly Arg Ala Ala
    50                  55

<210> SEQ ID NO 40
```

```
<211> LENGTH: 58
<212> TYPE: PRT
<213> ORGANISM: Homo sapiens

<400> SEQUENCE: 40

Asp Pro Phe Val Tyr Tyr Phe Val Ser His Asp Phe Arg Asp His Ala
1               5                   10                  15

Lys Asn Ala Leu Leu Cys Arg Ser Val Arg Thr Val Lys Gln Met Gln
            20                  25                  30

Val Ser Leu Thr Ser Lys Lys His Ser Arg Lys Ser Ser Ser Tyr Ser
            35                  40                  45

Ser Ser Ser Thr Thr Val Lys Thr Ser Tyr
    50                  55

<210> SEQ ID NO 41
<211> LENGTH: 66
<212> TYPE: PRT
<213> ORGANISM: Homo sapiens

<400> SEQUENCE: 41

Asn Gly Glu Val Gln Ala Glu Leu Arg Arg Lys Trp Arg Arg Trp His
1               5                   10                  15

Leu Gln Gly Val Leu Gly Trp Ser Ser Lys Ser Gln His Pro Trp Gly
            20                  25                  30

Gly Ser Asn Gly Ala Thr Cys Ser Thr Gln Val Ser Met Leu Thr Arg
            35                  40                  45

Val Ser Pro Ser Ala Arg Arg Ser Ser Ser Phe Gln Ala Glu Val Ser
    50                  55                  60

Leu Val
65
```